United States Patent
Duong et al.

(10) Patent No.: US 7,312,087 B2
(45) Date of Patent: Dec. 25, 2007

(54) DEVICES AND METHODS FOR BIOCHIP MULTIPLEXING

(75) Inventors: Hau H. Duong, Los Angeles, CA (US); Gary Blackburn, Glendora, CA (US); Jon F. Kayyem, Pasadena, CA (US); Stephen D. O'Connor, Pasadena, CA (US); Gary T. Olsen, La Cresenta, CA (US); Robert Pietri, Pasadena, CA (US); Robert H. Terbrueggen, Manhattan Beach, CA (US)

(73) Assignee: Clinical Micro Sensors, Inc., Pasadena, CA (US)

( * ) Notice: Subject to any disclaimer, the term of this patent is extended or adjusted under 35 U.S.C. 154(b) by 182 days.

(21) Appl. No.: 09/760,384

(22) Filed: Jan. 11, 2001

(65) Prior Publication Data

US 2007/0189921 A1 Aug. 16, 2007

(51) Int. Cl.
  *C12Q 1/68* (2006.01)
  *G01N 15/06* (2006.01)
  *G01N 33/00* (2006.01)
  *G01N 33/48* (2006.01)
  *G01N 35/00* (2006.01)

(52) U.S. Cl. ............... 436/149; 422/50; 422/68.1; 422/82.01; 422/82.05; 436/43; 436/63; 436/64; 436/66; 436/150; 205/775; 205/792; 205/793.5; 204/164; 204/461; 204/193; 204/194; 204/400; 204/403.01; 204/403.02; 204/403.03; 204/406; 204/407

(58) Field of Classification Search ............ 422/50, 422/55, 56, 58, 68.1, 81, 82.01, 82.05; 436/8, 436/43, 174, 501, 63, 64, 66, 149, 150; 73/1.01; 137/1, 87.01, 154; 251/205; 438/1; 205/775, 205/792, 793.5; 204/164, 461, 193, 194, 204/400, 403.01, 403.02, 403.03, 406, 407
See application file for complete search history.

(56) References Cited

U.S. PATENT DOCUMENTS 3,619,511 A 11/1971 Ishikawa (Continued)

FOREIGN PATENT DOCUMENTS

CA 2 090 904 A1 9/1993

(Continued)

OTHER PUBLICATIONS

Bain et al., "Formation of Monolayers by the Coadsorption of Thiols on Gold: Variation in the Length of the Alkyl Chain," J. Am. Chem. Soc. 111:7164-7175 (1989).

(Continued)

*Primary Examiner*—Brian Sines
(74) *Attorney, Agent, or Firm*—Morgan Lewis & Bockius LLP; Robin M. Silva

(57) ABSTRACT

The invention is directed to devices and methods that allow for simultaneous multiple biochip analysis. The method of analyzing the plurality of biochips includes inserting a first biochp into a first station of an analysis device, inserting a second biochip into a second station of the analysis device, wherein each of the first and second biochips include a substrate, the substrates including an array of detection electrodes, each electrode including a different capture binding ligand, a different target analyte, and a label, and a plurality of electrical contracts, detecting current as an indication of the presence of the labels on the first biochip, and detecting current as an indication of the presence of the labels on the first second biochip. The devices and method may be used with multiple cartridges comprising biochips comprising arrays, such as nucleic acid arrays, and allow for high throughput analysis of samples.

14 Claims, 41 Drawing Sheets

U.S. PATENT DOCUMENTS

| | | | |
|---|---|---|---|
| 4,072,576 A | 2/1978 | Arwin et al. | |
| 4,599,303 A * | 7/1986 | Yabusaki et al. | 435/6 |
| 4,704,193 A | 11/1987 | Bowers et al. | |
| 4,707,352 A | 11/1987 | Stavrianopoulos | |
| 4,707,440 A | 11/1987 | Stavrianopoulos | |
| 4,711,955 A | 12/1987 | Ward et al. | |
| 4,713,347 A | 12/1987 | Mitchell et al. | |
| 4,735,907 A | 4/1988 | Schaeffer et al. | |
| 4,755,458 A | 7/1988 | Rabbani et al. | |
| 4,787,963 A | 11/1988 | MacConnell | |
| 4,840,893 A | 6/1989 | Hill et al. | |
| 4,849,513 A | 7/1989 | Smith et al. | |
| 4,868,103 A | 9/1989 | Stavrianopoulos et al. | |
| 4,877,830 A | 10/1989 | Dobeli et al. | |
| 4,882,013 A | 11/1989 | Turner et al. | |
| 4,894,325 A | 1/1990 | Englehardt et al. | |
| 4,920,047 A | 4/1990 | Giaever et al. | |
| 4,943,523 A | 7/1990 | Stavrianopoulos | |
| 4,945,045 A | 7/1990 | Forrest et al. | |
| 4,952,685 A | 8/1990 | Stavrianopoulos | |
| 4,964,972 A | 10/1990 | Sagiv et al. | |
| 4,994,373 A | 2/1991 | Stavrianopoulos | |
| 5,002,885 A | 3/1991 | Stavrianopoulos | |
| 5,013,831 A | 5/1991 | Stavrianopoulos | |
| 5,038,852 A | 8/1991 | Johnson et al. | |
| 5,064,618 A | 11/1991 | Baker et al. | |
| 5,066,372 A | 11/1991 | Weetall | |
| 5,082,830 A | 1/1992 | Brakel et al. | |
| 5,089,112 A | 2/1992 | Skotheim et al. | |
| 5,100,775 A | 3/1992 | Smyczek et al. | |
| 5,126,034 A | 6/1992 | Carter et al. | |
| 5,156,810 A | 10/1992 | Ribi | |
| 5,164,319 A | 11/1992 | Hafeman et al. | |
| 5,175,269 A | 12/1992 | Stavrianopoulos | |
| 5,180,968 A | 1/1993 | Bruckenstein et al. | |
| 5,192,507 A | 3/1993 | Taylor et al. | |
| 5,238,808 A | 8/1993 | Bard et al. | |
| 5,241,060 A | 8/1993 | Englehardt et al. | |
| 5,242,828 A | 9/1993 | Bergstrom et al. | |
| 5,264,103 A | 11/1993 | Yoshioka et al. | |
| 5,278,043 A | 1/1994 | Bannwarth et al. | |
| 5,296,375 A | 3/1994 | Kricka et al. | |
| 5,304,487 A | 4/1994 | Wilding et al. | |
| 5,308,754 A | 5/1994 | Kankare et al. | |
| 5,312,527 A | 5/1994 | Mikkelsen et al. | |
| 5,320,808 A * | 6/1994 | Holen et al. | 422/64 |
| 5,328,824 A | 7/1994 | Ward et al. | |
| 5,356,786 A | 10/1994 | Heller et al. | |
| 5,391,272 A | 2/1995 | O'Daly et al. | |
| 5,403,451 A | 4/1995 | Riviello et al. | |
| 5,436,161 A | 7/1995 | Bergstrom et al. | |
| 5,438,607 A * | 8/1995 | Przygoda, Jr. et al. | 379/38 |
| 5,443,701 A | 8/1995 | Willner et al. | |
| 5,449,767 A | 9/1995 | Ward et al. | |
| 5,472,881 A | 12/1995 | Beebe et al. | |
| 5,476,928 A | 12/1995 | Ward et al. | |
| 5,486,335 A | 1/1996 | Wilding et al. | |
| 5,491,097 A | 2/1996 | Ribi et al. | |
| 5,498,392 A | 3/1996 | Wilding et al. | |
| 5,505,321 A | 4/1996 | Caron et al. | |
| 5,519,635 A | 5/1996 | Miyake et al. | |
| 5,532,128 A | 7/1996 | Eggers et al. | |
| 5,545,531 A | 8/1996 | Rava et al. | |
| 5,552,270 A | 9/1996 | Khrapko et al. | |
| 5,565,552 A | 10/1996 | Magda et al. | |
| 5,571,568 A | 11/1996 | Ribi et al. | |
| 5,573,906 A | 11/1996 | Bannwarth et al. | |
| 5,582,984 A | 12/1996 | Bieniarz et al. | |
| 5,585,069 A | 12/1996 | Zanzucchi et al. | |
| 5,587,128 A | 12/1996 | Wilding et al. | |
| 5,591,578 A | 1/1997 | Meade et al. | |
| 5,593,838 A | 1/1997 | Zanzucchi et al. | |
| 5,595,908 A | 1/1997 | Fawcett et al. | |
| 5,601,982 A | 2/1997 | Sargent et al. | |
| 5,603,351 A | 2/1997 | Cherukuri et al. | |
| 5,605,662 A | 2/1997 | Heller et al. | |
| 5,620,850 A | 4/1997 | Bamdad et al. | |
| 5,622,821 A | 4/1997 | Selvin et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,643,738 A | 7/1997 | Zanzucchi et al. | |
| 5,650,061 A | 7/1997 | Kuhr et al. | |
| 5,653,939 A | 8/1997 | Hollis et al. | |
| 5,670,322 A | 9/1997 | Eggers et al. | |
| 5,681,484 A | 10/1997 | Zanzucchi et al. | |
| 5,694,932 A | 12/1997 | Michel | |
| 5,700,667 A | 12/1997 | Marble et al. | |
| 5,705,346 A | 1/1998 | Okamoto et al. | |
| 5,705,348 A | 1/1998 | Meade et al. | |
| 5,726,026 A | 3/1998 | Wilding et al. | |
| 5,727,548 A | 3/1998 | Hill et al. | |
| 5,728,532 A | 3/1998 | Ackley | |
| 5,741,462 A | 4/1998 | Nova et al. | |
| 5,741,700 A | 4/1998 | Ershov et al. | |
| 5,747,169 A | 5/1998 | Fan et al. | |
| 5,755,942 A | 5/1998 | Zanzucchi et al. | |
| 5,756,050 A | 5/1998 | Ershov et al. | |
| 5,759,777 A * | 6/1998 | Kearney et al. | 435/6 |
| 5,770,029 A | 6/1998 | Nelson et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,234 A * | 7/1998 | Meade et al. | 435/6 |
| 5,795,453 A | 8/1998 | Gilmartin | |
| 5,824,473 A | 10/1998 | Meade et al. | |
| 5,837,859 A | 11/1998 | Teoule et al. | |
| 5,846,708 A | 12/1998 | Hollis et al. | |
| 5,849,486 A | 12/1998 | Heller et al. | |
| 5,851,772 A | 12/1998 | Mirzabekov et al. | |
| 5,856,174 A | 1/1999 | Lipshutz et al. | |
| 5,863,502 A | 1/1999 | Southgate et al. | |
| 5,866,345 A | 2/1999 | Wilding et al. | |
| 5,871,918 A | 2/1999 | Thorp et al. | |
| 5,874,046 A | 2/1999 | Megerle | |
| 5,874,219 A | 2/1999 | Rava et al. | |
| 5,876,926 A * | 3/1999 | Beecham | 435/5 |
| 5,891,630 A | 4/1999 | Eggers et al. | |
| 5,922,591 A | 7/1999 | Anderson et al. | |
| 5,929,208 A | 7/1999 | Heller et al. | |
| 5,942,397 A | 8/1999 | Tarlov et al. | |
| 5,942,443 A | 8/1999 | Parce et al. | |
| 5,945,286 A | 8/1999 | Krihak et al. | |
| 5,945,334 A | 8/1999 | Besemer et al. | |
| 5,952,172 A | 9/1999 | Meade et al. | |
| 5,965,452 A | 10/1999 | Kovacs | |
| 5,968,745 A | 10/1999 | Thorp et al. | |
| 5,972,692 A | 10/1999 | Hashimoto et al. | |
| 5,976,802 A | 11/1999 | Ansorge et al. | |
| 5,989,402 A * | 11/1999 | Chow et al. | 204/601 |
| 6,013,170 A | 1/2000 | Meade | |
| 6,013,459 A | 1/2000 | Meade | |
| 6,017,696 A * | 1/2000 | Heller | 435/6 |
| 6,050,719 A * | 4/2000 | Winkler et al. | 366/144 |
| 6,054,277 A * | 4/2000 | Furcht et al. | 435/6 |
| 6,060,023 A | 5/2000 | Maracas | |
| 6,060,327 A | 5/2000 | Keen | |
| 6,071,699 A | 6/2000 | Meade et al. | |
| 6,087,100 A | 7/2000 | Meade et al. | |
| 6,090,545 A | 7/2000 | Wohlstadter et al. | |
| 6,090,933 A | 7/2000 | Kayyem et al. | |
| 6,096,273 A | 8/2000 | Kayyem et al. | |
| 6,096,561 A * | 8/2000 | Tayi | 436/518 |

| | | | |
|---|---|---|---|
| 6,096,825 A | 8/2000 | Garnier | |
| 6,100,045 A | 8/2000 | Van Es | |
| 6,100,099 A | 8/2000 | Gordon et al. | |
| 6,107,080 A | 8/2000 | Lennox et al. | |
| 6,114,122 A * | 9/2000 | Besemer et al. | 435/6 |
| 6,117,973 A * | 9/2000 | Batz et al. | 530/300 |
| 6,132,685 A * | 10/2000 | Kercso et al. | 422/104 |
| 6,153,737 A | 11/2000 | Manoharan et al. | |
| 6,177,250 B1 | 1/2001 | Meade et al. | |
| 6,180,352 B1 | 1/2001 | Meade et al. | |
| 6,197,515 B1 | 3/2001 | Bamdad et al. | |
| 6,200,761 B1 | 3/2001 | Meade et al. | |
| 6,203,758 B1 | 3/2001 | Marks et al. | |
| 6,207,369 B1 * | 3/2001 | Wohlstadter et al. | 435/6 |
| 6,211,356 B1 | 4/2001 | Wiessler et al. | |
| 6,221,583 B1 | 4/2001 | Kayyem et al. | |
| 6,232,062 B1 | 5/2001 | Kayyem et al. | |
| 6,238,870 B1 | 5/2001 | Meade et al. | |
| 6,258,545 B1 | 7/2001 | Meade et al. | |
| 6,258,593 B1 | 7/2001 | Schembri et al. | |
| 6,264,825 B1 | 7/2001 | Blackburn et al. | |
| 6,268,149 B1 | 7/2001 | Meade et al. | |
| 6,268,150 B1 | 7/2001 | Meade et al. | |
| 6,277,576 B1 | 8/2001 | Meade et al. | |
| 6,288,221 B1 * | 9/2001 | Grinstaff et al. | 536/25.3 |
| 6,290,839 B1 | 9/2001 | Kayyem et al. | |
| 6,300,141 B1 | 10/2001 | Segal | |
| 6,303,316 B1 * | 10/2001 | Kiel et al. | 435/6 |
| 6,306,584 B1 | 10/2001 | Bamdad | |
| 6,322,979 B1 | 11/2001 | Bamdad et al. | |
| 6,326,211 B1 | 12/2001 | Anderson et al. | |
| 6,461,490 B1 * | 10/2002 | Lennox et al. | 204/403.08 |
| 6,479,240 B1 | 11/2002 | Kayyem | |
| 6,495,323 B1 | 12/2002 | Kayyem et al. | |
| 6,541,617 B1 * | 4/2003 | Bamdad et al. | 536/23.1 |
| 6,579,231 B1 * | 6/2003 | Phipps | 600/300 |
| 6,686,150 B1 | 2/2004 | Blackburn et al. | |
| 6,699,382 B2 | 3/2004 | Yoshioka et al. | |
| 6,740,518 B1 | 5/2004 | Duong et al. | |
| 6,942,771 B1 | 9/2005 | Kayyem et al. | |
| 2001/0034033 A1 | 10/2001 | Meade et al. | |
| 2001/0046679 A1 | 11/2001 | Meade et al. | |
| 2002/0006643 A1 | 1/2002 | Kayyem et al. | |
| 2003/0003473 A1 | 1/2003 | Kayyem et al. | |
| 2003/0150723 A1 | 8/2003 | Kayyem et al. | |
| 2005/0211559 A1 | 9/2005 | Kayyem et al. | |

FOREIGN PATENT DOCUMENTS

| | | |
|---|---|---|
| EP | 0 063 879 A2 | 11/1982 |
| EP | 0 142 301 A2 | 5/1985 |
| EP | 0 234 938 A2 | 2/1987 |
| EP | 0 213 825 A2 | 3/1987 |
| EP | 0 229 943 B1 | 7/1987 |
| EP | 0 439 036 | 7/1991 |
| EP | 0 478 319 A1 | 4/1992 |
| EP | 0 599 337 A2 | 1/1994 |
| EP | 0 637 996 B1 | 2/1995 |
| EP | 0 637 998 B1 | 2/1995 |
| EP | 0 515 615 | 9/1996 |
| EP | 1 043 588 A1 | 10/2000 |
| EP | 0668502 B1 | 5/2002 |
| JP | 238166 A | 10/1988 |
| JP | 05-196596 | 8/1993 |
| JP | 6-41183 A2 | 2/1994 |
| JP | 11-352094 | 12/1999 |
| WO | WO86/05815 | 3/1985 |
| WO | WO90/05303 A1 | 5/1990 |
| WO | WO90/05732 A1 | 5/1990 |
| WO | WO92/10757 A1 | 6/1992 |
| WO | WO93/10267 A1 | 5/1993 |
| WO | WO93/22678 | 11/1993 |
| WO | WO 93/23425 A1 | 11/1993 |
| WO | WO 93/25898 A1 | 12/1993 |
| WO | WO 94/22889 A1 | 10/1994 |
| WO | WO94/22889 A1 | 10/1994 |
| WO | WO95/15971 A2 | 6/1995 |
| WO | WO 95/35102 A1 | 12/1995 |
| WO | WO 96/06946 A1 | 3/1996 |
| WO | WO 96/15450 A1 | 5/1996 |
| WO | WO 96/15576 A1 | 5/1996 |
| WO | WO 96/39252 A1 | 12/1996 |
| WO | WO 96/39260 A1 | 12/1996 |
| WO | WO96/40712 A1 | 12/1996 |
| WO | WO97/01646 A2 | 1/1997 |
| WO | WO 97/16561 A1 | 5/1997 |
| WO | WO98/57159 A1 | 6/1997 |
| WO | WO 97/27324 A1 | 7/1997 |
| WO | WO97/27329 A1 | 7/1997 |
| WO | WO97/31256 | 8/1997 |
| WO | WO 97/37755 A1 | 10/1997 |
| WO | WO97/41425 | 11/1997 |
| WO | WO 97/43629 A1 | 11/1997 |
| WO | WO97/44651 A1 | 11/1997 |
| WO | WO 98/12539 A1 | 11/1997 |
| WO | WO97/46568 A1 | 12/1997 |
| WO | WO 97/46568 A1 | 12/1997 |
| WO | WO 98/01758 A1 | 1/1998 |
| WO | WO 98/05424 A1 | 2/1998 |
| WO | WO98/05424 A1 | 2/1998 |
| WO | WO 98/12359 A1 | 3/1998 |
| WO | WO98/12539 A1 | 3/1998 |
| WO | WO 98/13683 A1 | 4/1998 |
| WO | WO 98/15893 A1 | 4/1998 |
| WO | WO98/20162 A2 | 5/1998 |
| WO | WO98/27229 A1 | 6/1998 |
| WO | WO98/28444 A2 | 7/1998 |
| WO | WO 98/31839 A2 | 7/1998 |
| WO | WO98/31839 A2 | 7/1998 |
| WO | WO 98/35232 A2 | 8/1998 |
| WO | WO98/35232 A2 | 8/1998 |
| WO | WO 98/35232 A3 | 8/1998 |
| WO | WO 98/50154 A1 | 11/1998 |
| WO | WO98/51823 | 11/1998 |
| WO | WO98/57158 | 12/1998 |
| WO | WO99/14596 A1 | 3/1999 |
| WO | WO99/29711 | 6/1999 |
| WO | WO 99/29711 A1 | 6/1999 |
| WO | WO99/33559 A1 | 7/1999 |
| WO | WO 99/33559 A1 | 7/1999 |
| WO | WO 99/34213 A1 | 7/1999 |
| WO | WO99/37819 A2 | 7/1999 |
| WO | WO98/57319 | 11/1999 |
| WO | WO99/57317 | 11/1999 |
| WO | WO99/57319 | 11/1999 |
| WO | WO99/67425 A2 | 12/1999 |
| WO | WO 00/16089 A2 | 3/2000 |
| WO | WO 00/16089 A3 | 3/2000 |
| WO | WO 00/62931 A1 | 10/2000 |
| WO | WO00/62931 A1 | 10/2000 |
| WO | WO 01/06016 A2 | 1/2001 |
| WO | WO 01/06016 A3 | 1/2001 |
| WO | WO 01/35100 A2 | 5/2001 |
| WO | WO 01/35100 A3 | 5/2001 |
| WO | WO 01/54813 A2 | 8/2001 |
| WO | WO 01/54813 A3 | 8/2001 |
| WO | WO 01/43864 A3 | 6/2002 |
| WO | WO 02/43864 A2 | 6/2002 |

OTHER PUBLICATIONS

Bamdad, C. "A DNA self-assembled monolayer for the specific attachment of unmodified double- or single stranded DNA," Biophysical Journal, 75:1997-2003 (1988).

Beattie et al., "Genosensor Technology," Clinical Chemistry, 39(4): 719-722 (1993).

Ihara et al., "Gene sensor using ferrocenyl oligonucleotide," Chem. Commun., 1609-1610 (1997).

Langen et al., "Electron Tunneling in Proteins: Coupling Through a ββ Strand," Science, 268:1733-1735, 1995.

McGee et al., "Novel Nucleosides via Intramolecular Functionalization of 2,2'-Anhydrouridine Derivatives," Tetrahedron Letters, 37(12) 1995-1998 (1996).

Moffatt. "Chemical Transformations of the Sugar Moity of Nucleosides," Contribution No. 527 from the Institute of Organic Chemistry, Syntex Research; 71-165 (1979).

Mutz et al., "Conformational dependence of electron transfer across de novo designed metalloproteins," Proc. Natl. Acad. Sci. USA, 93:9521-9526, 1996.

Strobel, S. A., et al., "Site-Specific Cleavage of a Yeast Chromosome by Oligonucleotide-Directed Triple-Helix Formation," *Science*, 249:73-75 (1990).

Yu et al. "Uridine-conjugated-ferrocene DNA oligonucleotides for electronic detection of nucleic acids," Abstracts of Papers. ACS Ntational Meeting, 217(1): 76 (1999).

Dontha et al., "Generation of Biotin/Avidin/Enzyme Nanostructures with Maskless Photolithography," Anal. Chem. 69:2619-2625 (1997).

Aizawa et al., "Integrated Molecular Systems for Biosensors," Sensors and Acuators B, B@$ (Nos. 1/3) Part 1:1-5 (Mar. 1995).

Albers et al., "Design of Novel Molecular Wires for Realizing Long-Distance Electron Transfer," Biochemistry and Bioenergetics, 42:25-33 (1997).

Alleman, K.S., et al., "Electrochemical Rectification at a Monolayer-Modified Electrode," *J. Phys. Chem.*, 100:17050-17058 (1996).

Arkin et al. "Evidence for Photoelectron Transfer Through DNA Intercalation," *J. Inorganic Biochem. Abstracts*, 6th International Conference on Bioinorganic Chemistry, 51(1) & (2):526 (1993).

Barisci et al., "Conducting Polymer Sensors," *TRIP*, 4(9):307-311 (1996).

Baum, R. M., "Views on Biological, Long-Range Electron Transfer Stir Debate," *C&EN*, pp. 20-23 (1993).

Bechtold, R., et al., "Ruthenium-Modified Horse Heart Cytochrome c: Effect of pH and Ligation on the Rate of Intramolecular Electron Transfer between Ruthenium(II) and Heme(III)," *J. Phys. Chem.*, 90(16):3800-3804 (1986).

Bidan, "Electroconducting conjugated polymers: new sensitive matrices to build up chemical or electrochemical sensors. A Review.," *Sensors and Actuators*, B6:45-56 (1992).

Biotechnology and Genetics: Genetic Screening Integrated Circuit, *The Economist* (Feb. 25-Mar. 3, 1995).

Blonder et al., "Three-dimensional Redox-Active layered Composites of Au—Au, Ag—Ag and Au—Ag Colloids," Chem. Commun. 1393-1394 (1998).

Boguslavsky, L. et al., "Applications of redox polymers in biosensors," *Solid State Ionics*, 60:189-197 (1993).

Bowler, B. E., et al., "Long-Range Electron Transfer in Donor (Spacer) Acceptor Molecules and Proteins," *Progress in Inorganic Chemistry: Bioinorganic Chemistry*, 38:259-322 (1990).

Brun, A. M., et al., "Photochemistry of Intercalated Quaternary Diazaaromatic Salts," *J. Am. Chem. Soc.*, 113:8153-8159 (1991).

Bumm, et al., "Are Single Molecular Wires Conducting?," *Science* 271:1705-1707 (1996).

Cantor, C.R. et al., "Report on the Sequencing by Hybridization Workshop," *Genomics*, 13:1378-1383 (1992).

Carr et al., "Novel Electrochemical Sensors for Neutral Molecules," *Chem. Commun.*, 1649-1650 (1997).

Carter et al., "Voltammetric Studies of the Interaction of Metal Chelates with DNA. 2. Tris-Chelated Complexes of Cobalt(III) and Iron(II) with 10-Phenanthroline and 2,2'-Bipyridine," *J. Am. Chem. Soc.*, 11:8901-8911 (1989).

Chang, I-Jy, et al., "High-Driving-Force Electron Transfer in Metalloproteins: Intramolecular Oxidation of Ferrocytochrome c by Ru(2,2'-bpy)$_2$(im)(His-33)$^{3+}$," *J. Am. Chem. Soc.*, 113:7056-7057 (1991).

Chidsey, et al., "Coadsorption of Ferrocene-Terminated and Unsubstituted Alkanethiols on Gold Electroactive Self-Assembled Monolayers," *J. Am. Chem. Soc.*, 112:4301-4306 (1990).

Chidsey, C.E.D., et al., "Free Energy and Temperature Dependence of Electron Transfer at the Metal Electrolyte Interface," *Science*, 251:919-922 (1991).

Chrisey, et al., "Covalent attachment of synthetic DNA to self-assembled monolayer films," *Nucleic Acids Research*, 24(15):3031-3039 (1996).

Clery, "DNA Goes Electric," *Science*, 267:1270 (1995).

*Commerce Business Daily Issue* of Sep. 26, 1996 PSA#1688.

Davis, L. M., et al., Electron Donor Properties of the Antitumour Drug Amsacrine as Studied by Fluorescence Quenching of DNA-Bound.

Davis, L. M., et al., "Elements of buosensor construction," *Enzyme Microb. Technol.* 17:1030-1035 (1995).

Degani et al., "Direct Electrical Communication between Chemically Modified Enzymes and Metal Electrodes. 2. Methods for Bonding Electron-Transfer Relays to Glucose Oxidase and D-Amino-Acid Oxidase," *J. Am. Chem. Soc.* 110:2615-2620 (1988).

Degani, Y., et al., "Electrical Communication between Redox Centers of Glucose Oxidase and Electrodes via Electrostatically and Covalently Bound Redox Polymers," *J. Am. Chem. Soc.*, 111:2357-2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285-1288 (1987).

Deinhammer, R.S., et al., "Electronchemical Oxidation of Amine-containing compounds: A Route to the Surface Modification of glassy carbon electrodes," *Langmuir*, 10:1306-1313 (1994).

Dreyer, G. B., et al., "Sequence-specific cleavage of single-stranded DNA: Oligodeoxynucleotide-EDTA·Fe(II)," *Proc. Natl. Acad. Sci. USA*, 82:968-972 (1985).

Drobyshev, A. et al., "Sequence Analysis by Hybridization with Oligonucleotide Microchip: Identification of β-thalassemia Mutations," Gene, 188:45-52 (1997).

Dubiley, S. et al., "Fractionation, phosphorylation and Ligation on Oligonucleotide Microchips to Enhance Sequencing by Hybridization," Nucleic Acids Research, 25(12):2259-2265 (1997).

Durham, B., et al., "Electron-Transfer Kinetics of Singly Labeled Ruthenium(II) Polypyridine Cytochrome c Derivatives," *Advances in Chemistry Series*, 226:181-193 (1990).

Durham, B., et al., "Photoinduced Electron-Transfer Kinetics of Singly Labeled Ruthenium Bis(bipyridin) Dicarboxybipyridine Cytochrome c Derivatives," *Biochemistry*, 28:8659-8665 (1989).

Elghanian et al., "Selective Colorimetric Detection of Polynucleotides Based on the Distance-Dependent Optical Properties of Gold Nanoparticles," Science, 277:1078-1081 (1997).

Elias, H., et al., "Electron-Transfer Kinetics of Zn-Substituted Cytochrome c and Its Ru(NH$_3$)$_5$(Histidine-33) Derivative," *J. Am. Chem. Soc.*, 110:429-434 (1988).

Farver, O., et al., "Long-range intramolecular electron transfer in azurins," *Proc. Natl. Acad. Sci. USA*, 86:6968-6972 (1989).

Fotin, A. et al., "Parallel Thermodynamic Analysis of Duplexes on Oligodeoxyribonucleotide Microchips," Nucleic Acids Research, 216(6):1515-1521 (1998).

Fox, M. A., et al., "Light-Harvesting Polymer Systems," *C&EN*, pp. 38-48 (Mar. 15, 1993).

Fox, L. S., et al., "Gaussian Free-Energy Dependence of Electron-Transfer Rates in Iridium Complexes," *Science*, 247:1069-1071 (1990).

Francois, J-C., et al., "Periodic Cleavage of Poly(dA) by Oligothymidylates Covalently Linked to the 1,10-Phenanthroline-Copper Complex," *Biochemistry*, 27:2272-2276 (1988).

Friedman, A. E., et al., "Molecular 'Light Switch' for DNA: Ru(bpy)$_2$(dppz)$^{2+}$," *J. Am. Chem. Soc.*, 112:4960-4962 (1990).

Fromherz, P., et al., "Photoinduced Electron Transfer in DNA Matrix from Intercalated Ethidium to Condensed Methylviologen," *J. Am. Chem. Soc.*, 108:5361-5362 (1986).

Gardner, et al., "Application of conducting polymer technology in microsystems," *Sensors and Actuators*, A51:57-66 (1995).

Gregg, B. A., et al., "Redox Polymer Films Containing Enzymes. 1. A Redox-Conducting Epoxy Cement: Synthesis, Characterization, and Electrocatalytic Oxidation of Hydroquinone," *J. Phys. Chem.*, 95:5970-5975 (1991).

Gregg, B. A., et al., "Cross-linked redox gels containing glucose oxidase for amperometric biosensor applications," *Anal. Chem.*, 62:258-263 (1990).

Guschin, D. et al., "Manual Manufacturing of Oligonucleotide, DNA, and Protein Microchips," Analytical Biochemistry, 250:203-211 (1997).

Guschin, D. et al., "Oligonucleotide Microchips as Genosensors for Determinative and Environmental Studies in Microbiology," 63(6):2397-2402 (1997).

Hashimoto, et al., "Sequence-Specific Gene Detection with a Gold Electrode Modified with DNA Probes and an Electrochemically Active Dye," *Anal. Chem.* 66:3830-3833 (1994).

Hegner, et al., "Immobilizing DNA on gold via thiol modification for atomic force microscopy imaging in buffer solutions," *FEBS* 336(3):452-456 (1993).

Heller, A., "Electrical Wiring of Redox Enzymes," *Acc. Chem. Res.*, 23:128-134 (1990).

Heller et al., "Fluorescent Energy Transfer Oligonucleotide Probes," *Fed. Proc.* 46(6):1968 (1987) Abstract No. 248.

Heller, A., et al., "Amperometric biosensors based on three-dimensional hydrogel-forming epoxy networks," *Sensors and Actuators*, 13-14:180-183 (1993).

Ho "DNA-Mediated Electron Transfer and Application to 'Biochip'Development," *Abstract. Office of Naval Research* (Report Date: Jul. 25, 1991) 1-4, RR04106.

Hobbs et al., "Polynucleotides Containing 2'-Amino-2'deoxyribose and 2'-Azido-2'-deoxyriose," *Biochemistry*, 12(25):5138-5145 (1973).

Hsung, et al., "Thiophenol Protecting Groups for the Palladium-Catalyzed Heck Reaction: Efficient Syntheses of Conjugated Arylthiols," *Tetrahedron Letters.* 36(26):4525-4528 (1995).

Hsung, et al., "Synthesis and Characterization of Unsymmetric Ferrocene-Terminated Phenylethynyl Oligomers," *Organometallics*, 14:4808-4815 (1995).

Jenkins et al., A Sequence-Specific Molecular Light Switch: Tebhering of an Oligonucleotide to a Dipyridophenazine Complex of Ruthenium (II), *J. Am. Chem. Soc.*, 114:8736-8738 (1992).

Johnston et al., "Trans-Dioxorhenium(V)-Mediated Electrocatalytic Oxidation of DNA at Indium Tin-Oxide Electrodes: Voltammetric Detection of DNA Cleavage in Solution," *Inorg. Chem.*, 33:6388-6390 (1994).

Kamat et al., J. Phys. chem., 93(4):1405-1409 (1989). Abstract.

Katritzky, et al., "Pyridylethylation—A New Protection Method for Active Hydrogen Compounds," *Tetrahedron Letters*,25(12):1223-1226 (1984).

Kelley, S.O. and J.K. Barton, "Electrochemistry of Methylene Blue Bound to a DNA-Modified Electrode," *Bioconjugate Chem.*, 8:31-37 (1997).

Kojima et al., "A DNA Probe of Ruthenium Bipyridine Complex Using Photocatalytic Activity," *Chemistry Letter*, pp. 1889-1982 (1989).

Korri-Youssoufi et al., "Toward Bioelectronics: Specific DNA Recognition Based on an Oligonucleotide-Functionalized Polypyrrole," *J. Am. Chem. Soc.*, 119(31):7388-7389 (1997).

Laviron, E., "A.C. Polarography and Faradaic Impedance of Strongly Adsorbed Electroactive Species. Part I: Theoretical and Experimental Study of a Quasi-Reversible Reaction in the Case of a Langmuir Isotherm," *J. Electroanal. Chem.*, 97:135-149 (1979).

Laviron, E., "A.C. Polarography and Faradaic Impedance of Strongly Adsorbed Electoactive Species. Part III: Theoretical Complex Plane Analysis for a Surface Redox Reaction," *J. Electroanal. Chem.*, 105:35-42 (1979).

Lee, et al., "Direct Measurement of the Forces Between Complementary Strands of DNA," *Science*, 266:771-773 (1994).

Lenhard, J.R., et al., "Part VII Covalent Bonding of a Reversible-Electrode Reactanbt to Pt Electrodes Using an organosilane Reagent" *J. Electronal. Chem.*, 78:195-201 (1977).

Lincoln et al., "Shorting Circuiting the Molecular Wire," J. Am. Chem. Soc., 119(6)1454-1455 (1997).

Lipkin "Identifying DNA by the Speed of Electrons," *Science News*, 147(8):117 (1995).

Livshits, M. et al., "Theoretical Analysis of the Kinetics of DNA Hybridization with Gel-Immobilized Oligonucleotides," Biophysical Journal, 71:2795-2801 (1996).

Maskos, et al., "Oligonucleotide hybridisations on glass supports: a novel linker for oligonucleotide synthesis and hybridisation properties of oligonucleotides synthesised in situ," *Nucleic Acids Research*, 20(7):1679-1684 (1992).

McGee, et al., "2'-Amino-2'-deoxyuridine *via* an Intramolecular Cyclization of a Trichloroacetimidate," *J. Org. Chem.*, 61:781-785 (1996).

Meade, T. J., et al., "Electron Transfer through DNA: Site-Specific Modification of Duplex DNA with Ruthenium Donors and Acceptors," *Angew Chem. Int. Ed. Engl.*, 34:352-354 (1995).

Meade, T. J., "Driving-Force Effects on the Rate of Long-Range Electron Transfer in Ruthenium-Modified Cytochrome c," *J. Am. Chem. Soc.*, 111:4353-4356 (1989).

Mestel, "'Electron Highway' Points to Identity of DNA," *New Scientist*, p. 21 (1995).

Millan, K.M. and Mikkelsen, S.R., "Sequence-Selective Biosensor for DNA Based on Electroactive Hybridization Indicators," *Anal. Chem.*, 65:2317-2323 (1993).

Millan, K.M., et al., "Covalent Immobilization of DNA onto Glassy Carbon Electrodes," *Electroanalysis*, 4(10):929-932 (1992).

Millan, et al., "Voltammetric DNA Biosensor for Cystic Fibrosis Based on a Modified Carbon Paste Electrode," *Anal. Chem.*, 66:2943-2948 (1994).

Miller, C., "Absorbed ω-Hydroxy Thiol Monolayers on Gold Electrodes: Evidence for Electron Tunneling to Redox Species in Solution," *J. Phys. Chem.*, 95:877-886 (1991).

Mirkin et al., "A DNA-based Method for Ratioally Assembling Nonoparticles into Macroscopic Materials," Nature, 382:607-609 (1996).

Mirzabekov, A. et al., "Dna Sequencing by Hybridization—a Megasequencing Method and a Diagnostic Tool," Tibtech, 12:27-32 (1994).

Mitchell et al., "Programmed Assembly of DNA Functionalized Quantum Dots," J. Am. Chem. Soc., 121:8122-8123 (1999).

Mucic et al., "DNA-Directed Synthesis of Binary Nanoparticle Network Materials," J. Am. Chem. Soc., 120:12674-12675 (1998).

Murphy, C. J., et al., "Long-Range Photoinduced Electron Transfer Through a DNA Helix," *Science*, 262:1025-1029 (1993).

Orellana, G., et al., "Photoinduced Electron Transfer Quenching of Excited Ru(II) Polypyridyls Bound to DNA: The Role of the Nucleic Acid Double Helix," *Photochemistry and Photobiology*, 54(4):499-509 (1991).

Palecek, "From Polarography of DNA to Microanalysis with Nucleic Acid-Modified Electrodes," *Electroanalysis.* 8(1):7-14 (1996).

Parinov, S., "DNA Sequencing by Hybridization to Microchip octa- and Decanucleotides Extended by Stacked Pentanucleotides," Nucleic Acids Research, 24(15):2998-3004 (1996).

Paterson, "Electric Genes: Current Flow in DNA Could Lead to Faster Genetic Testing," *Scientific American*, 33 (May 1995).

Proudnikov, D., "Immobilization of DNA in Polyacrylamide Gel for the manufacture of DNA and DNA-Oligonucleotide Microchips," Analytical Biochemistry, 259:34-41 (1998).

Proudnikov, D. et al., "Chemical Methods of DNA and RNA Fluorescent Labeling," Nucleic Acids Research, 24(22):4535-4542 (1996).

Purugganan, M. D., et al., Accelerated Electron Transfer Between Metal Complexes Mediated by DNA, *Science*, 241:1645-1649 (1988).

Reimers et al., "Toward Efficient Molecular Wires and Switches: the Brooker Ions," Biosystems, 35:107-111 (1995).

Rhodes, D. And A. Klug, "Helical Periodicity of DNA Determined by Enzyme Digestion," *Nature*, 286:573-578 (1980).

Risser, S. M., et al., "Electron Transfer in DNA: Predictions of Exponential Growth and Decay of Coupling with Donor-Acceptor Distance," *J. Am. Chem. Soc.*, 115(6):2508-2510 (1993).

Sato, Y., et al., "Unidirectional Electron Transfer at Self-Assembled Monolayers of 11-Ferrocenyl-1-undecanethiol on Gold," *Bull. Chem. Soc. Jpn.*, 66(4):1032-1037 (1993).

Satyanarayana, S., et al., "Neither Δ- nor Λ-Tris(phenanthroline)ruthenium(II) Binds to DNA by Classical Intercalation," *Biochemistry*, 31(39):9319-9324 (1992).

Schreiber, et al., "Bis(purine) Complexes of trans-a₂Pt^II: Preparation and X-ray Structures of Bis(9-methyladenine) and Mixed 9-Methyladenine, 9-Methylguanine Complexes and Chemistry Relevant to Metal-Modified Nucelobase Triples and Quartets," *J. Am. Chem. Soc.* 118:4124-4132 (1996).

Schuhmann, W., et al., "Electron Transfer between Glucose Oxidase and Electrodes via Redox Mediators Bound with Flexible Chains to the Enzyme Surface," *J. Am. Chem. Soc.*, 113:1394-1397 (1991).

Schumm, et al., "Iterative Divergent/Convergent Approach to Linear Conjugated Oligomers by Successive Doubling of the Molecular Length: A Rapid Route to a 128 Å-Long Potential Molecular Wire," *Angew. Chem. Int. Ed. Engl.*, 33(11):1360-1363 (1994).

Sigal et al., "A Self-Assembled Monolayer for the Binding and Study of Histidine-Tagged Proteins by Surface Plasmon Resonance," *Anal. Chem.*, 68(3):490-497 (1996).

Sloop et al., "Metalloorganic labels for DNA sequencing and mapping," New. J. Chem., 18: 317-326 (1994).

Southern, et al., "Arrays of complementary oligonucleotides for analysing the hybridisation behaviour of nucleic acids," *Nucleic Acids Research*, 22(8):1368-1373 (1994).

Storhoff et al., "One-Pot Colorimetric Differentiation of Polynucleotides with Single Base Imperfections Using Gold Nanoparticles Probes," J. Am. Chem. Soc., 120:1959-1964 (1998).

Su, et al., "Interfacial Nucleic Acid Hybridization Studied by Random Primer ³²P Labelling and Liquid-Phase Acoustic Network Analysis," *Analytical Chemistry*, 66(6):769-777 (1994).

Telser, J., et al., "DNA Oligomers and Duplexes Containing a Covalently Attached Derivative of Tris(2,2'-bipyridine)ruthenium(II): Synthesis and Characterization by Thermodynamic and Optical Spectroscopic Measurements," *J. Am. Chem. Soc.*, 111:7221-7226 (1989).

Telser, J., et al., "DNA Duplexes Covalently Labeled at Two Sites: Synthesis and Characterization by Steady-State and Time-Resolved Optical Spectroscopies," *J. Am. Chem. Soc.*, 111:7226-7232 (1989).

Timofeev, E. et al., "Regioselective Immobilization of Short Oligonucleotides to Acrylic Copolymer Gel," Nucleic Acids Research, 24(16): 3142-3148 (1996).

Timofeev, E. et al., "Methidium Intercalator Inserted into Synthetic Oligonucleotides," *Tetrahedron Letters*, 37(47):8467-8470 (1996).

Tour, "Conjugated Macromolecules of Precise Length and Constitution. Organic Synthesis for the Construction of Nanoarchitectures," *Chem. Rev.*, 96:537-553 (1996).

Tour, et al., "Self-Assembled Monolayers and Multilayers of Conjugated Thiols, α-ω-Dithiols, and Thioacetyl-Containing Adsorbates. Understanding Attachments between Potential Molecular Wires and Gold Surfaces," *J. Am. Chem. Soc.*, 117:9529-9534 (1995).

Tullius, T.D. and B.A. Dombroski, "Iron(II) EDTA Used to Measure the Helical Twist Along Any DNA Molecule," *Science*, 230:679-681 (1985).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332-340 (1991).

Turro, N., et al. "Photoelectron Transfer Between Molecules Adsorbed in Restricted Spaces," *Photochem. Convers. Storage Sol. Energy, Proc. Int. Conf., 8th*, pp. 121-139 (1990).

Uosake, K., et al., "A Self-Assembled Monolayer of Ferrocenylalkane Thiols on Gold as an Electron Mediator for the Reduction of Fe(III)-EDTA in Solution," *Electrochemica Acta.*, 36(11/12):1799-1801 (1991).

Van Ness, J., et al., "A Versatile Solid Support System for Oligodeoxynucleotide Probe-Based Hybridization Assays," *Nucleic Acids Research*, 19(12):3345-3350 (1991).

Velev et al., "In Situ Assembly of Colloidal Particles into Miniaturized Biosensors," The ACS Journal of Surfaces and Colloids, Langmuir, 15(11):3693-3698 (1999).

Watson et al., "Hybrid Nanoparticles with Block Copolymer Shell Structures," J. Am. Chem. Soc., 121:462-463 (1999).

Weber, et al., "Voltammetry of Redox-Active Groups Irreversibly Adsorbed onto Electrodes. Treatment Using the Marcus Relation between Rate and Overpotential," *Anal. Chem.*, 66:3164-3172 (1994).

Williams, et al., "Studies of oligonucleotide interactions by hybridisation to arrays: the influence of dangling ends on duplex yield," *Nucleic Acids Research*, 22(8):1365-1367 (1994).

Winkler, J. R., et al., "Electron Transfer in Ruthenium-Modified Proteins," *Chem. Rev.* 92:369-379 (1992).

Xu, et al., "Immobilization and Hybridization of DNA on an Aluminum(III) Alkanebisphosphonate Thin Film with Electrogenerated Chemiluminescent Detection," *J. Am. Chem. Soc.*, 117:2627-2631 (1995).

Xu, et al., "Immobilization of DNA on an Aluminum(III) alkaneobisphosphonate Thin Film with Electrogenerated Chemiluminescent Detection," *J. Am. Chem. Soc.*, 116:8386-8387 (1994).

Yang, et al., "Growth and Characterization of Metal(II) Alkaneobisphosphonate Multilayer Thin Films on Gold Surfaces," *J. Am. Chem. Soc.*, 115:11855-11862 (1993).

Yershov, G. et al., "DNA Analysis and Diagnostics on Oligonucleotide Microchips," Proc. Natl. Acad. Sci. USA, 93:4913-4918 (1996).

Zhou, et al., "Fluorescent Chemosensors Based on Energy Migration in Conjugated Polymers: The Molecular Wire Approach to Increased Sensitivity," *J. Am. Chem. Soc.*, 117:12593-12602 (1995).

Boon et al., "Mutation Detection by Electrocatalysis at DNA-Modified Electrodes," Nature Biotechnology, 18: 1096-1100 (Oct. 2000).

Hess et al., "Base Pairing Properties of Novel Transition Metal PNA Conjugates," Journal of Inorganic Biochemistry, 74:161 (1999).

Mucic et al., "Synthesis and Characterization of DNA with Ferrocenyl Groups Attached to their 5'-Termini: Electrochemical Characterization of a Redox-Active Nucleotide Monolayer," *Chem. Commun.*, pp. 555-557 (1996).

Anne, A., et al., "Synthesis of first ferrocene labeled dideoxynucleotide and its use for 3' redox end-labeling of 5' modified single stranded oligonucleotides," *Bioconjug. Chem.* 12(3):396-405 (May-Jun. 2001).

Codington, J.F., et al., "Nucleosides. XIII. Synthesis of 3'-Amino-3'-deoxy-arabinosyl-uracil via 2', 3'-Epoxy-lyxosyl Nucleosides," *J. Org. Chem.* 27(1):163-167 (Jan. 1962).

Conway, N.E., et al., "Site-specific attachment of labels to the DNA backbone," in *Oligonucleotides and Analogues: A Practical Approach*, 211-239, Eckstein, F. (ed.), IRL Press: Oxford, GB (1991).

Dwyer, T., et al., "Structural Analysis of Covalent Peptide Dimers, Bix(pyridine-2-carboxamidonetropsin) (CH2) 3-6, in Complex with 5'-TGACT-3' Sites by Two Dimensional NMR," *J. Am. Chem. Soc.* 115(22):9900-9906 (1993).

Gait, M.J., "Oligoribonucleotide Synthesis," in *Oligonucleotides and Analogues: A Practical Approach*, 25-48, Eckstein, F. (ed.), IRL Press: Oxford, GB (1991).

Gilles, P.N., et al., "Single nucleotide polymorphic discrimination by an electronic dot blot assay on semiconductor microchips," *Nat. Biotechnol.* 17(4):365-370 (Apr. 1999).

Glover, D., et al., "Alternating current Polarography in the Harmonic Multiplex Mode," *Anal. Chem.* 45(11):1869-1877 (Sep. 1973).

Kirschenheuter, G., et al., "An Improved Synthesis of 2'-Azido-2'-Deoxyuridine," *Tet. Lett.* 35(46):8517-8520 (1994).

Krider, E.S., et al., "Electron transfer in DNA: covalent attachment of spectroscopically unique donor and acceptor complexes," *JBIC* 3:222-225 (1998).

Krider, E.S., et al., "Automated Synthesis of 3' Metalated Oligonucleotides," *Inorg. Chem.* 40(16):4002-4009 (Jul. 2001).

Kumar, A., et al., "A Simple Method for Introducing—SH/COOH Group at 5'-CH end of Oligonucleotide," *Nucleosides Nucleotides* 11(5):999-1002 (1992).

Liu, R., et al., "Passive mixing in a three-dimensional serpentine microchannel," *J. Microelectromechanical Systems* 9(2):190-196 (Jun. 2000).

Mengel, R., et al., "A Simple Synthesis of 2'-Deoxy-2'-flurocytidine by Nucleophilic Substitution of 2,2-Anhydrocytidine with Potassium Fluoride/Crown Ether," *Agnew. Chem. Intl. Ed. Engl.* 17(7):525 (1978).

Millan, K.M., et al., "Sequence-Selective Biosensor for DNA Based on Electroactive Hybridization Indicators," *Anal. Chem.* 65(17):2317-2323 (Sep. 1993).

Miller, N., et al., "Nucleosides. XXI. Synthesis of Some 3'-Substituted 2',3'-Dideoxyribonucleosides of Thymine and 5-Methylcytosine," *J. Org. Chem.* 29:1772-1776 (Jul. 1964).

Mitsui, T., et al., "Coumarin-fluorescein pair as a new donor-acceptor set for fluorescence energy transfer study of DNA," *Tet. Lett.* 41(15):2605-2608 (2000).

Napier, M., et al., "Probing biomolecule recognition with electron transfer: electrochemical sensors for DNA hybridization," *Bioconjug. Chem.* 8(6):906-913 (Nov.-Dec. 1997).

O'Donnell-Maloney, M., et al., "The development of microfabricated arrays for DNA sequencing and analysis," *Trends Biotechnol.* 14(10):401-407 (Oct. 1996).

Pieken, W.A., et al., "Kinetic Characterization of Ribonuclease-Resistant 2'-Modified Hammerhead Ribozymes," *Science* 253(5017):314-317 (Jul. 1991).

Sebesta, D., et al., "2'-Deoxy-2'-Alkoxyaminouridines: Novel 2'-Substituted Uridines prepared by Intramolecular Nucleophilic Ring Opening of 2,2'-O-Anydrouridines," *Tetrahedron* 52(46):14385-14402 (Nov. 1996).

Sinha, N.D., et al., "Oligonucleotides with reporter gropus attached to the 5'-Terminus," in *Oligonucleotides and Analogues. A Practical Approach*, 185-210, Eckstein, F. (ed.), IRL Press: Oxford, GB (1991).

Sproat, B.S., et al., "2-O-Methyloligoribonucleotides: synthesis and applications," in *Oligonucleotides and Analogues: A Practical Approach*, 211-239, Eckstein, F. (ed.), IRL Press: Oxford, GB (1991).

Uto, Y., et al., "Electrochemical analysis of DNA amplified by the polymerase chain reaction with a ferrcenylated oligonucleotide," *Anal. Biochem.* 250:122-124 (1997).

Verheyden, J.P.H., et al., "Synthesis of some pyrimidine 2'-amino-2'-deoxynucleosides," *J. Org. Chem.* 36(2):250-254 (1971).

Xi, Z., et al., "New Stereocontrolled Synthesis of Isomeric C-Branched ββ-D-Nucleosides by Intramolecular Free-Radical Cyclization-Opening Reactions Based on Temporary Silicon Connection," *Tetrahedron* 48(2):349-370 (1992).

Yu, C., et al., "2' ribose ferrocene oligonucleotides for electronic detection of nucleic acids," *J. Org. Chem.* 66(9):2937-2942 (May 2001).

Zimmerman, R., et al., "DNA stretching on functionalized gold surfaces," *Nucleic Acids Res.* 22(3):492-497 (Feb. 1994).

Burns, M., et al., "An integrated nanoliter DNA analysis device," *Science* 282(5388):484-487 (Oct. 1998).

Cullison, J., et al., "Cyclic voltammetry with harmonic lock-in detection: applications to flow systems," *Electroanalysis* 8(4):314-319 (Apr. 1996).

Hall, D., et al., "Sensitivity of DNA-mediated electron transfer to the intervening π-stack: a probe for the integrity of the DNA base stack," *J. Am. Chem. Soc.* 119(21):5045-5046 (May 1997).

Herne, T.M., et al., "Characterization of DNA probes immobilized on gold surfaces," *J. Am. Chem. Soc.* 119(38):8916-8920 (Sep. 1997).

Laibinis, P., et al., "Orthogonal self-assembled monolayers: alkanethiols on gold and alkane carboxylic acids on alumina," *Science* 245:845-847 (Aug. 1989).

Liu, S., et al., "Voltammetric determination of sequence-specific DNA by electroactive intercalator on graphite electrode," *Anal. Chim. Acta* 335(3):239-243 (Dec. 1996).

Mikkelsen, S., "Electrochemical Biosensors for DNA Sequence Detection," *Electroanalysis* 8(1):15-19 (1996).

Smalley, J., et al., "Kinetics of electron transfer through ferrocene-terminated alanethiol monolayers gold," *J. Phys. Chem.* 99(35):13141-13149 (Aug. 1995).

Welch, T., et al., "Distribution of metal complexes bound to DNA determined by normal pulse voltammetry," *J. Phys. Chem.* 100(32):13829-13836 (Aug. 1996).

Rickert, J., et al., "A 'mixed' self-assembled monolayer for an impedimetric immunosensor," *Biosens. Bioelect.* 11(8):757-768 (1996).

Steel, A., et., "Electrochemical quantitation of DNA immobilized on gold." *Anal. Chem.* 70(22): 4670-4677 (Nov. 1998).

\* cited by examiner

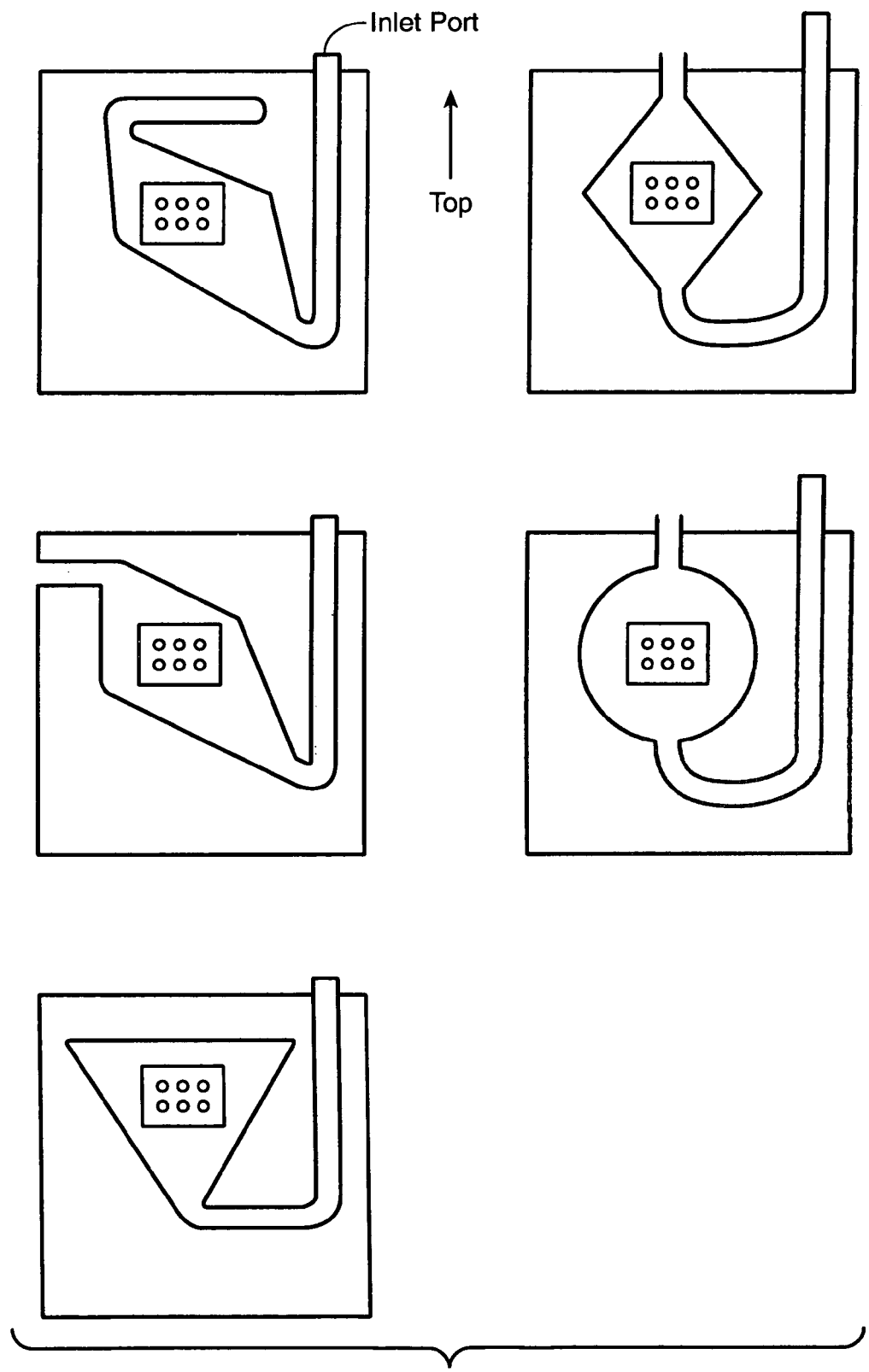
FIG._1

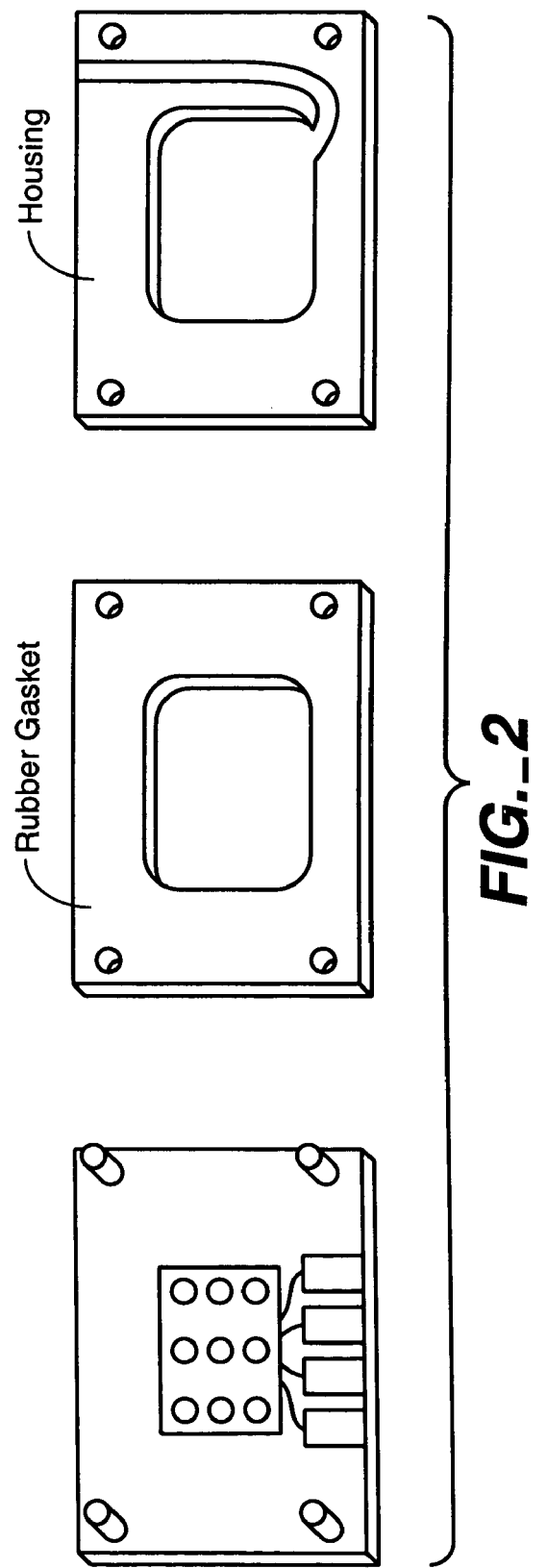
FIG._2

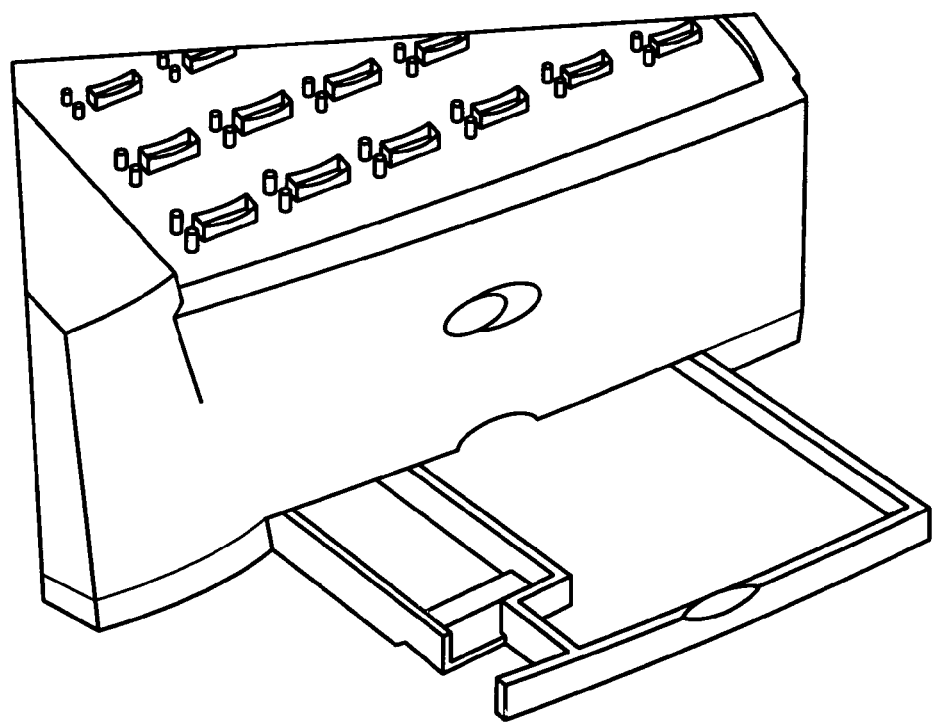
FIG._3A
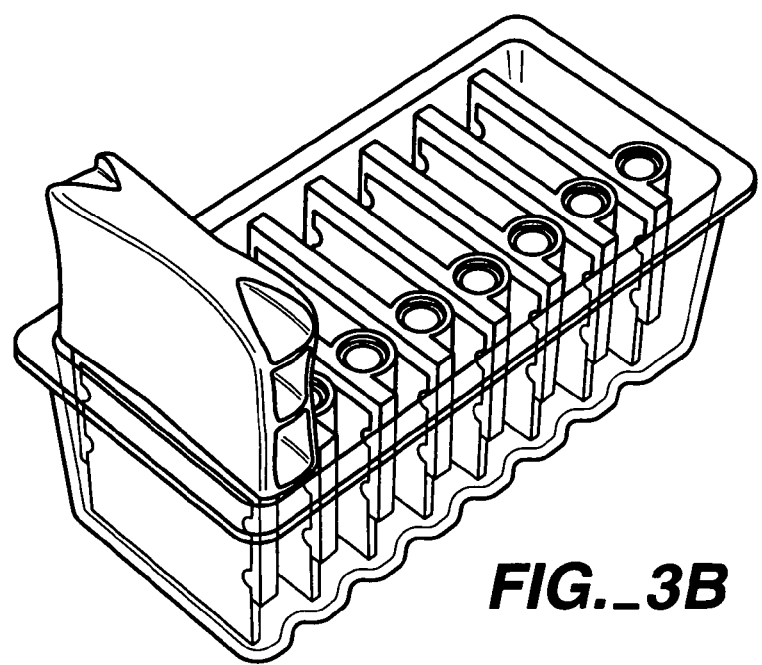
FIG._3B

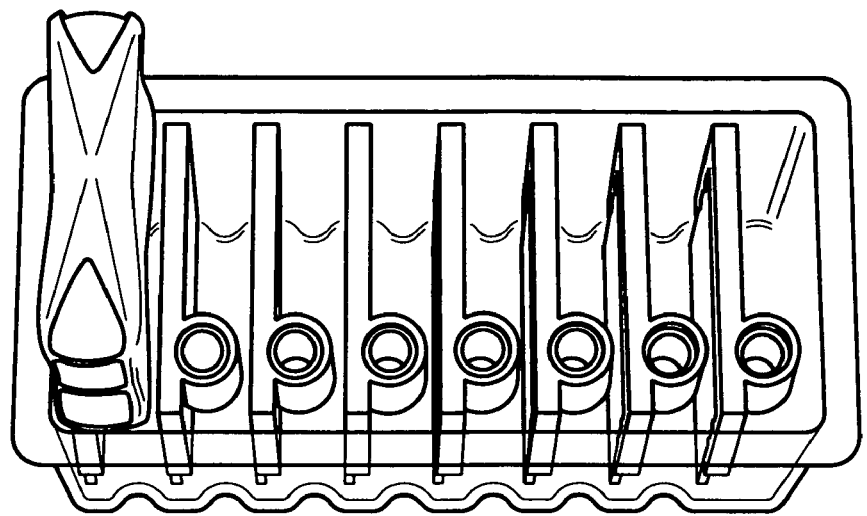
FIG._3C
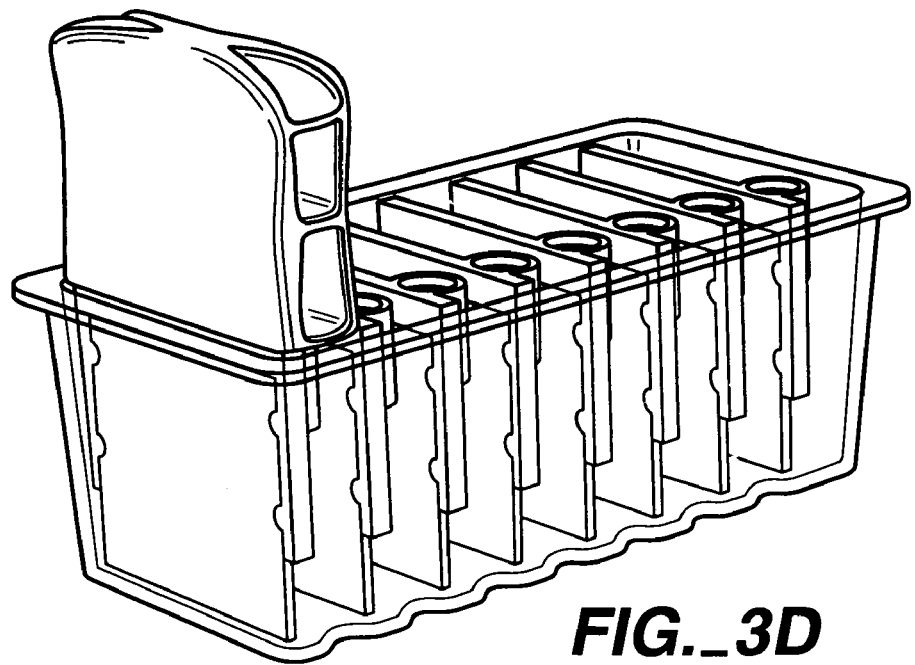
FIG._3D

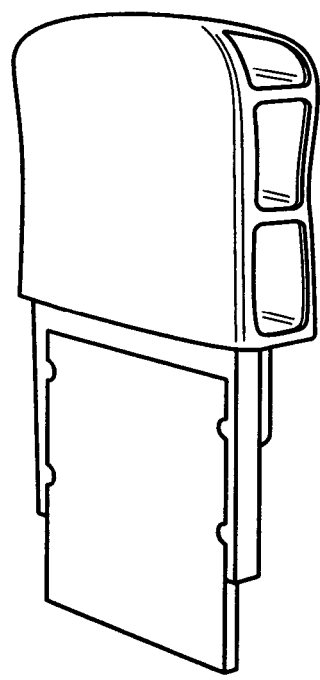 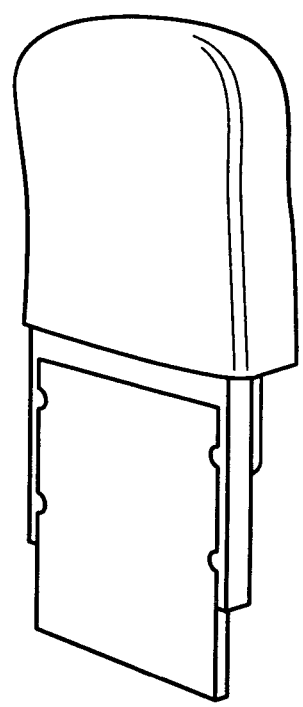
FIG._3E     FIG._3F
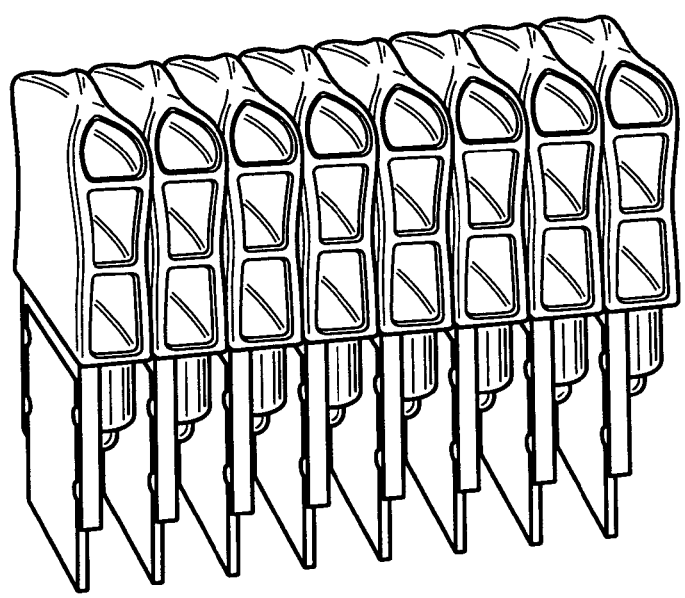
FIG._3G

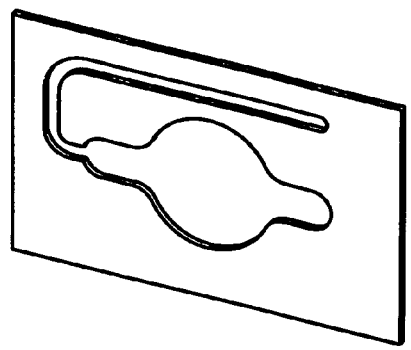
FIG._4A
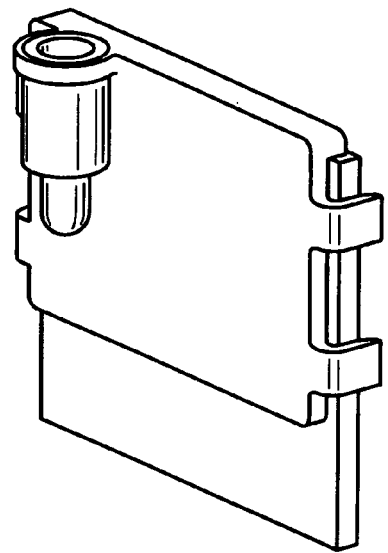
FIG._4B
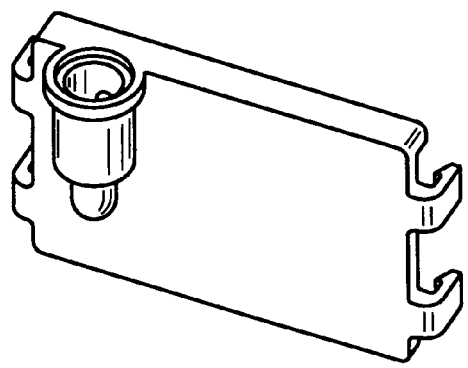
FIG._4C
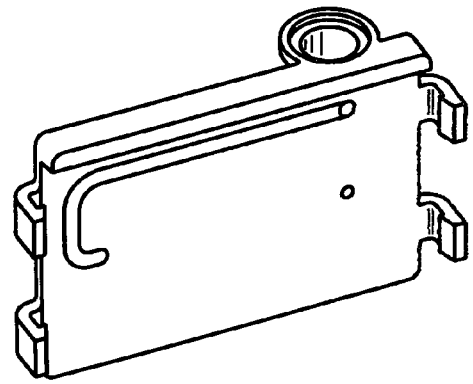
FIG._4D

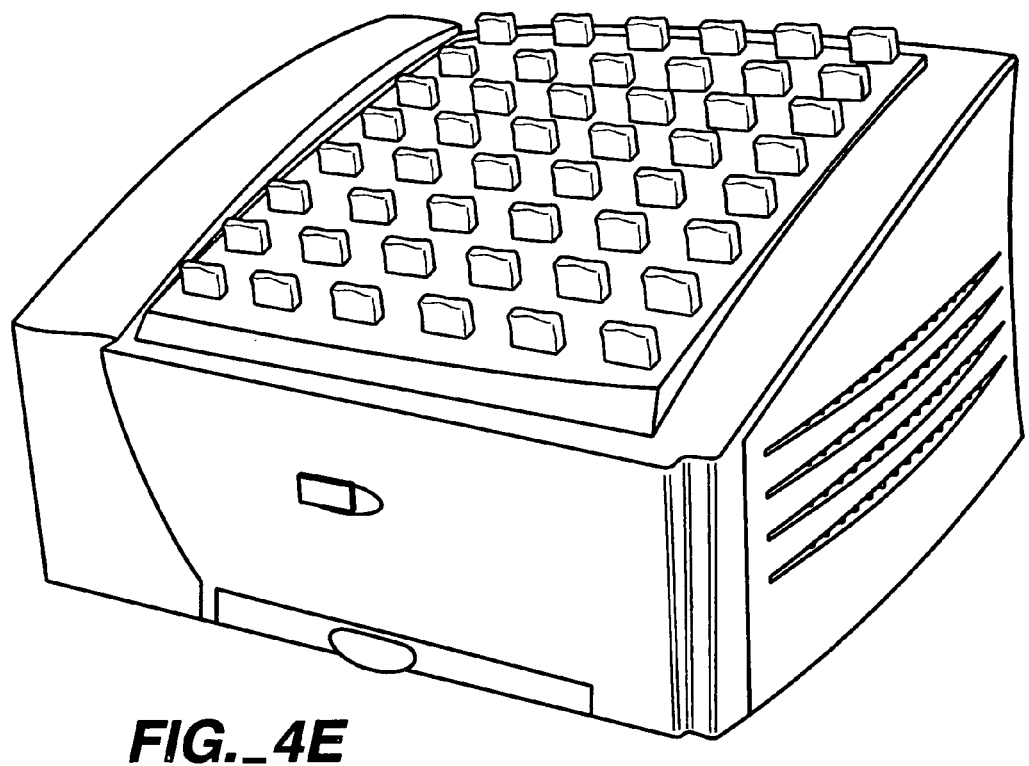
FIG._4E
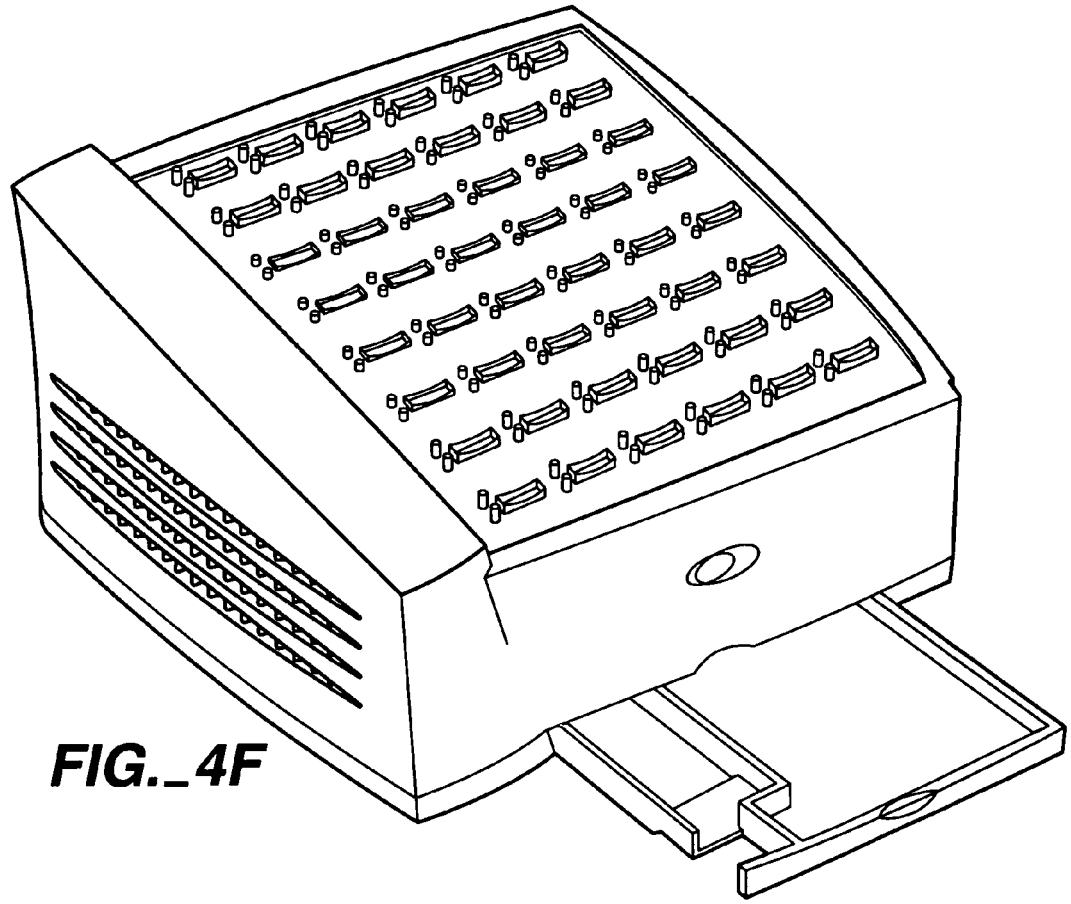
FIG._4F

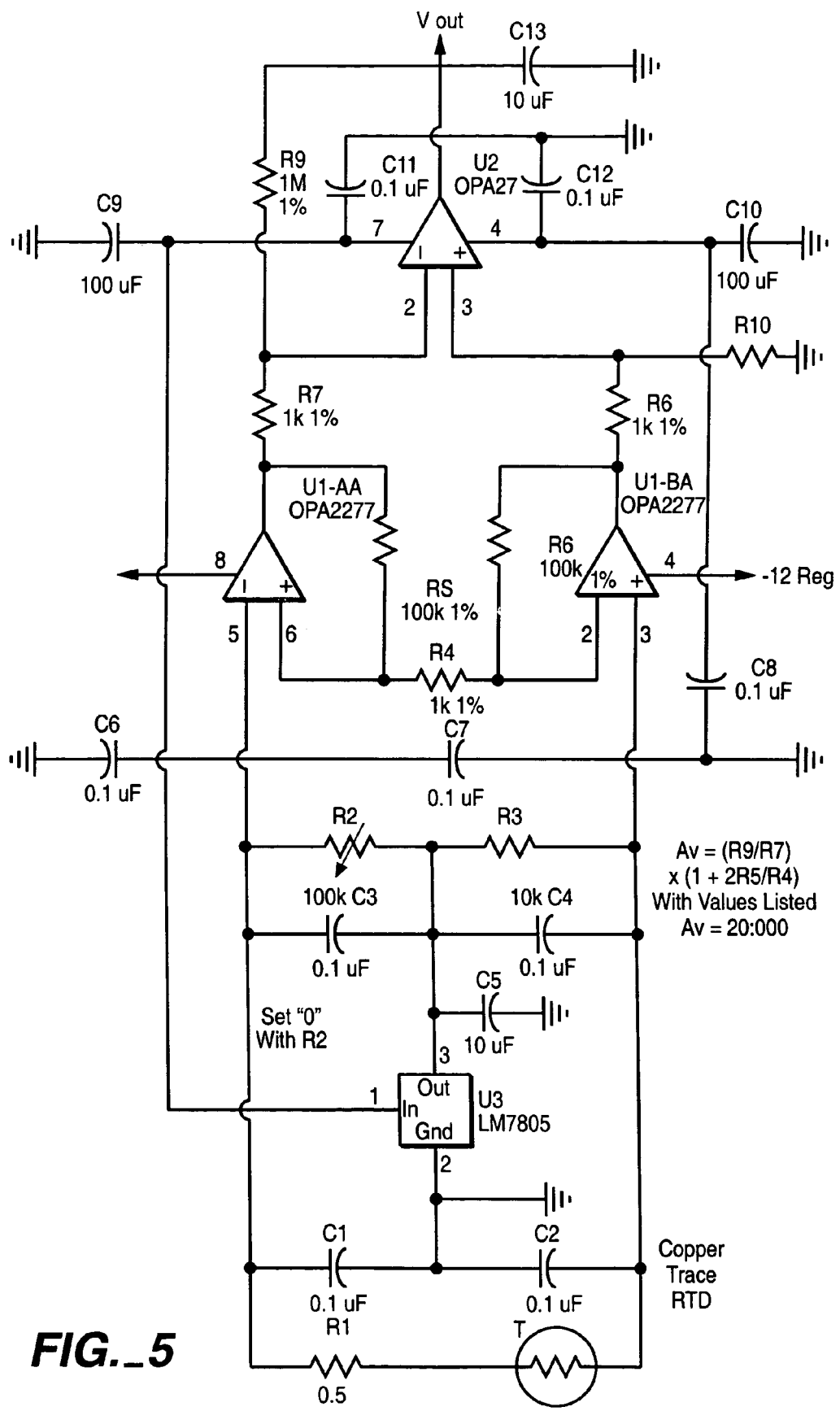
FIG._5

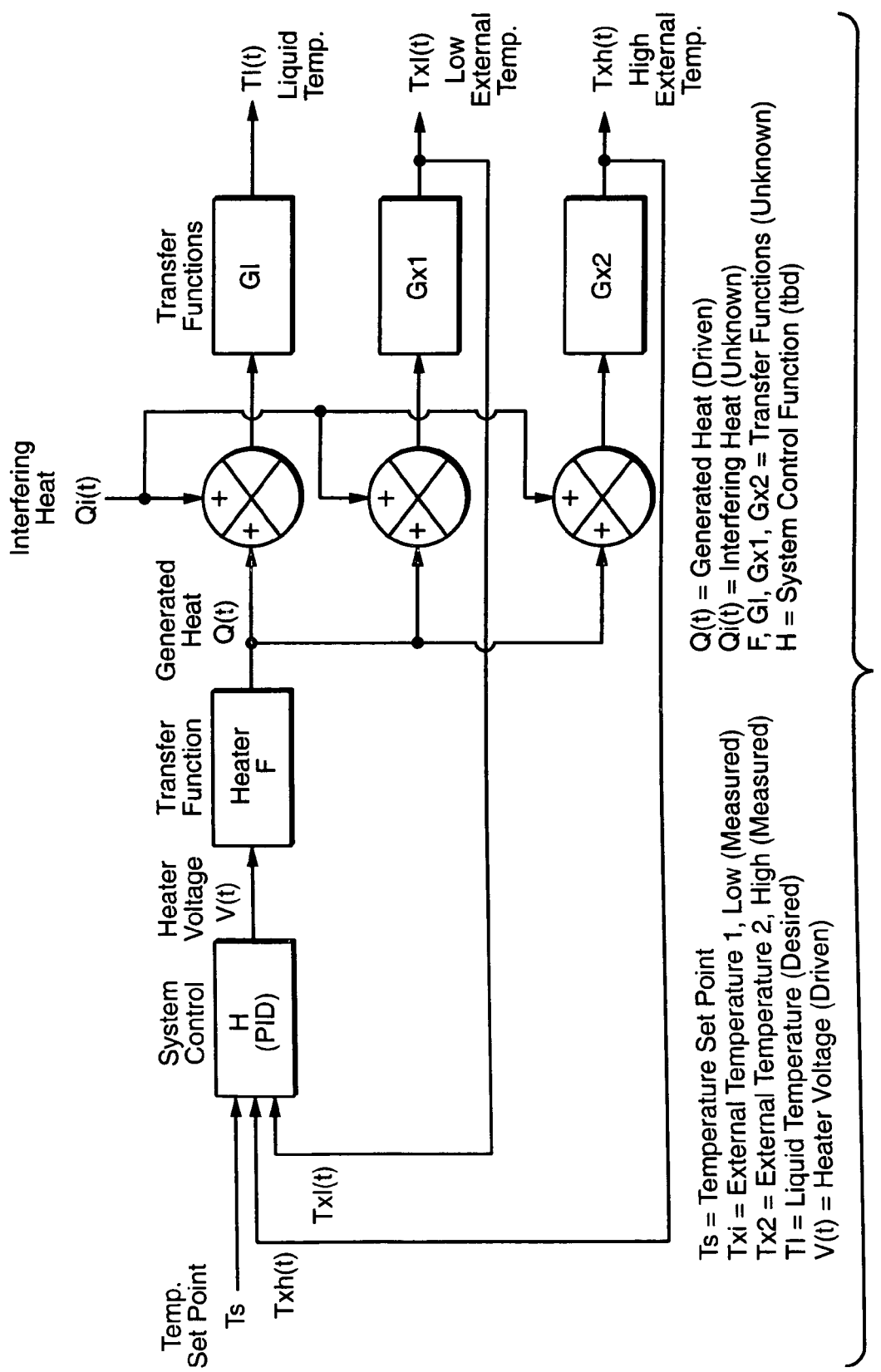
FIG._6

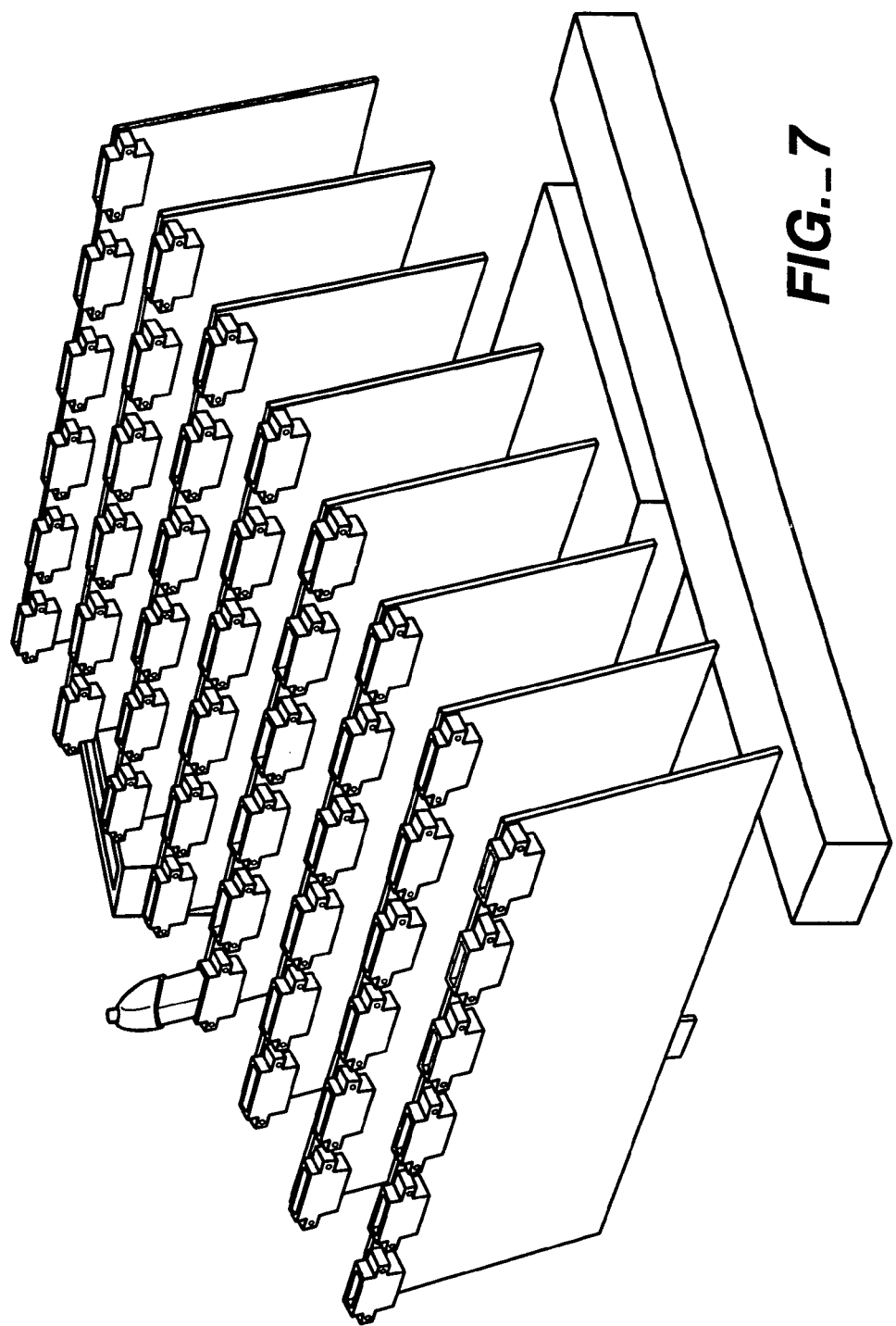
FIG._7

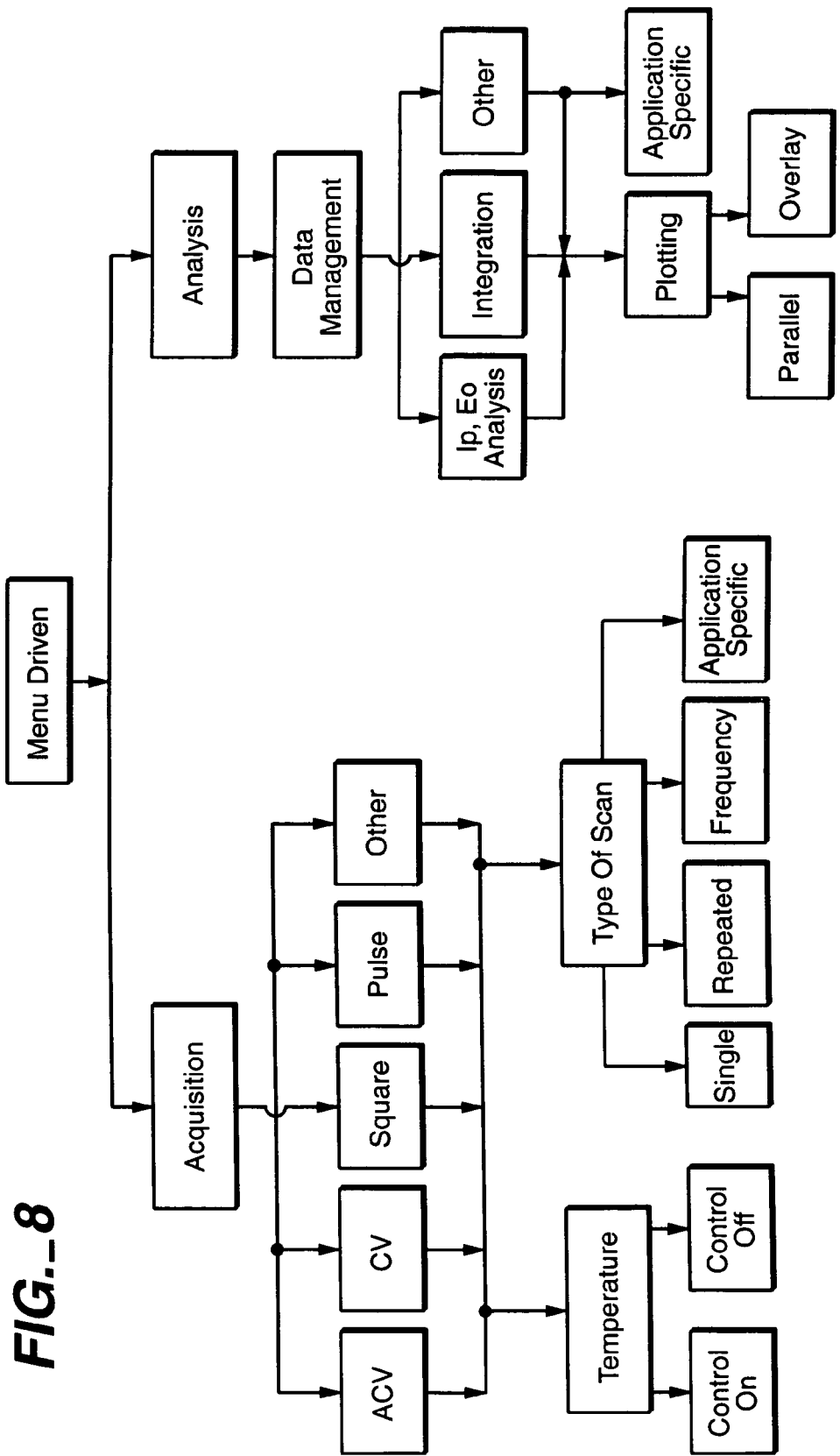
FIG._8

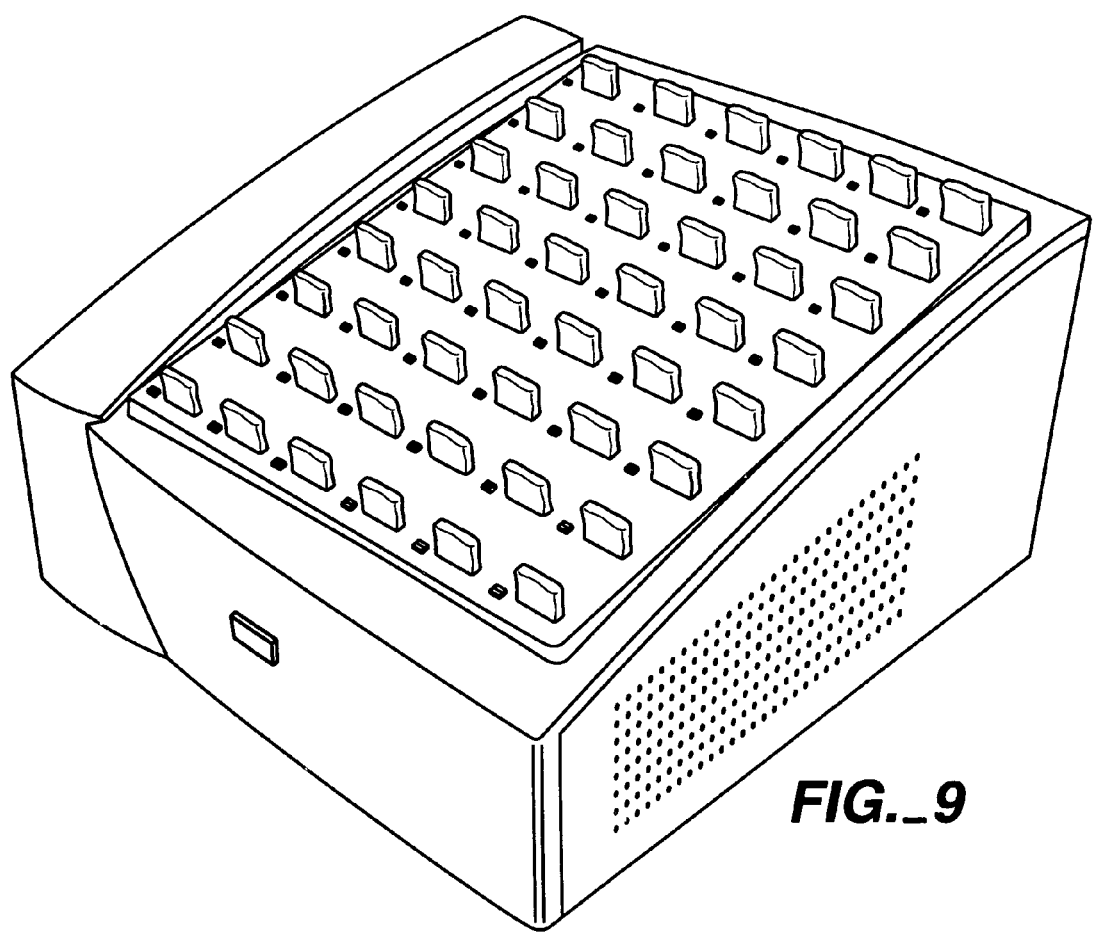
FIG._9

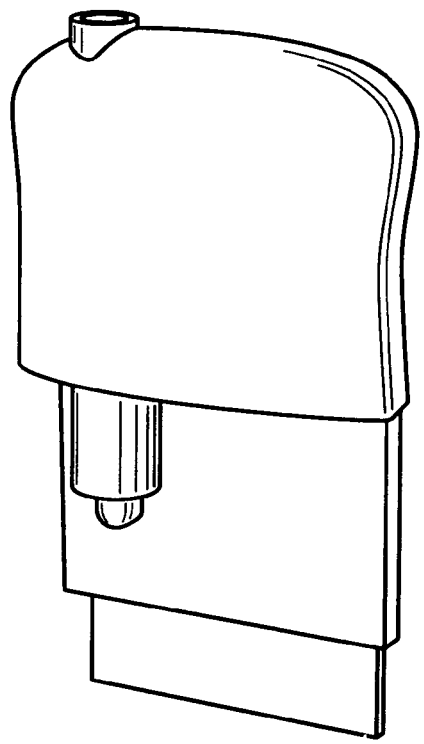
FIG._10A
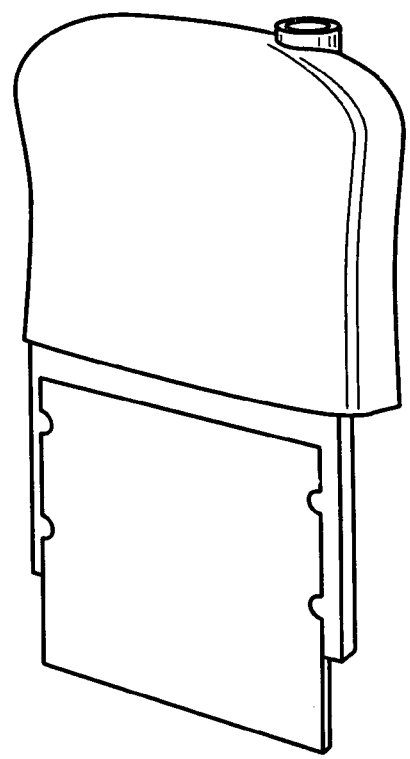
FIG._10B

- Bar coded "reference" sheet, stored in tray under unit, with bar coded protocols, bar coded well and slot id's, bar coded commands (e.g. "cancel", "done", etc.)
- Standard bar code wand (preferably with built-in decoder), housed in the tray (hence hidden when not in use)
- Serial (RS-232/485) interface (preferred), or "keyboard wedge"
- Multi-code support (Code 39, Code 128, etc.)
- Bar code on chip carrier (1 code per "8 pack"), identifying test, batch, etc.
  - Peel off labels, with same code as on carrier, with each "8 pack"

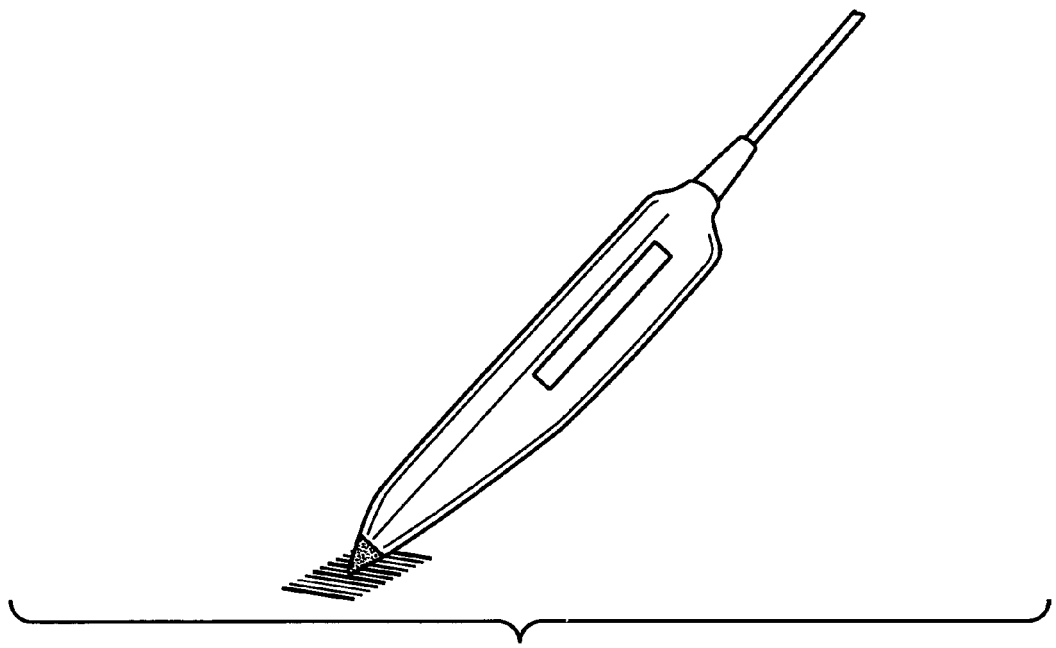

FIG._11

- Bar code usage scenario
    - User fills "8-pack" (all 8, or partially) from a 96 well plate, or from individual sample containers (PCR tubes, vaccutainers, etc.)
    - Pull out tray (with bar code reference sheet) and grab wand
    - Scan "start" code
    - Scan protocol code from sheet (will remain in effect until "done" is scanned)
    - Scan chip code from carrier (will remain in effect until "done" is scanned)
    - For each cartridge, user will
        - insert the cartridge in an open slot. Unit senses new chip automatically
        - scan the sample ID by either
            - scanning 96 well plate bar code from plate and well code from sheet
            - or scanning unique sample ID from container
            - or scanning "no ID" from reference sheet
    - Scan "done" code. The protocol can' now be started on these cartridges

FIG._12

- Bar code concept benefits
    - No keyboard entry (all-routine setup can be entered via bar coding)
    - All routine entries accomplished while in front of unit (no going back & forth between PC & Hydra)
    - All bar code entries done from small, flat surface in front of unit
    - No need to label each chip or each slot (which would compromise appearance)
    - Uses small unobtrusive bar code wand, hidden when not in use
    - Is flexible with respect to sample container (tube, 96 well plate, etc.), chip usage (by row of 8, or by individual chip), and lab bar coding method

FIG._13

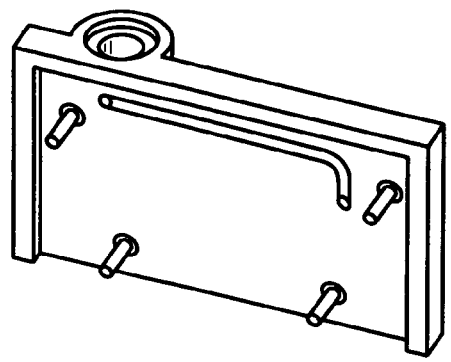
FIG._14A
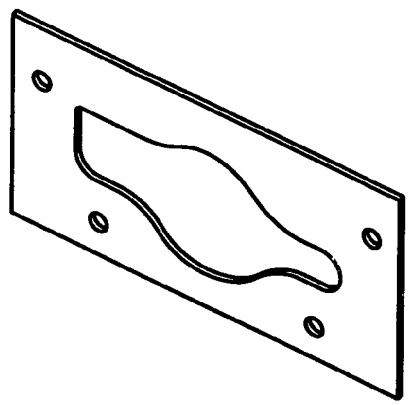
FIG._14B
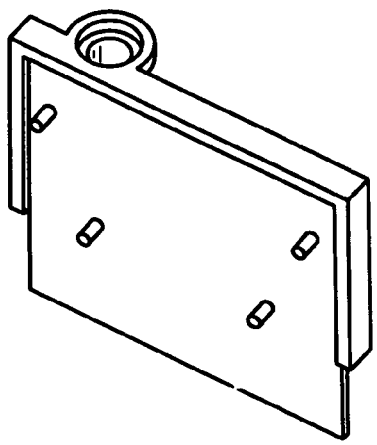
FIG._14C
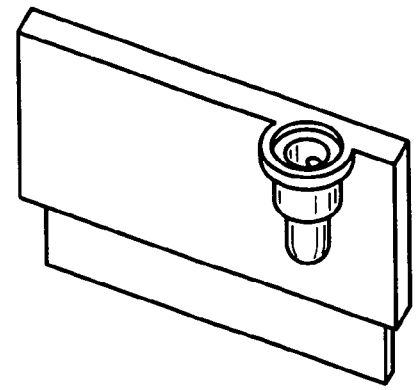
FIG._14D

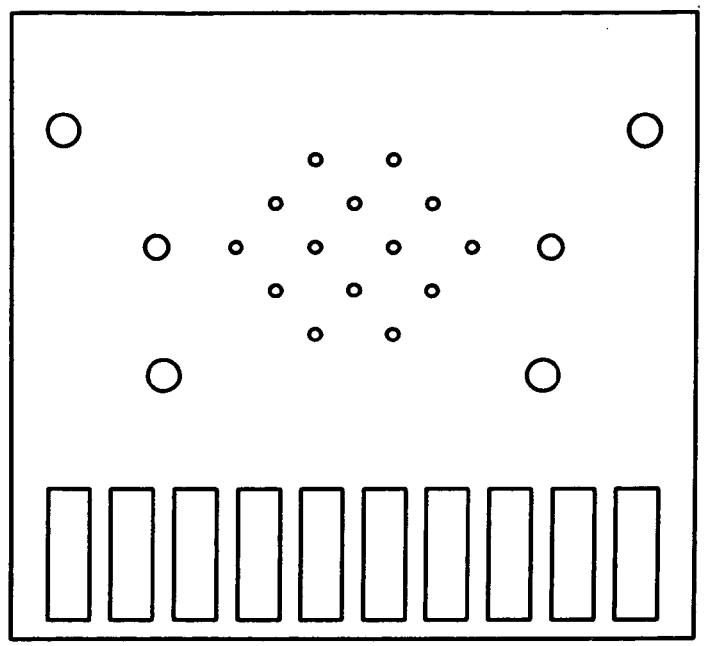
FIG._14E
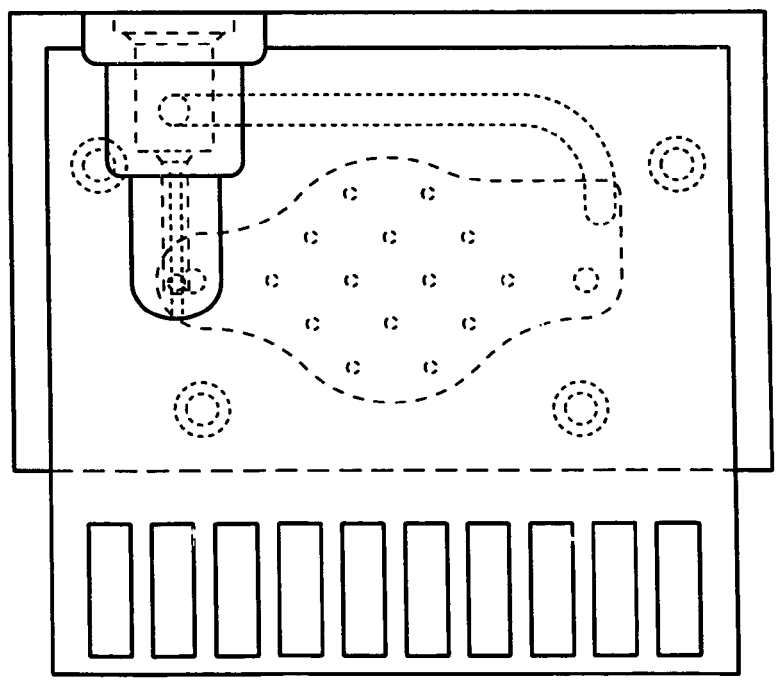
FIG._14F

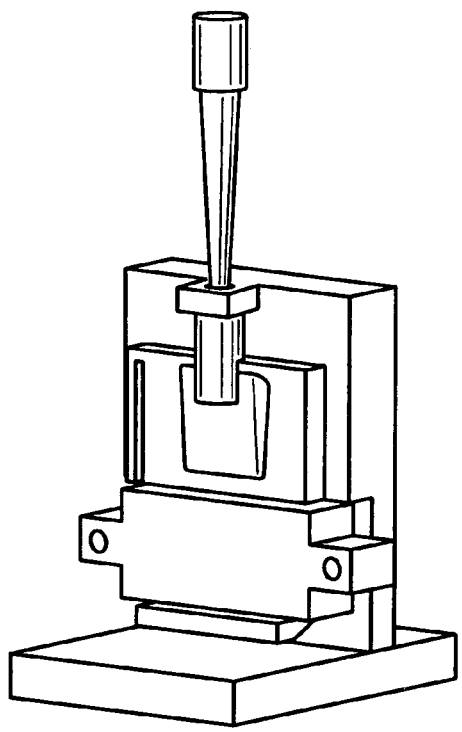
FIG._15A
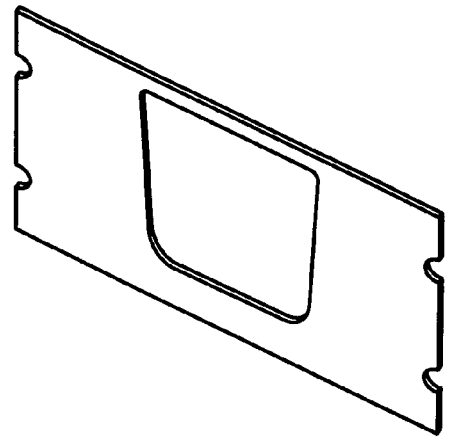
FIG._15B
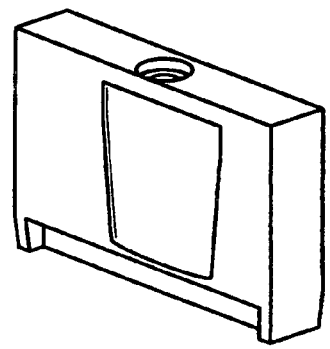
FIG._15C
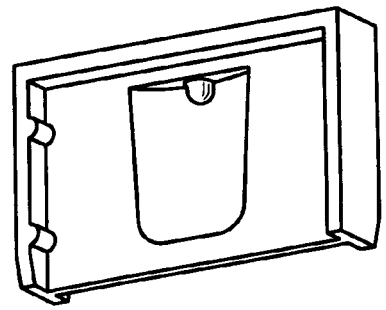
FIG._15D

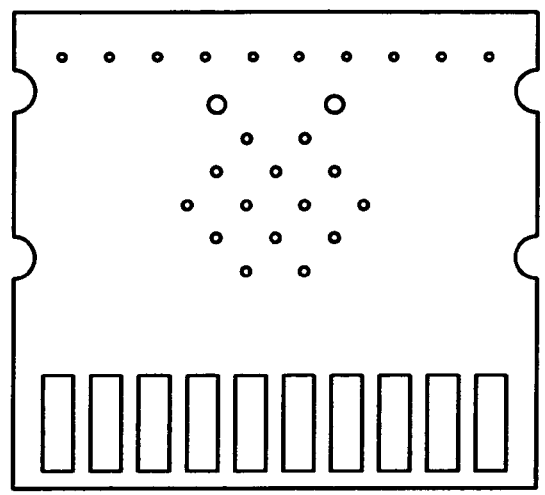
FIG._15E
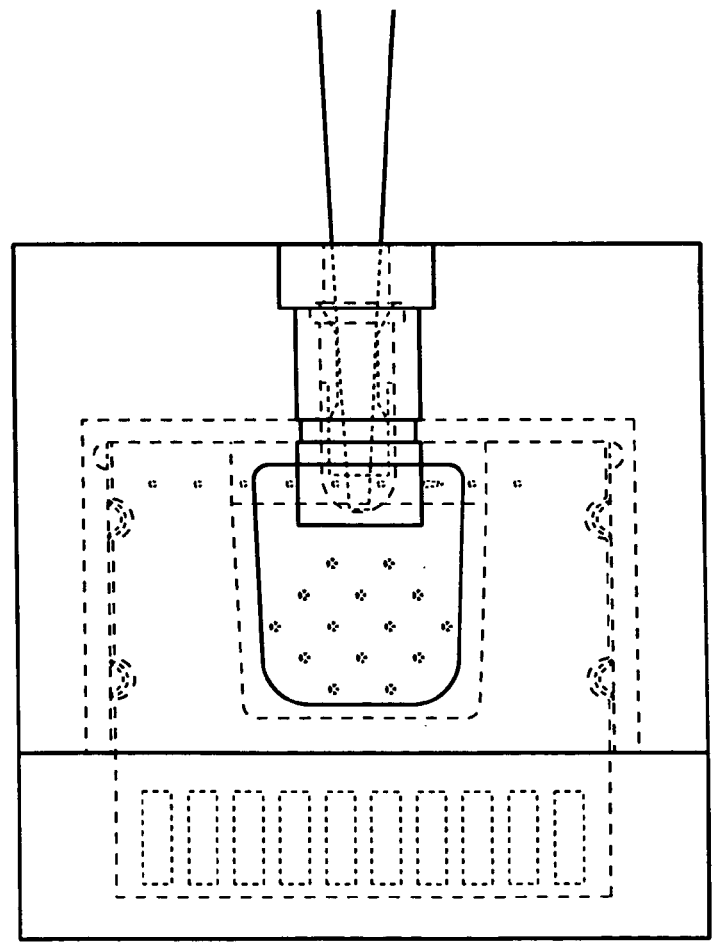
FIG._15F

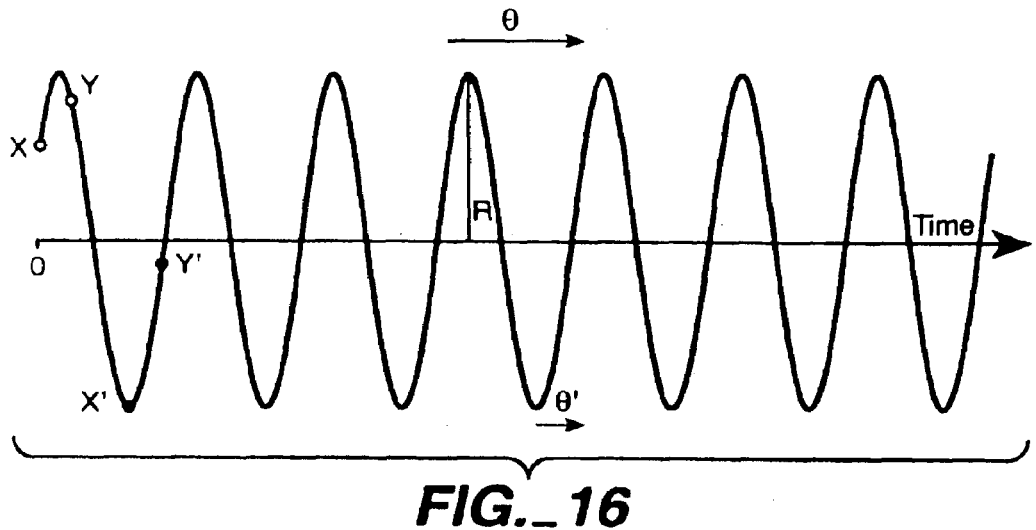
FIG._16
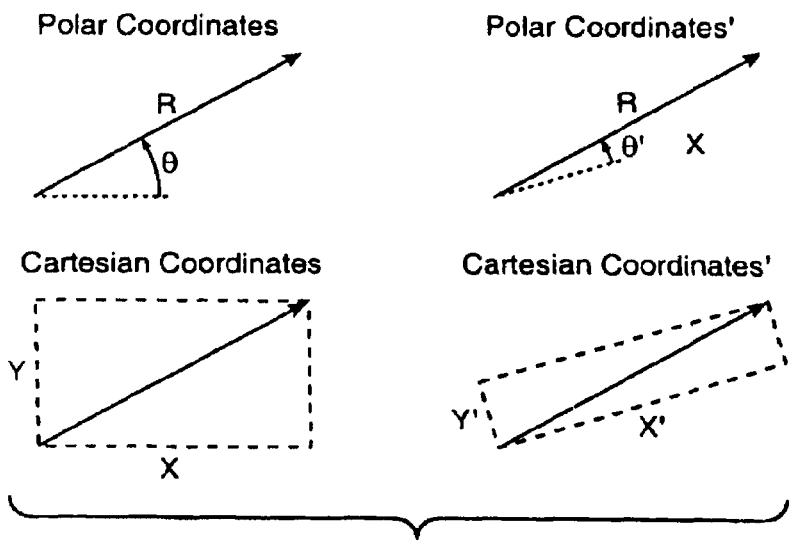
FIG._17

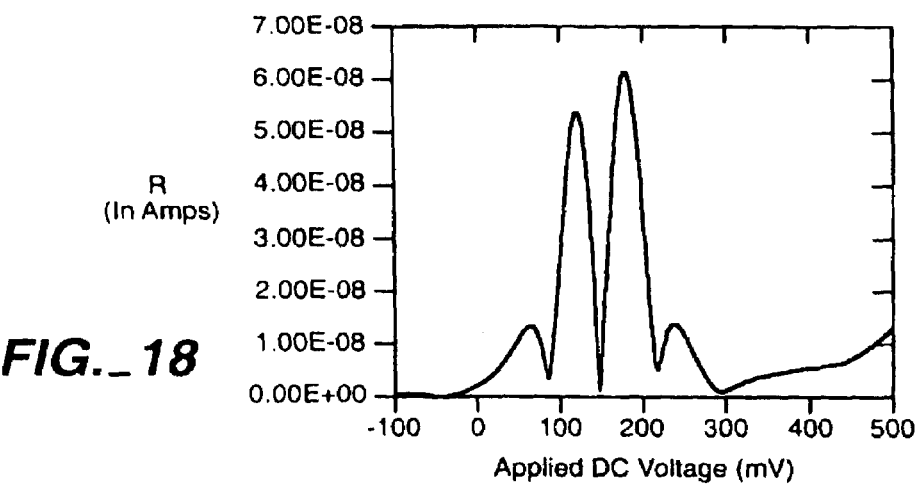
FIG._18
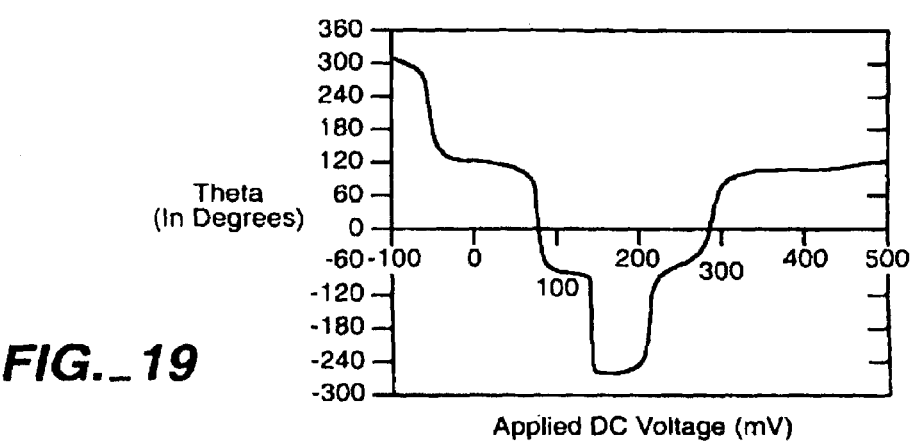
FIG._19
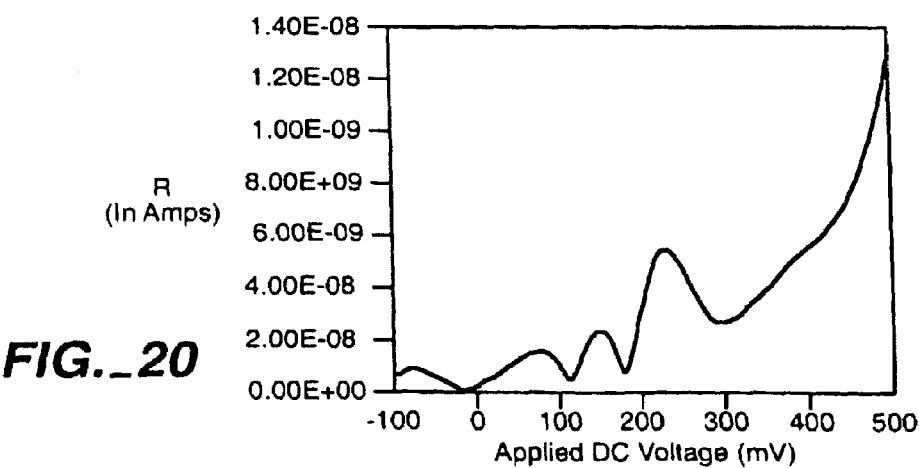
FIG._20

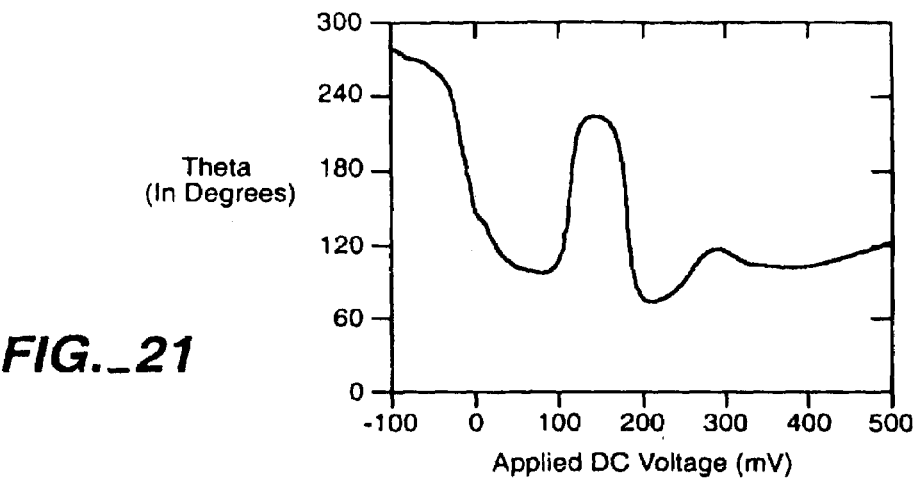
FIG._21
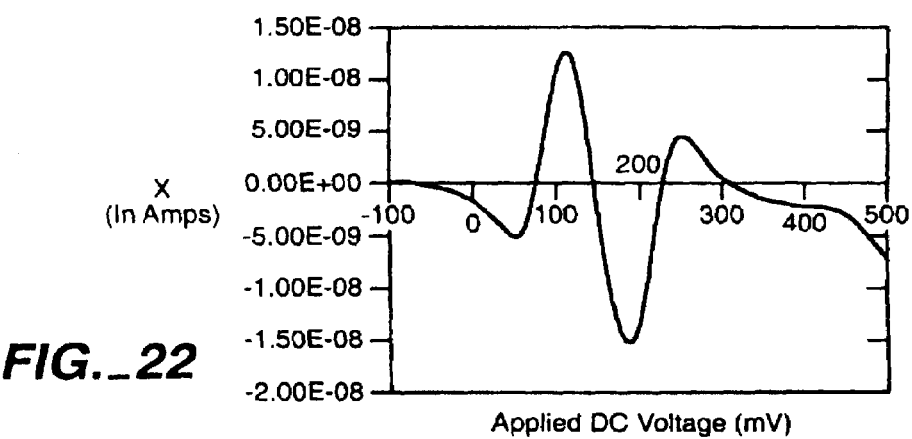
FIG._22
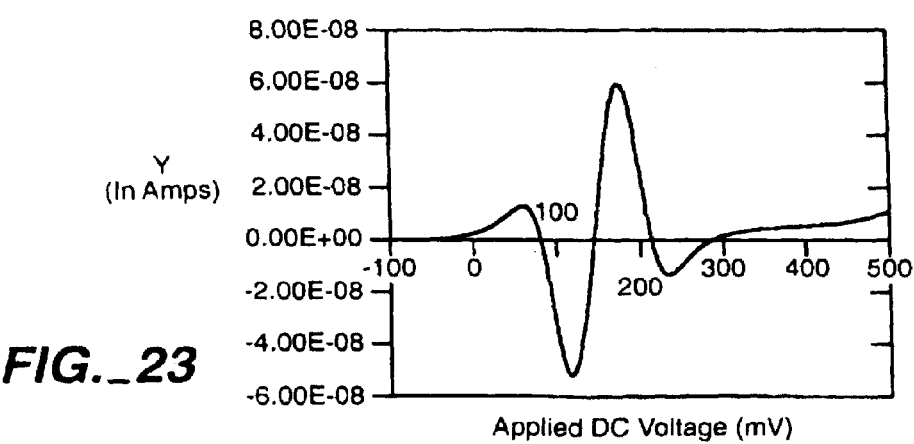
FIG._23

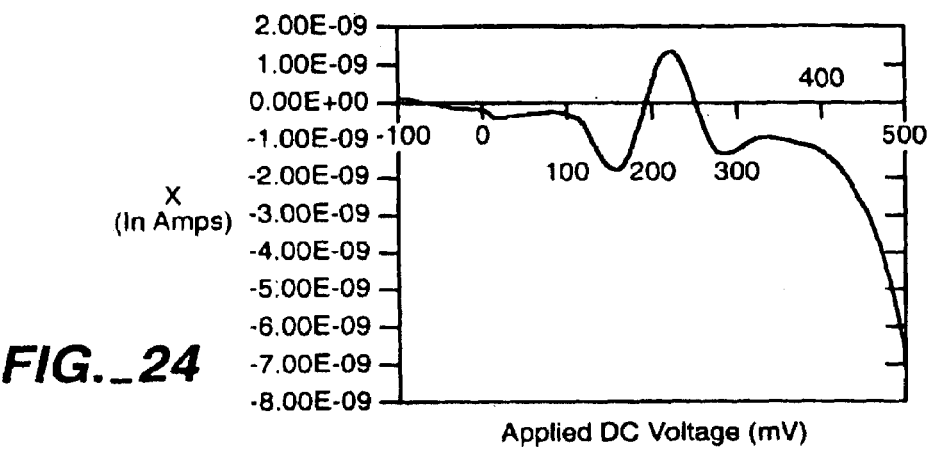
FIG._24
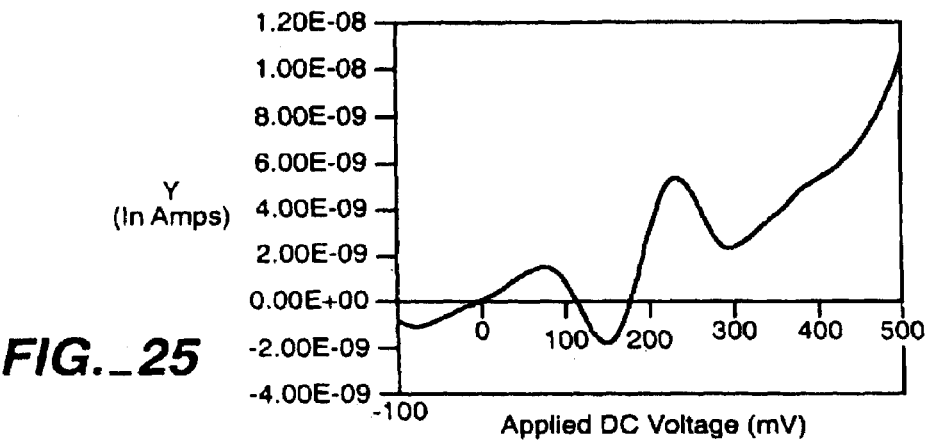
FIG._25

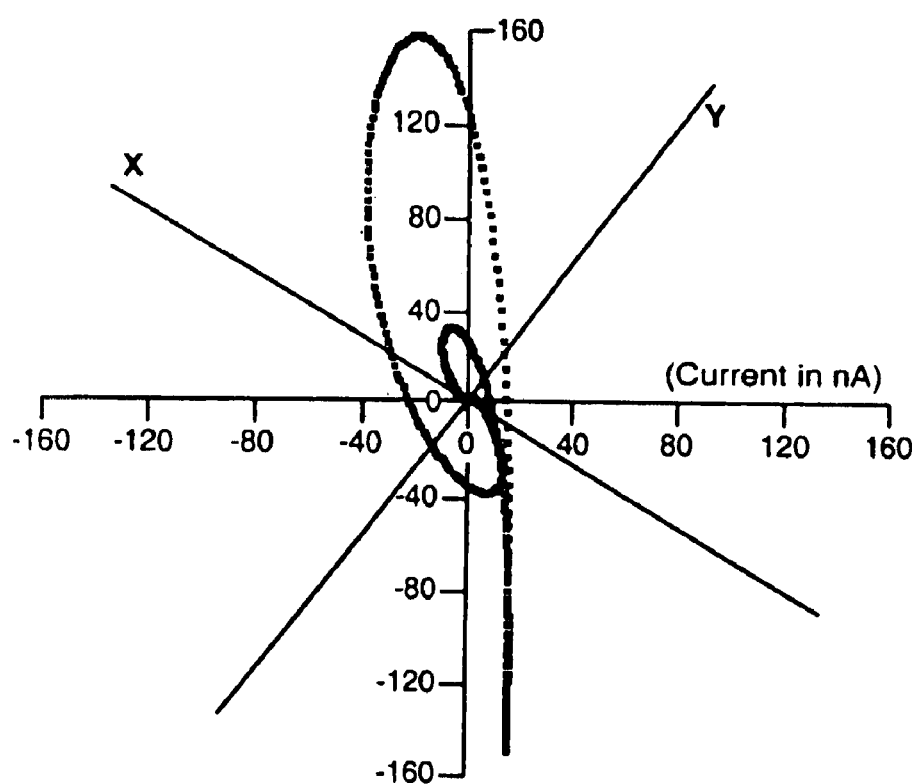
FIG._26

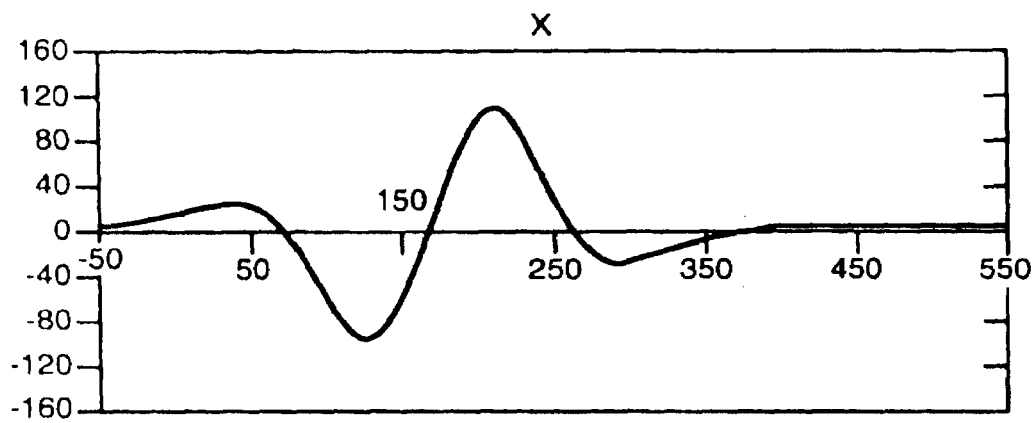
FIG._27
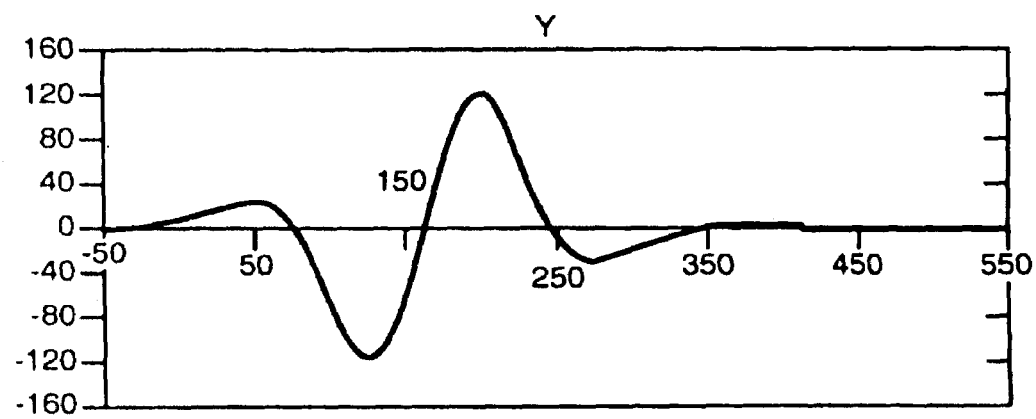
FIG._28
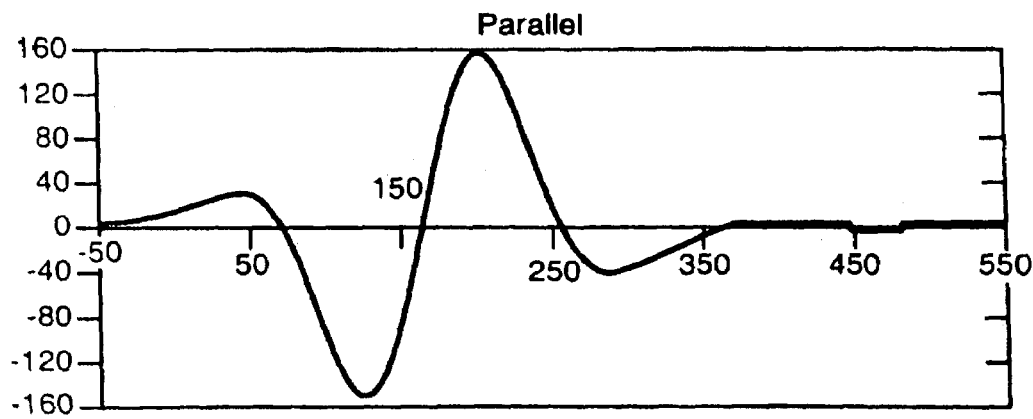
FIG._29

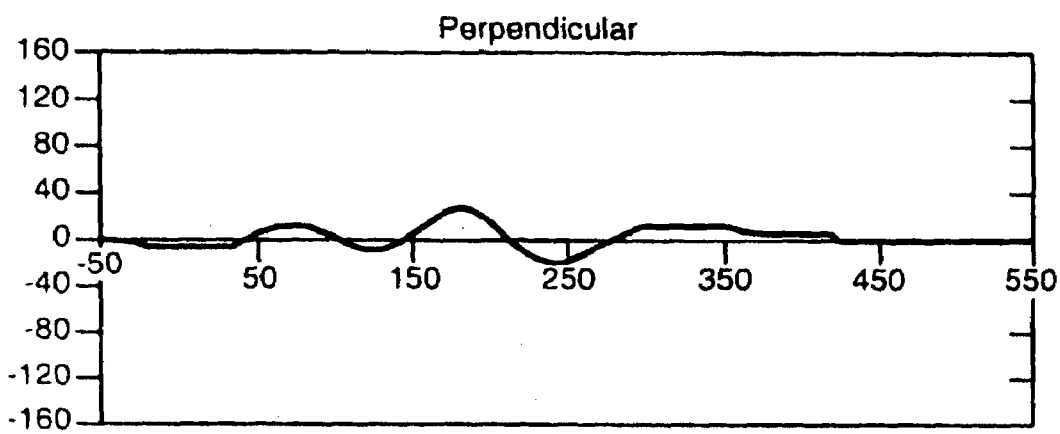
FIG._30
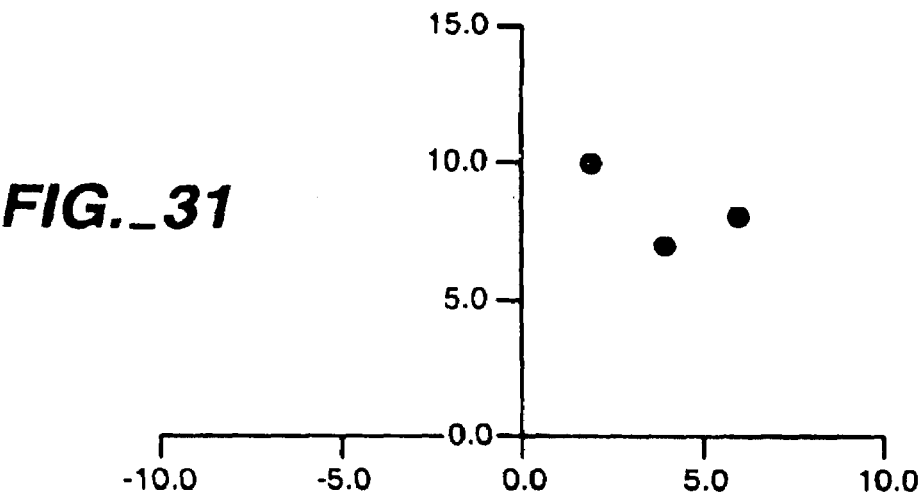
FIG._31
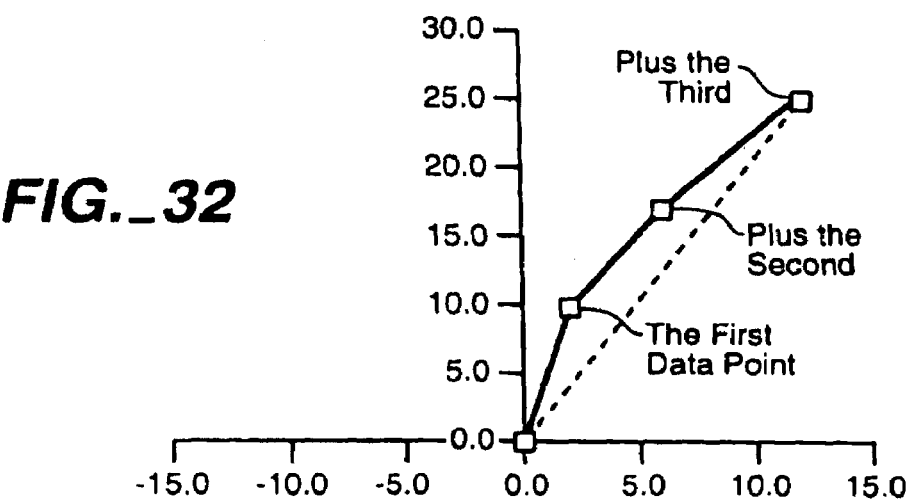
FIG._32

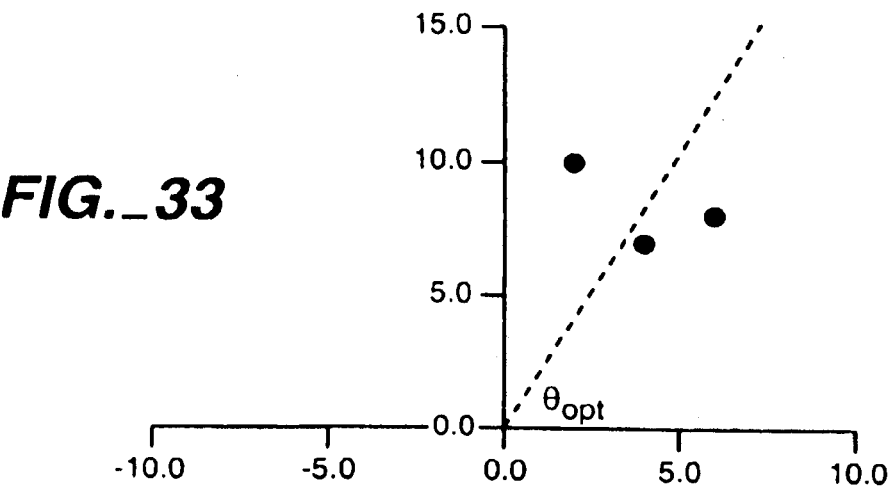
FIG._33
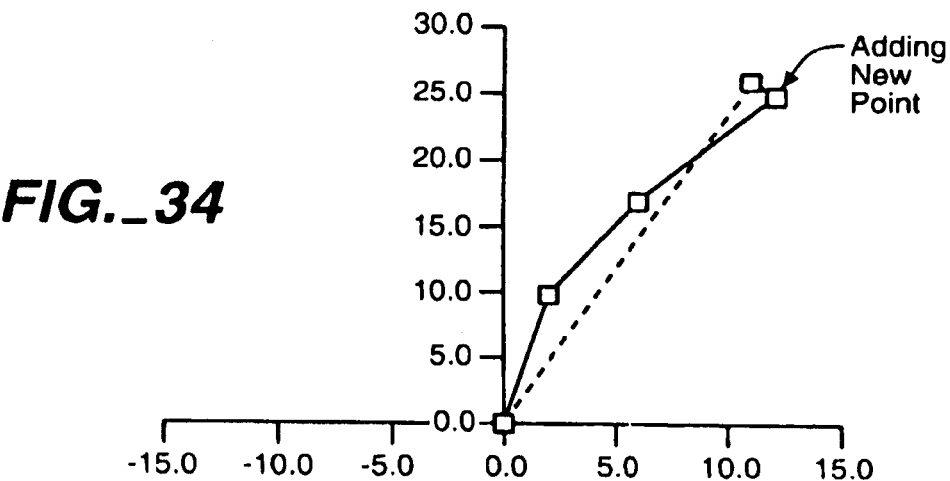
FIG._34
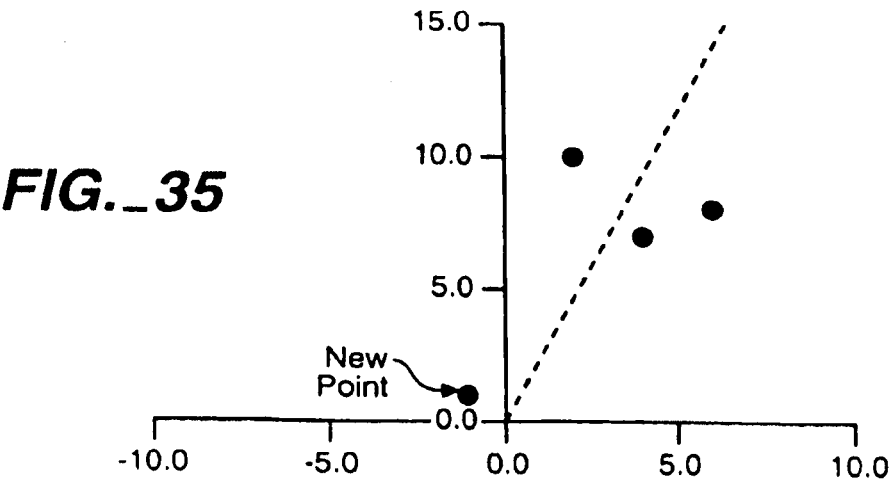
FIG._35

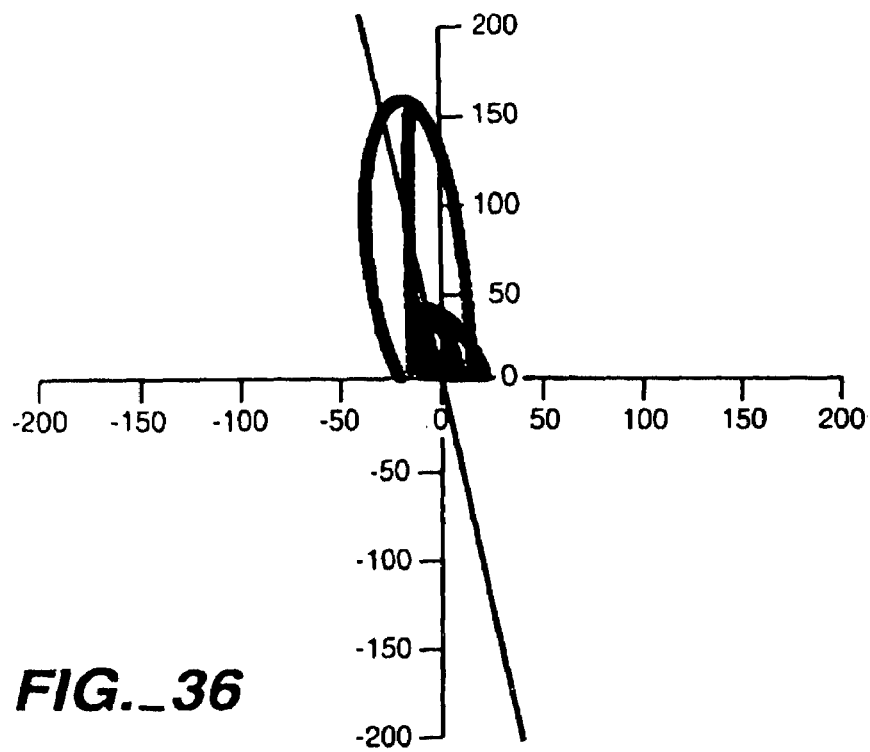
FIG.—36
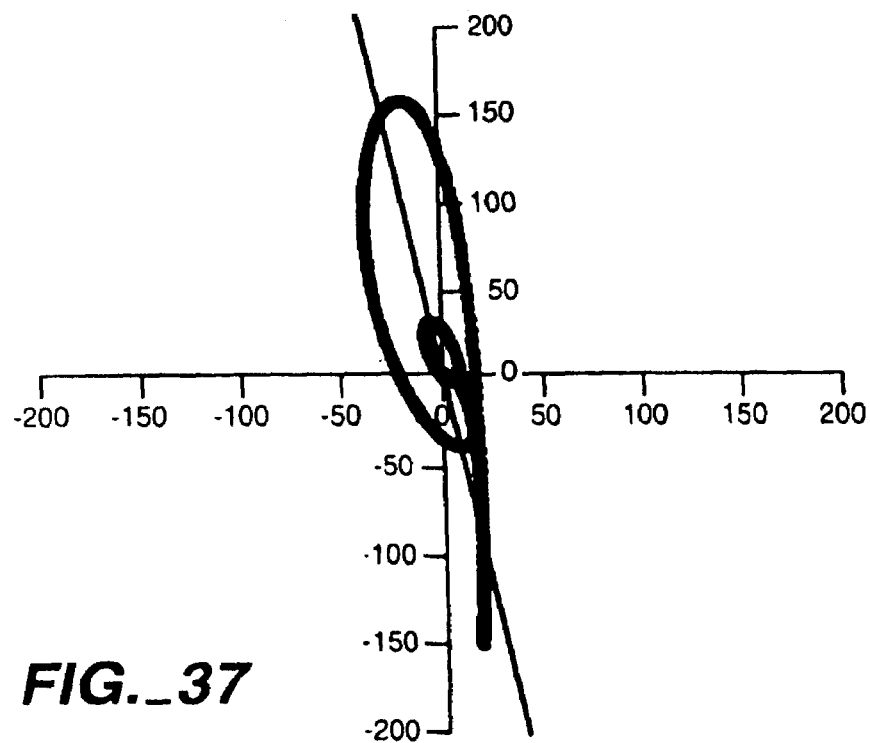
FIG.—37

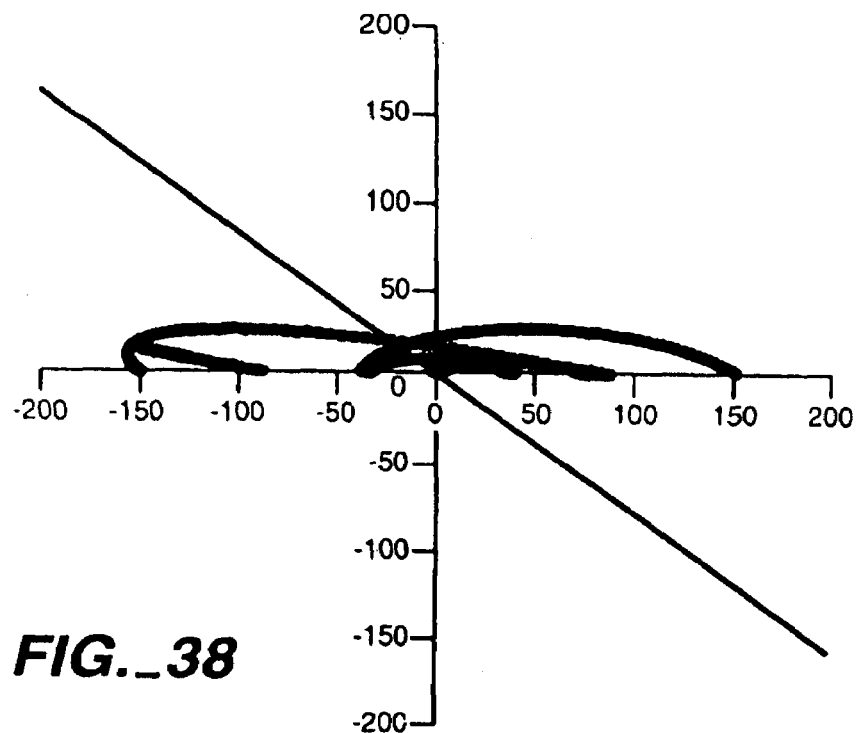
FIG._38
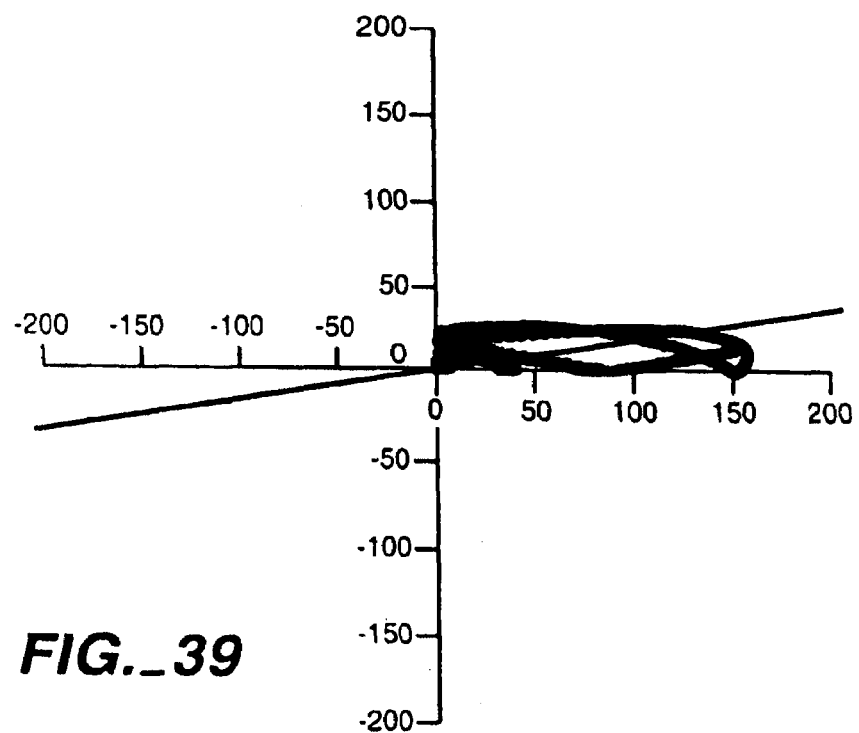
FIG._39

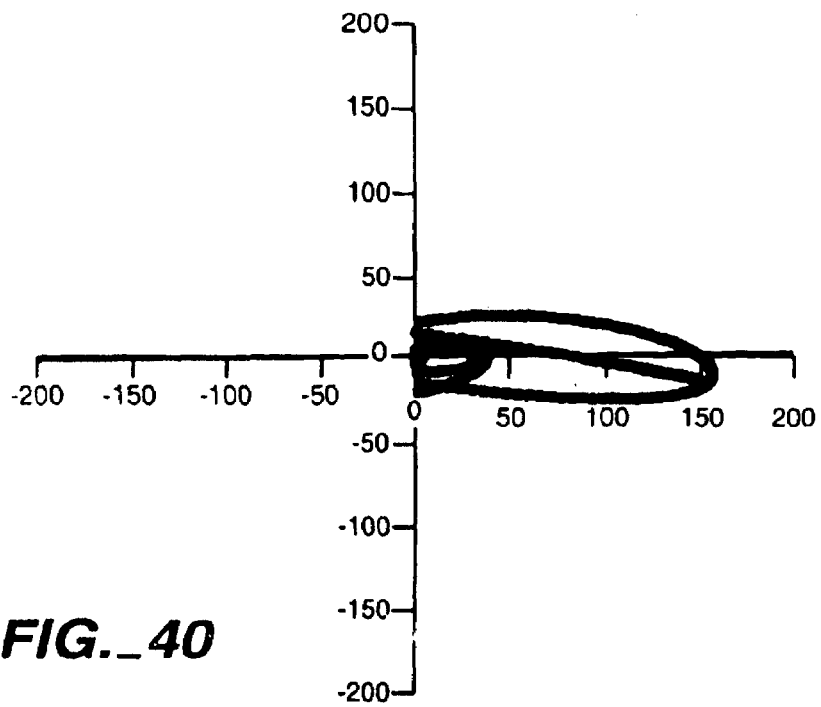
FIG._40
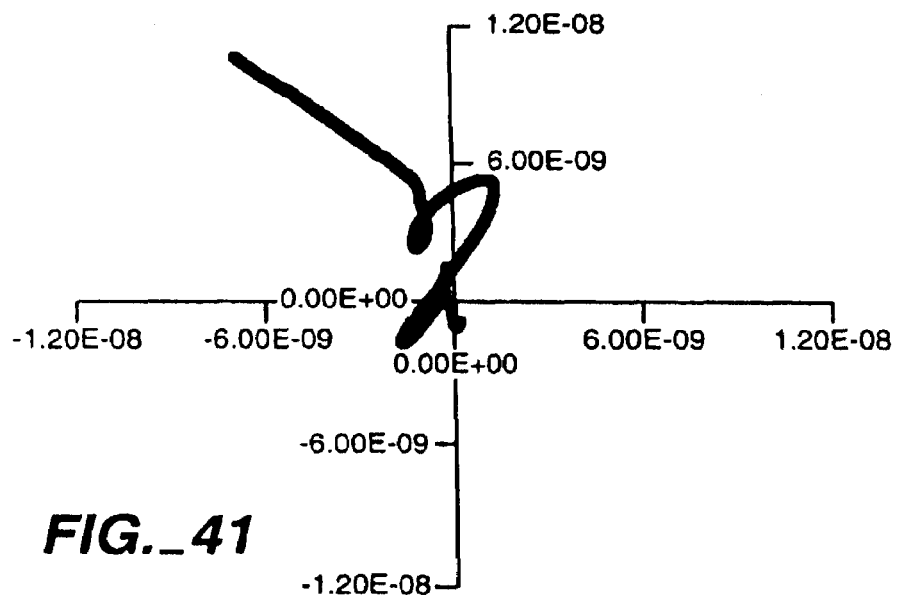
FIG._41

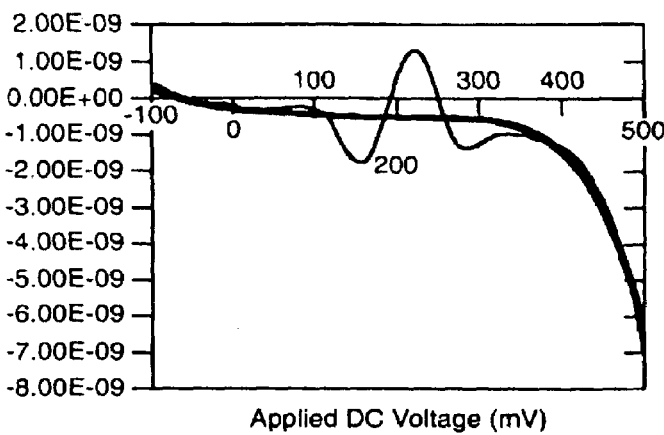
FIG._42
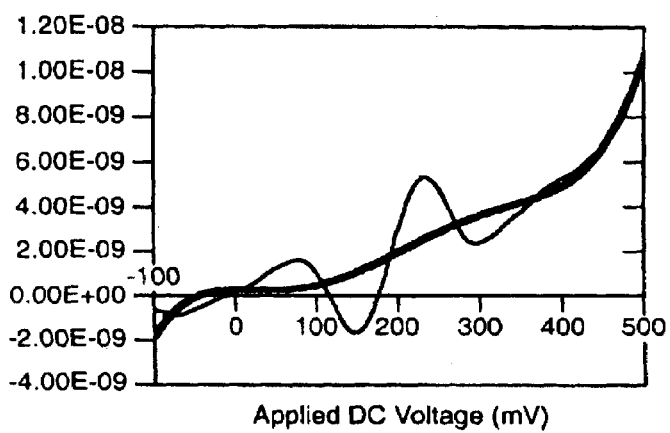
FIG._43
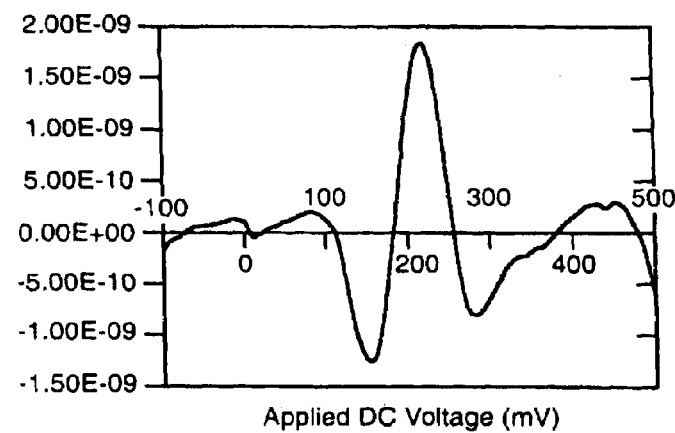
FIG._44

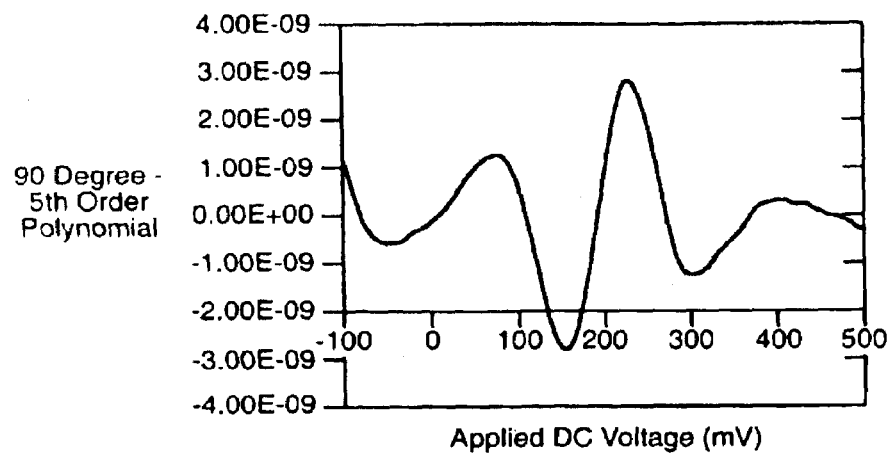
FIG._45
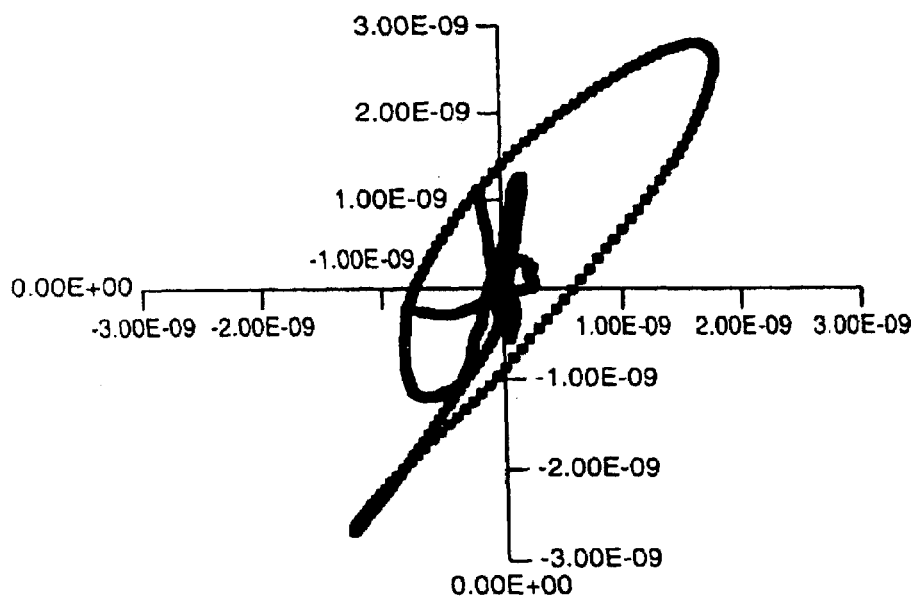
FIG._46

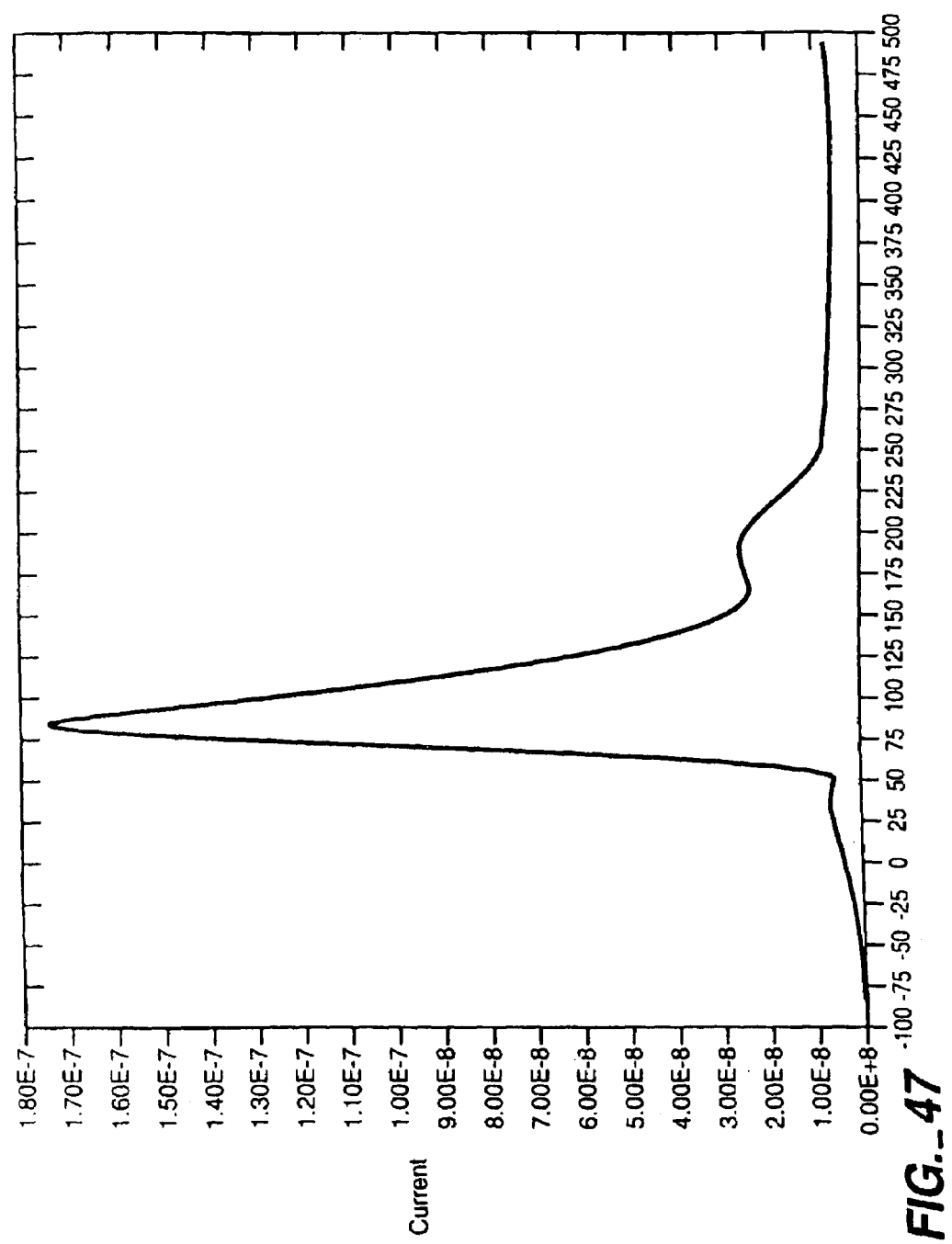
FIG._47

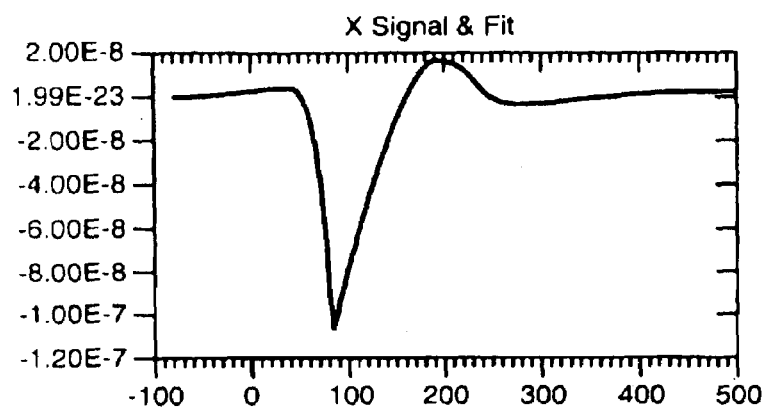
FIG._48
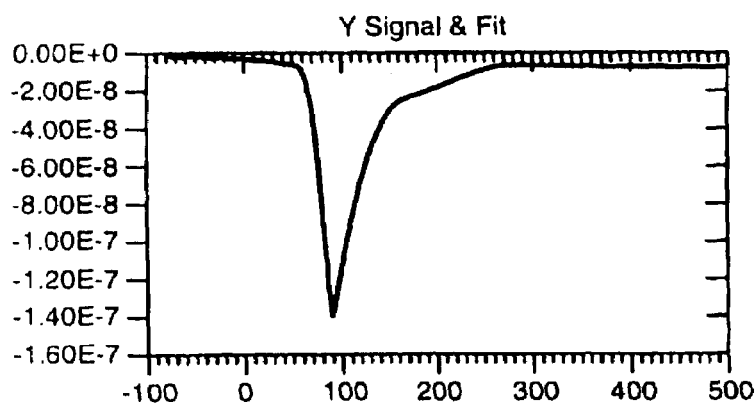
FIG._49
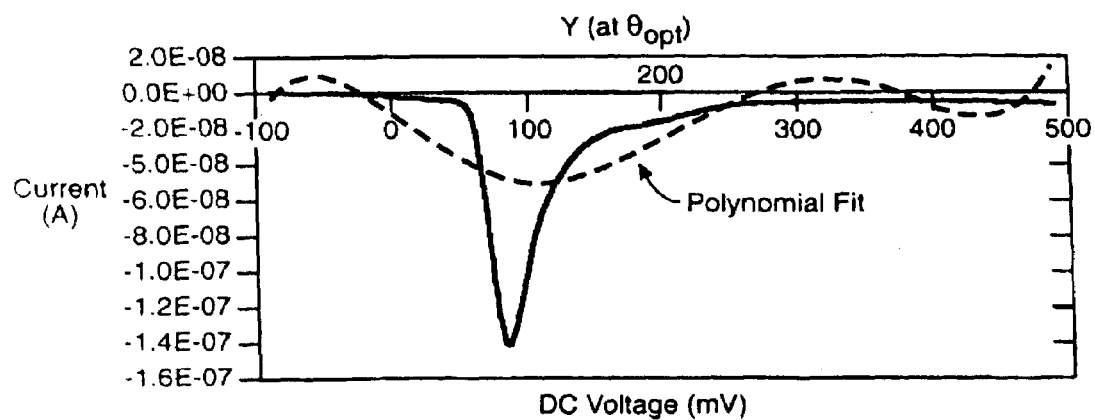
FIG._50

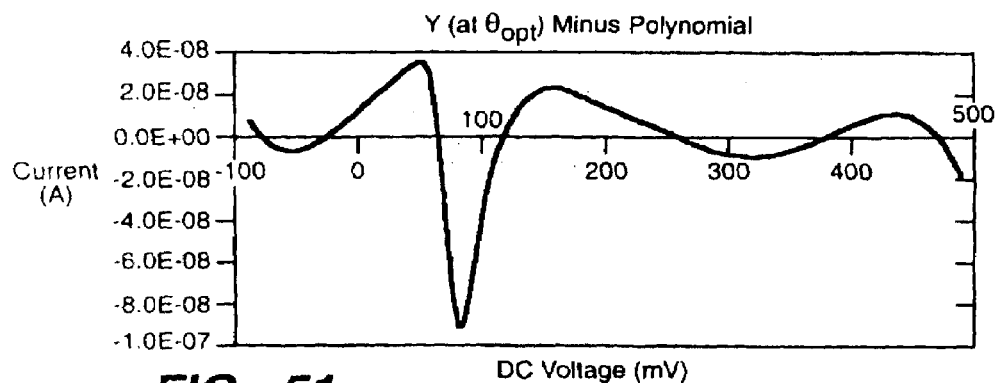
FIG._51
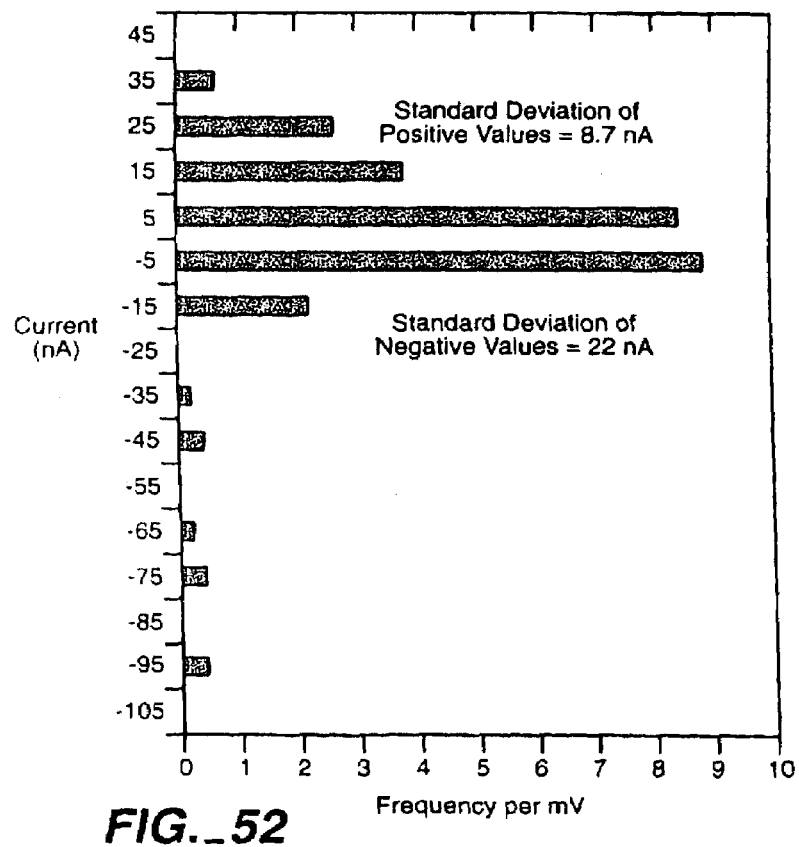
FIG._52

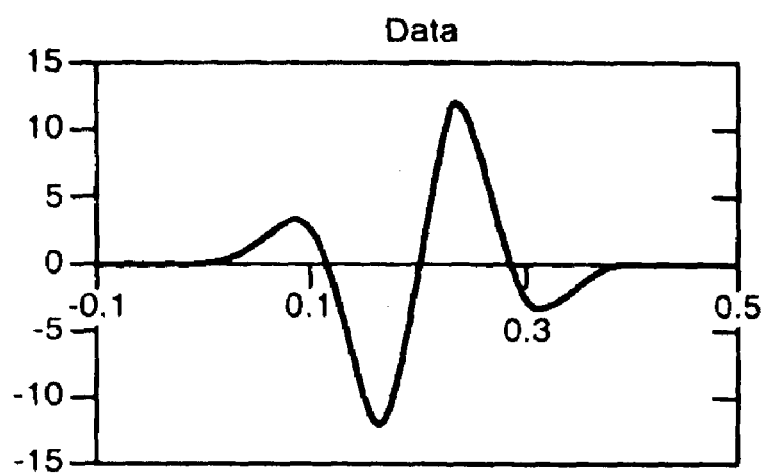
FIG._53
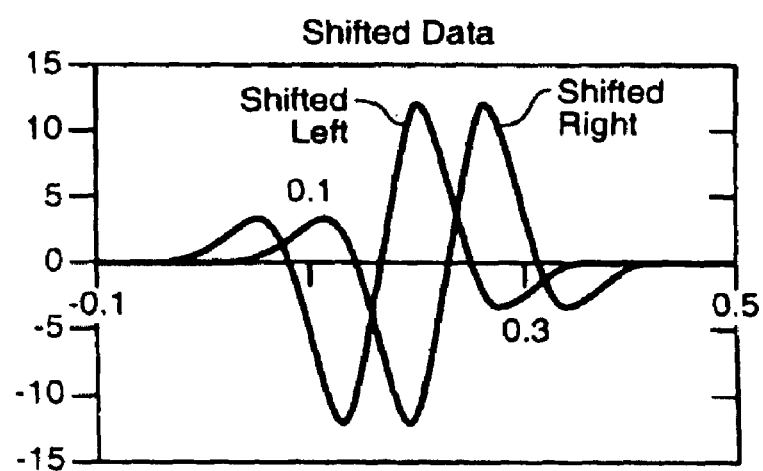
FIG._54

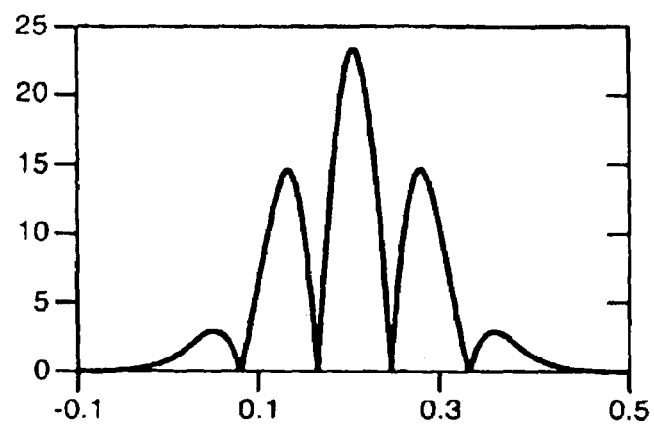
FIG._55
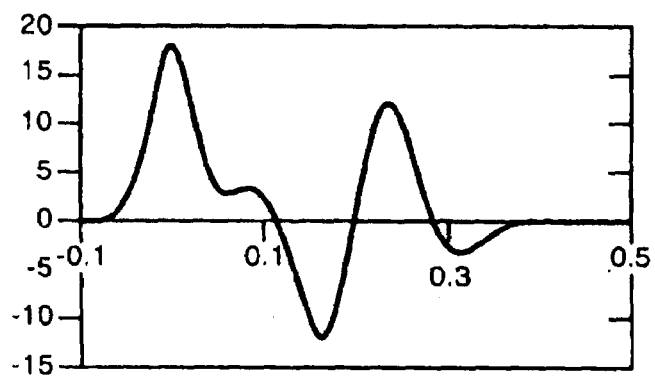
FIG._56
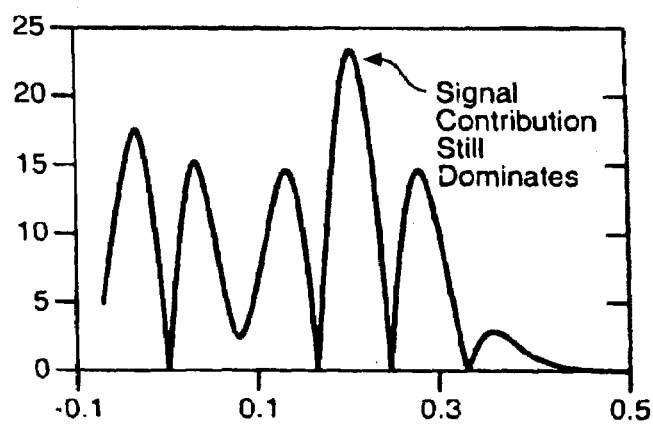
FIG._57

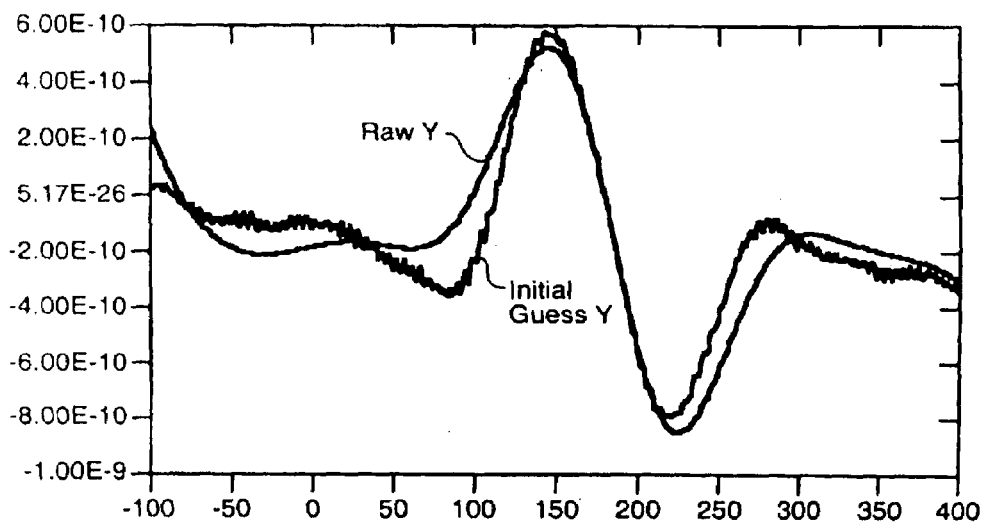
FIG._58
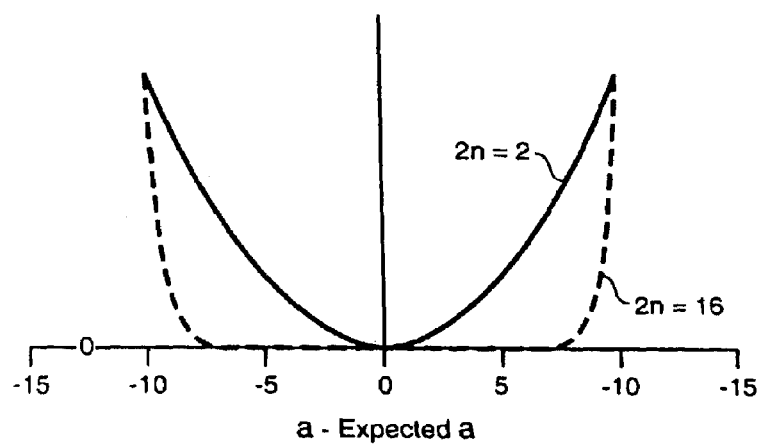
FIG._59

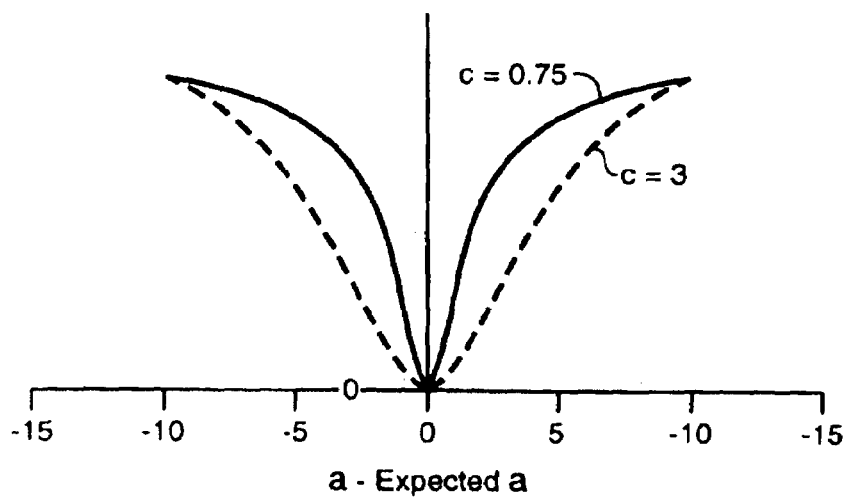
FIG._60
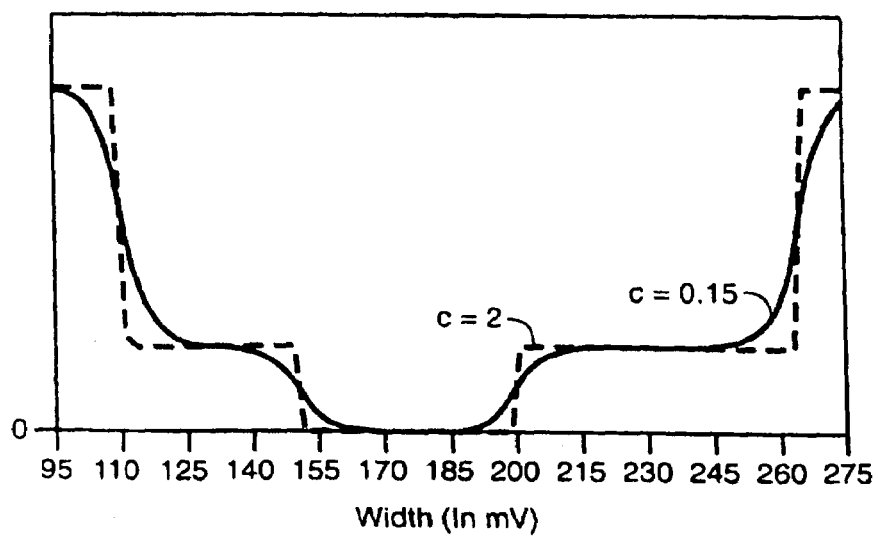
FIG._61

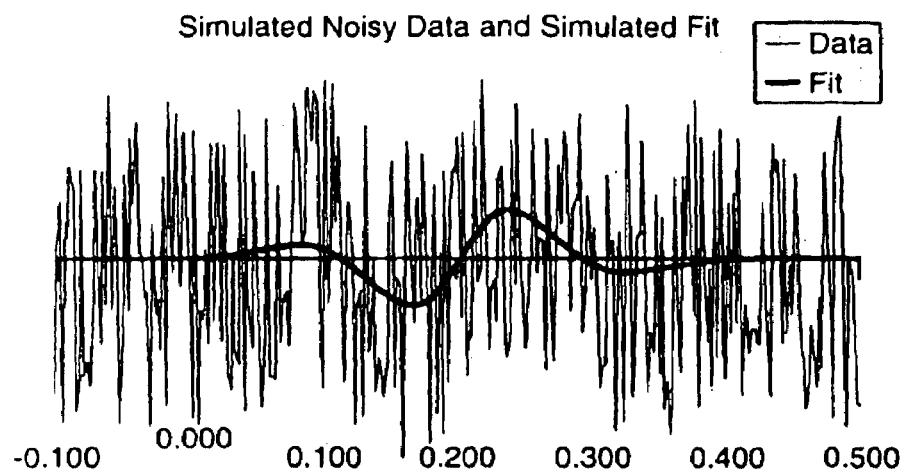
FIG._62
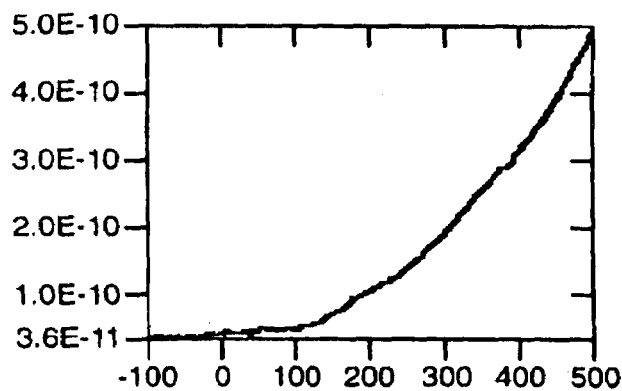
FIG._63
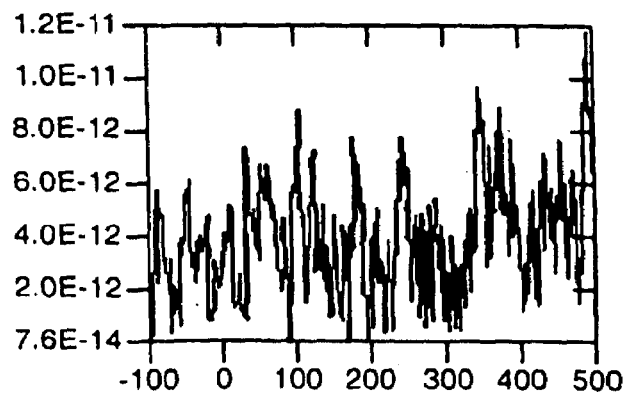
FIG._64

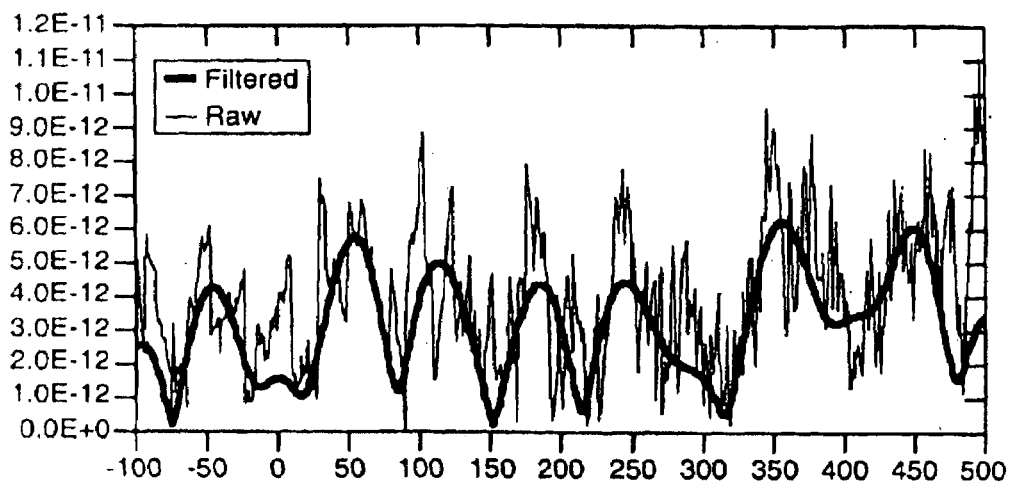
FIG._65
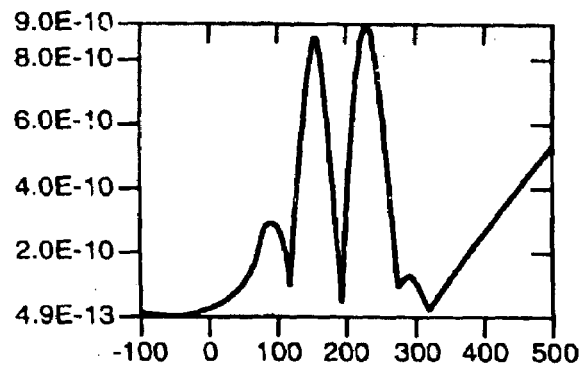
FIG._66
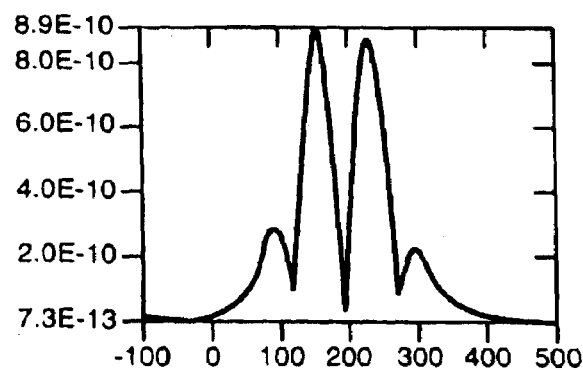
FIG._67

DEVICES AND METHODS FOR BIOCHIP MULTIPLEXING

FIELD OF THE INVENTION

The invention is directed to devices that allow for simultaneous multiple biochip analysis. In particular, the devices are configured to hold multiple cartridges comprising biochips comprising arrays such as nucleic acid arrays, and allow for high throughput analysis of samples.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Other assays rely on electronic signals for detection. Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein. While some of these known sensors use alternating current (AC) techniques, these techniques are generally limited to the detection of differences in bulk (or dielectric) impedance.

There are a variety of nucleic acid biosensors currently known. These include nucleic acid biochips based on fluorescent detection; see for example materials developed by Affymetrix (including, but not limited to, 5,800,992, 5,445,934, 5,744,305, and related patents and materials), Nanogen (including, but not limited to, 5,532,129, 5,605,662, 5,565,322 and 5,632,957 and related patents and materials), Southern (EP 0 373 023 B1) and Synteni/Incyte (WO 95/35505 and related patents and materials).

Similarly, electronic detection of nucleic acids using electrodes is also known; see for example U.S. Pat. Nos. 5,591,578; 5,824,473; 5,705,348; 5,780,234 and 5,770,369; U.S. Ser. Nos. 08/873,598 08/911,589; and WO 98/20162; PCT/US98/12430; PCT/US98/12082; PCT/US99/10104; PCT/US99/01705, and PCT/US99/01703 and related materials.

However, to date none of these methods have been used in highly parallel systems to allow biochip multiplexing. Accordingly, it is an object of the present invention to provide devices and methods for multiplex analysis of biochips, particularly nucleic acid biochips.

DETAILED DESCRIPTION OF THE DRAWINGS

FIG. 1 is of the cartridge with the rubber gasket in the inlet port.

FIG. 2 depicts a number of different reaction chamber geometries.

FIGS. 3-15 depict preferred embodiments of the invention.

FIG. 16 depicts a sine wave and its corresponding vector notation.

FIG. 17 depicts a vector notation in four configurations.

FIGS. 18 and 19 are examples of R and θ traces for fourth harmonic AC voltammetry (ACV-4).

FIGS. 20 and 21 depict examples of traces of scans with a smaller signal. FIGS. 22 and 23 (medium sized signal) depict graphs of the same examples shown in FIGS. 20 and 21 but now as (X,Y).

FIGS. 24 and 25 (smaller signal) depict graphs of the same examples shown in FIGS. 20 and 21 but now as (X,Y).

FIG. 26 depicts a two-dimensional graph plot of the tip of the data vector as a function of voltage.

FIGS. 27-28 depicts a graph choosing a frame of reference such that the X and Y axes straddle the signal.

FIGS. 29-30 depicts a graph choosing an axis pair that is roughly parallel and perpendicular to the signal (rotated 45° with respect to the axes drawn in the graph at the top of the page).

FIG. 31 depicts a grouping of three points.

FIG. 32 depicts a summation of the three points of FIG. 31.

FIG. 33 depicts the three points of FIG. 31 illustrating that we see how the three sample data points of FIG. 31 cluster around the line.

FIGS. 34 and 35 depict the result if an small data point is added to the group of FIG. 31.

FIG. 37 depicts the result of taking the data shown in FIG. 26 and calculating the optimal phase using the data as shown in FIG. 36, the resulting line being overlaid on the original data.

FIG. 38 depicts the result of FIG. 37 when orientating the signal differently relative to the dividing line between rotated and unrotated segments, in particular illustrating the calculated result when taking the signal of FIG. 37 and rotating it 101 degrees clockwise.

FIG. 39 depicts the case of FIG. 38 with a resulting angle of 10 degrees where the vectoral sum of the absolute value of the coordinates of a signal is more along 0 degrees.

FIG. 40 depicts rotation of the signal of FIG. 39 from the far side of the 90 degree axis.

FIG. 41 depicts the phase of the entire scan is mostly along 120°.

FIGS. 42 and 43 approximate the background by performing the rapid calculations necessary to fit polynomials to the entire scan (one each along the 0 and 90° axes).

FIGS. 44 and 45 depict the approximation to the background of FIGS. 42 and 43 after subtraction, converting the scan into something that is much more purely signal.

FIG. 46 depicts FIGS. 44 and 45 as a two dimensional plot.

FIG. 47 shows an example of sharp peak caused by the stripping of a metallic contaminant in AC voltammetry (fourth harmonic) displayed in R-space.

FIGS. 48 and 49 depict X and Y (at ± 45° from the optimal phase) the sharp spike feature of FIG. 47.

FIGS. 50 and 51 depict subtraction of a polynomial from the Y trace of FIGS. 48 and 49, illustrating one quick but rough method of monitoring this symmetry by separating out an approximate background (as we had done to determine the optimal phase) and then comparing the distribution of points above the baseline with the distribution below.

FIG. 52 depicts the distribution of data above and below the approximated background, illustrating that the presence of the spike causes a larger range of values to exist below the background line than above it.

FIGS. 53-55 depict one process of estimating the remaining parameters of signal position and signal height for a signal 11.9 tall at a position of 0.20 with a center lobe separation of 0.072.

FIGS. 56 and 57 depict the initial guess using the procedure of FIGS. 53-55 illustrating that the initial guess will remain 11.6 tall at a position of 0.20 with an unusual peak off to one side that's slightly taller than the signal itself.

FIG. 58 is the overlay of a real data trace and the corresponding initial guess of the above.

FIG. 59 is a graphical comparison of the shape when the added term is 2n=16 with when the shape when 2n=2, when we use the value of $k$ to determine how important it is to constrain the parameter relative to the standard error $E$ (and also relative to any other parameters' constraints).

FIG. 60 depicts the shape when using the following equation:

$$E' = E + k_1 \left[ \arctan\left(\frac{a - \bar{a}}{c}\right) \right]^2$$

FIG. 61 depicts other shapes using the case of our ACV-4-center lobe pairs (described previously).

FIG. 62 depicts a graph of a signal to be judged if the fit has too much error, that is, to make sure that we've locked into a real signal.

FIG. 63 is the R composite $\sqrt{X^2+Y^2}$.

FIG. 64 depicts the R composite with the background polynomials subtracted $\sqrt{(X - X_{background})^2 + (Y - Y_{background})^2}$.

FIG. 65 shows the filtered, signal-like noise is drawn on top of the residual (Raw) from the previous example.

FIG. 66 is the original data for scans with signals.

FIG. 67 is the data with the background subtracted, illustrating using the model as a guide we can use the fit parameters to calculate the equation for the background alone and subtract this from the data, for example, in ACV-4 we can subtract the polynomial X and in Y.

DETAILED DESCRIPTION

The present invention is directed to devices designed to receive and analyze a plurality of biochips, each comprising an array of biological moieties, such as nucleic acids or proteins, to allow high throughput analysis and detection of target analytes in samples. Thus for example a number of samples (particularly patient samples) can be simultaneously analyzed, or multiple assays can be run on a single sample. The devices comprise a number of cartridge stations that are configured to receive the biochips, with different types of biochips allowing different types of components. The stations can include a wide variety of different components, including thermocontrollers, signaling systems, sensors for leak detection, alphanumeric displays, and detectors. Preferred embodiments include the use of biochips comprising electrodes that rely on electrochemical detection, and thus the devices and/or stations can comprise device boards and processors.

The biochip cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

Accordingly, the present invention provides compositions and methods for detecting the presence or absence of target analytes in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The methods are directed to the detection of target analytes. By "target analyte" or "analyte" or grammatical equivalents herein is meant any molecule or compound to be detected and that can bind to a binding species, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs; cells; antibodies; antigens; cellular membrane antigens and receptors (neural, hormonal, nutrient, and cell surface receptors) or their ligands.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses or bacteria outlined below.

As will be appreciated by those in the art, a large number of analytes may be detected using the present methods; basically, any target analyte for which a binding ligand, described below, may be made may be detected using the methods of the invention.

In a preferred embodiment, the target analytes are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252-3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawis, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Thus, in a preferred embodiment, the target analyte is a target sequence. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

Suitable target analytes include biomolecules associated with: (1) viruses, including but not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicellazoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like; and (2) bacteria, including but not limited to, a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum, C. tetani, C. difficile, C. perfringens*; Cornyebacterium, e.g. *C. diphtheriae*; *Streptococcus, S. pyogenes, S. pneumoniae*; *Staphylococcus*, e.g. *S. aureus*; *Haemophilus*, e.g. *H. influenzae*; *Neisseria*, e.g. *N. meningitidis, N. gonorrhoeae*; *Yersinia*, e.g. *G. lamblia Y. pestis, Pseudomonas*, e.g. *P. aeruginosa, P. putida*; *Chlamydia*, e.g. *C. trachomatis*; *Bordetella*, e.g. *B. pertussis*; *Treponema*, e.g. *T. palladium*; and the like.

Other suitable target analytes include, but are not limited to, (1) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (2) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (3) other proteins (including α-fetoprotein, carcinoembryonic antigen CEA, cancer markers, etc.).

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Other suitable target analytes include metal ions, particularly heavy and/or toxic metals, including but not limited to, aluminum, arsenic, cadmium, selenium, cobalt, copper, chromium, lead, silver and nickel.

In a preferred embodiment, the methods of the invention are used to detect pathogens such as bacteria. In this embodiment, preferred target sequences include rRNA, as is generally described in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5.352.579; 5,683,870; 5,374,718; 5,292,874; 5,780,219; 5,030,557; and 5,541,308, all of which are expressly incorporated by reference.

As will be appreciated by those in the art, a large number of analytes may be detected using the present methods; basically, any target analyte for which a binding ligand, described below, may be made may be detected using the methods of the invention. While many of the techniques described below exemplify nucleic acids as the target analyte, those of skill in the art will recognize that other target analytes can be detected using the same systems.

If required, the target analyte is prepared using known techniques. For example, the sample may be treated to lyse the cells, using known lysis buffers, electroporation, etc., with purification and/or amplification as needed, as will be appreciated by those in the art. When the target analyte is a nucleic acid, the target sequence may be amplified as required; suitable amplification techniques are outlined in PCT US99/01705, hereby expressly incorporated by reference. In addition, techniques to increase the amount or rate of hybridization can also be used; see for example WO 99/67425 and U.S. Ser. Nos. 09/440,371 and 60/171,981, all of which are hereby incorporated by reference.

The samples comprising the target analytes can be added to cartridges comprising the biochips as is outlined in greater detail below. By "cartridge" herein is meant a casing or housing for the biochip. As outlined herein, and as will be appreciated by those in the art, the cartridge can take on a number of configurations and can be made of a variety of materials. Suitable materials include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), etc. Particularly preferred cartridge materials. are plastic (including polycarbonate and polyproplylene) and glass.

As will be appreciated by those in the art, the cartridge can comprise a number of components, including reaction chambers, inlet and outlet ports, heating elements including thermoelectric components, RF antennae, electromagnetic components, memory chips, sealing components such as gaskets, electronic components including interconnects, multiplexers, processors, etc.

In a preferred embodiment, the cartridge comprises a reaction chamber. Generally, the reaction chamber comprises a space or volume that allows the contacting of the sample to the biochip array. The volume of the reaction chamber can vary depending on the size of the array and the assay being done. In general, reaction chamber ranges from 1 nL to about 1 mL, with from about 1 to about 250 µl being preferred and from about 10 to about 100 µl being especially preferred. In some embodiments, to avoid the introduction of air bubbles into the reaction chamber (which can be disruptive to detection), the reaction chamber is less than the size of the sample to be introduced, to allow a slight overflow and thus ensure that the reaction chamber contains little or no air.

The reaction chamber of the cartridge comprises an inlet port for the introduction of the sample to be analyzed. The inlet port may optionally comprise a seal to prevent or reduce the evaporation of the sample or reagents from the reaction chamber. In a preferred embodiment (as depicted in FIG. 1), the seal comprises a gasket, through which a pipette or syringe can be pushed. The gasket can be rubber or silicone or other suitable materials.

The reaction chamber can be configured in a variety of ways. In a preferred embodiment, the reaction chamber is configured to minimize the introduction or retention of air bubbles or other sample impurities. Thus for example, as depicted in FIG. 1, assuming that the cartridge is held in an upright angle, the inlet port allows the flow of fluid sample into the "bottom" of the reaction chamber, to allow the escape of air or fluid through the "top" of the reaction chamber, for example through an outlet port. Thus the fluid sample flows up into the reaction chamber and contacts the array. Thus, in a preferred embodiment, the reaction chamber further comprises an outlet port to allow air or excess sample to exit the reaction chamber. In some embodiments, the outlet port vents to either a waste storage well, as is further described below, to an external surface of the chip or cartridge, or, in a preferred embodiment, back into the inlet port. Thus for example a preferred embodiment utilizes a system wherein the exit port vents to the inlet port, preferably above the point of loading. For example, when a pipette is used to load the cartridge, the tip of the pipette extends below the exit port, such that air from the exit port is not introduced into the reaction chamber. In addition, the materials of the cartridge housing and biochip can be chosen to be similar in hydrophobicity or hydrophilicity, to avoid the creation of air bubbles.

In addition, in a preferred embodiment, the reaction chamber/inlet and/or outlet ports optionally include the use of valves. For example, a semi-permeable membrane or filter may be used, that preferentially allows the escape of gas but retains the sample fluid in the chamber. For example, porous teflons such as Gortex™ allow air but not fluids to penetrate.

As will be appreciated by those in the art, there are a variety of reaction chamber geometries which can be used in this way. Generally having the intersection of the inlet port and the reaction chamber be at the "bottom" of the cartridge, with a small aperture, with the reaction chamber widening, is preferred. In addition, the "top" of the reaction chamber may be narrow, as well. Several embodiments are depicted in FIG. 2. Thus, preferred embodiments for the size and shape of the reaction chamber allow for smooth loading of the reaction chamber. Preferred embodiments utilize reaction chamber geometries that avoid the use of sharp corners or other components that serve as points for bubble formation.

In addition, in some embodiments, the reaction chamber can be configured to allow mixing of the sample. For example, when a sample and a reagent are introduced simultaneously or separately into the chamber, the inlet port and/or the reaction chamber can comprise weirs, channels or other components to maximize the mixing of the sample and reagent. In addition, as is outlined below, the reaction may utilize magnetic beads for mixing and/or separation.

In a preferred embodiment, the cartridge comprises a sealing mechanism to prevent leakage of the sample or reagents onto other parts of the substrate, particularly (in the case of electronic detection) onto electronic interconnects. As will be appreciated by those in the art, this may take on a variety of different forms. In one embodiment, there is a gasket between the biochip substrate comprising the array and the cartridge, comprising sheets, tubes or strips. Alternatively, there may be a rubber or silicone strip or tube used; for example, the housing may comprise an indentation or channel into which the gasket fits, and then the housing, gasket and chip are clamped together. Furthermore, adhesives can be used to attach the gasket to the cartridge, for example, a double sided adhesive can be used; for example, silicone, acrylic and combination adhesives can be used to attach the gasket to the biochip, which is then clamped into the cartridge as described herein.

In some embodiments, the reaction chamber and biochip substrate are configured such that a separate sealing mechanism is not required. For example, the biochip substrate can serve as one "half" of the reaction chamber, with the array on the inside, and the reaction chamber housing can serve as the other "half". Depending on the materials used, there may be an optional adhesive to attach the two. Alternatively, when there are arrays on both sides of the substrate, the housing may encompass the substrate.

Thus, in these embodiments, the volume of the reaction chamber can be set either by forming a well in the cartridge, such that the addition of the biochip substrate forms a reaction chamber around the array, or by using a flat cartridge and using a gasket of a defined depth, or by combinations of the two.

In a preferred embodiment, the cartridge comprises a cap or lid. The cap may be functional, as outlined below when it comprises microfluidic components. In addition, the cap may be designed for safety purposes, to prevent the leakage of biological materials or cross-contamination. As will be appreciated by those in the art, the cap can take on a wide variety of configurations. For example, in one embodiment, the cap merely seals the inlet port to prevent evaporation of the sample during the assay. In a preferred embodiment, the cap may comprise a number of additional elements for use in sample handling and reagent storage, to allow for a variety of different sample reactions. For example, a variety of microfluidic components can be built into the cap to effect a number of manipulations on a sample to ultimately result in target analyte detection or quantitation. See generally PCT US00/10903, and references outlined therein, all of which are expressly incorporated by reference. These manipulations can include cell handling (cell concentration, cell lysis, cell removal, cell separation, etc.), separation of the desired target analyte from other sample components, chemical or enzymatic reactions on the target analyte, detection of the target analyte, etc. The devices of the invention can include one or more wells for sample manipulation, waste or reagents; microchannels (sometimes referred to as flow channels) to and between these wells, including microchannels containing electrophoretic separation matrices; valves to control fluid movement; on-chip pumps such as electroosmotic, electrohydrodynamic, or electrokinetic pumps. In addition, as outlined herein, portions of the internal surfaces of the device may be coated with a variety of coatings as needed, to reduce non-specific binding, to allow the attachment of binding ligands, for biocompatibility, for flow resistance, etc. These microfluidic caps can be made in a variety of ways, as will be appreciated by those in the art. See for example references described in PCT US00/10903, and references outlined therein, all of which are expressly incorporated by reference.

When the cap of the cartridge is used as part of the assay, it may be configured to include one or more of a variety of components, herein referred to as "modules", that will be present on any given device depending on its use, and are connected as required by microchannels. These modules include, but are not limited to: sample inlet ports; sample introduction or collection modules; cell handling modules (for example, for cell lysis, cell removal, cell concentration, cell separation or capture, cell growth, etc.); separation modules, for example, for electrophoresis, dielectrophoresis, gel filtration, ion exchange/affinity chromatography (capture and release) etc.; reaction modules for chemical or biological alteration of the sample, including amplification of the target analyte (for example, when the target analyte is nucleic acid, amplification techniques are useful, including, but not limited to polymerase chain reaction (PCR), oligonucleotide ligation assay (OLA); strand displacement amplification (SDA), and nucleic acid sequence based amplification (NASBA) and other techniques outlined in WO 99/37819 and PCT US00/19889), chemical, physical or enzymatic cleavage or alteration of the target analyte, or chemical modification of the target; fluid pumps (including, but not limited to, electroosmotic, electrohydrodynamic, or electrokinetic pumps; fluid valves; thermal modules for heating and cooling; storage modules for assay reagents; mixing chambers; and detection modules.

In addition, while these microfluidic components are described herein as being associated with the cap of the cartridge, as will be appreciated by those in the art, these modules and channels (as well as other components outlined herein) may be located anywhere in the cartridge or device. In addition, some components may be in the device; for example, "off chip" pumps may be located within one or more stations of the device.

The cartridge comprises at least one biochip, with some embodiments utilizing one or more biochips per cartridge. By "biochip" or equivalents herein is meant a substrate comprising an array of distinct biomolecules, particularly nucleic acids and proteins. There are a wide variety of suitable nucleic acid biochips, including those made using photolithographic techniques (such as the Affymetrix GeneChip™), spotting techniques (e.g. Synteni and Incyte), prining techniques (Agilent and Rosetta), three dimensional "gel pad" arrays, and those including electronic components (e.g. Nanogen). A preferred embodiment is described below and in U.S. Pat. Nos. 5,591,578; 5,824,473; 5,705,348; 5,780,234 and 5,770,369; U.S. Ser. Nos. 08/873,598 08/911,589; WO 98/20162; WO98/12430; WO98/57158; WO 00/16089) WO99/57317; WO99/67425; WO00/24941; PCT US00/10903; WO00/38836; WO99/37819; WO99/57319 and PCTUS00/20476; and related materials, all of which are expressly incorporated by reference in their entirety.

It should be noted that one distinct advantage of the use of the electronic detection methods outlined herein is that real time monitoring of reactions and hybridization can occur. That is, while systems based on fluorescence require the removal of excess (e.g. unbound) signaling probes (or target sequences when the target sequence itself has been fluorescently labeled during an amplification reaction, for example), the electronic methods outlined herein do not. That is, unless the probes comprising the ETMs are bound to the surface, little or no signal is seen even if unbound probes have not been removed. This allows the monitoring of real-time reactions, as well as multiple measurements on the same array. Accordingly, while the discussion below is directed mainly to the use of biochips comprising an array of electrodes, other array technologies are included in the present invention.

In a preferred embodiment, the biochips comprise substrates with a plurality of array locations. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture ligands to many thousands can be made. Generally, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

In a preferred embodiment, the biochip comprises a substrate with at least one surface comprising an array, and in a preferred embodiment, an array of electrodes. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode is an ETM as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo2O6), tungsten oxide (WO3) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used and the configuration of the cartridge. For example, flat planar electrodes may be preferred for optical detection methods, or when arrays of nucleic acids are made, thus requiring addressable locations for both synthesis and detection. Alternatively, for single or low density analysis, the electrode may be in the form of a tube; this allows a maximum of surface area containing the nucleic acids to be exposed to a small volume of sample.

In a preferred embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as outlined above.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, preferred embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Preferred brighteners are mixtures of organic and inorganic species, with cobalt and nickel being preferred.

In general, the adhesion layer is from about 100 Å thick to about 25 microns (1000 microinches). The If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

In one embodiment of the inventive structure, the solder mask is desirably made of a solvent soluble material rather than a water soluble material. Water soluble solder masks have become standard in the industry because of the environmental advantages of water soluble materials generally. Unfortunately, for a detector chip that is to be exposed to aqueous solutions, water soluble materials such as for example acetonitrile can dissolve when exposed to aqueous solution.

The methods continue with the addition of SAMs, described below. In a preferred embodiment, drop deposition techniques are used to add the required chemistry, i.e. the monolayer forming species, one of which is preferably a capture ligand comprising species. Drop deposition techniques are well known for making "spot" arrays. This is done to add a different composition to each electrode, i.e. to make an array comprising different capture ligands. Alternatively, the SAM species may be identical for each electrode, and this may be accomplished using a drop deposition technique or the immersion of the entire substrate or a surface of the substrate into the solution.

When the biochips comprise electrodes, there are a variety of additional components in addition to the chemistry outlined below, which may be present on the chip, including, but not limited to, interconnects, multiplexers, relay devices, filters, RF antennae, heating elements, electromagnetic components, etc.

Each electrode comprises an independent lead (interconnect) to transmit input and electronic response signals for each electrode of the array. In contrast to previous systems which require the ability to independently alter only input signals to each electrode but not electronic response signals, it is important in the present invention that both input and electronic response signals be independently monitorable for each electrode.

For a relatively small number of electrode pads and/or depending on the desired size of the array, providing direct connections using parallel circuits may be appropriate.

In a preferred embodiment, each electrode is individually connected to a corresponding input of a multiplexer via a corresponding interconnector. One problem presented in conventional systems and methods is the difficulty in providing electrical connections (inputs and/or outputs) to a large number of electrodes, particularly if the electrodes form a dense or close packed array. Several solutions to this problem have been identified, and include the use of circuitry that allows signal processing either simultaneously as sets of parallel circuits and connections, line-sample array addressing, serially in a time-domain multiplexed manner, or in parallel or serially using frequency domain and/or time-domain based separation techniques, among other available techniques, as are outlined herein.

For example, a preferred method to connect a first multiplicity of circuits or lines on the chip to a smaller plurality of lines at a connector leading from the chip are to use a switching device such as a multiplexer (MUX) or relays to selectively couple circuits on the chip or board with circuits off the board.

The number of multiplexers will depend on the number of electrodes in the array. In one embodiment, a single MUX is utilized. In a preferred embodiment, a plurality of MUXs are used. This can be done in a variety of ways, as will be appreciated by those in the art; in one embodiment, "sectors" of electrodes are assigned to a particular MUX; thus for example, rows or columns of the array may each have their own MUX. Alternatively, submultiplexers are used; for example, a column or row is connected to a respective sub-multiplexer, with the sub-multiplexer outputs going to another submultiplexer.

In a preferred embodiment, the multiplexer includes a binary counter which receives the control signal via the connector pad. The control signal is preferably a pulsed signal such as a clock signal and generates a sequential count to drive the decoders.

In a preferred embodiment, another way to connect a multiplicity of electrodes on the substrate to a smaller number of connector pads leading "off chip" is to use row-column select signals to allow the selection of individual electrodes.

Unfortunately, for structures and methods that access different electrodes or groups of electrodes in a time sequential manner, some correction or adjustment of the sensed results may be required when the difference in time is sufficiently large to alter the results, in order to maintain a calibration between earlier sensed and read-out data and later sensed and read-out data. The need for such adjustment will depend upon the assay, reaction kinetics and the time separation which may also be a function of the number of electrodes to be sensed or read-out. For example, in some embodiments it may be entirely reasonable to measure each of the 25 electrodes in a 5×5 array of electrodes a few seconds apart (e.g. 10 seconds apart); however, in other embodiments, the 4 minute separation between the first and last measurement may be unacceptable or difficult to compensate.

It is also desirable to consider the kinetics of reaction when the reaction takes place on or near a planar surface, such as the surface of the electrode. Diffusion rates may play a more important role than when the reaction occurs in solution. It is important to understand when or over what period of time the reaction takes place so that the measurements are taken at the appropriate time. This may be particularly important if an intermediate reaction product is to be sensed, or if a series of measurements are desirable, for example to do reaction kinetics.

Reaction kinetics are also an important consideration for the driving signals. Biosensors are limited by the chemical kinetics. For the class of molecules of interest here (DNA, DNA fragments, proteins, antibodies, and the like), each molecule has a maximum speed or velocity in the medium. For example, the molecules may typically be actively driven or moved in solution at frequencies between about 1 Hz and 10 kHz, more typically between about 5 Hz and 5 kHz. At higher frequencies, the molecules only vibrate, while at lower frequencies the movement is not particularly useful.

In addition, there is an assay volume, that is the accessible volume of the assay, associated with each driving signal frequency. As the frequency increases, the assay volume shrinks in size and volume. This has implication for the distribution of electrodes and the driving signal frequency.

One additional consideration for sensing or measuring a reaction is the possible effect that the reaction medium (such as solution components, sample components, reaction components, etc.) may have on the electrodes. Sometimes the electrodes will degrade, become passivated, or otherwise change over time thereby affecting the accuracy and uniformity of measurements. Under such conditions it is desirable to perform the sensing, measurement, or analysis quickly, or at least according to predetermined timings so that the data collected will be properly interpreted.

In a preferred embodiment, one or more preamplifiers are used. As will be appreciated by those in the art, the preamplifier can be on the surface of the substrate, e.g. "on board" or "on chip", or may be provided in circuitry external to the array chip. It is preferable, however, that the preamplifier be included on the substrate to increase the signal-to-noise ratio of the signal provided to the external circuitry.

In a preferred embodiment, each individual electrode has an associated preamplifier.

In a preferred embodiment, the array is divided into "sectors", wherein a subset of the electrodes in the array have an associated MUX and preamplifier. Similarly, other components of the invention may be associated with sectors.

In a preferred embodiment, impedance matching is done.

In a preferred embodiment, filters are used, including, but not limited to, time domain filters and a frequency domain filters, and combinations.

In addition to electronic components, the electrodes of the invention in preferred embodiments comprise self-assembled monolayers (SAMs). The compositions of these SAMs will vary with the detection method used. In general, there are two basic detection mechanisms. In a preferred embodiment, detection of an ETM is based on electron transfer through the stacked n-orbitals of double stranded nucleic acid. This basic mechanism is described in U.S. Pat. Nos. 5,591,578, 5,770,369, 5,705,348, and PCT US97/20014 and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

Alternatively, the ETM can be detected, not necessarily via electron transfer through nucleic acid, but rather can be directly detected on an electrode comprising a SAM; that is, the electrons from the ETMs need not travel through the stacked n orbitals in order to generate a signal. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs.

It should be noted that these defects are to be distinguished from "holes" that allow direct contact of sample components with the detection electrode. As is more fully outlined below, the electroconduits can be generated in several general ways, including but not limited to the use of rough electrode surfaces, such as gold electrodes formulated on PC circuit boards; or the inclusion of at least two different species in the monolayer, i.e. using a "mixed monolayer", at least one of which is a electroconduit-forming species (EFS). Thus, upon binding of a target analyte, a soluble binding ligand comprising an ETM is brought to the surface, and detection of the ETM can proceed, putatively through the "electroconduits" to the electrode. Essentially, the role of the SAM comprising the defects is to allow contact of the ETM with the electronic surface of the electrode, while still providing the benefits of shielding the electrode from solution components and reducing the amount of non-specific binding to the electrodes. Viewed differently, the role of the binding ligand is to provide specificity for a recruitment of ETMs to the surface, where they can be directly detected.

Thus, in either embodiment, as is more fully outlined below, an assay complex is formed that contains an ETM, which is then detected using the detection electrode.

Thus, in a preferred embodiment, the electrode comprises a monolayer, comprising electroconduit forming species (EFS). As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer.

In general, the SAMs of the invention can be generated in a number of ways and comprise a number of different components, depending on the electrode surface and the system used. For "mechanism-1" embodiments, preferred embodiments utilize two monolayer forming species: a monolayer forming species (including insulators or conductive oligomers) and a conductive oligomer species comprising the capture binding ligand, although as will be appreciated by those in the art, additional monolayer forming species can be included as well. For "mechanism-2" systems, the composition of the SAM depends on the detection electrode surface. In general, two basic "mechanism-2" systems are described; detection electrodes comprising "smooth" surfaces, such as gold ball electrodes, and those comprising "rough" surfaces, such as those that are made using commercial processes on PC circuit boards. In general, without being bound by theory, it appears that monolayers made on imperfect surfaces, i.e. "rough" surfaces, spontaneously form monolayers containing enough electroconduits even in the absence of EFS, probably due to the fact that the formation of a uniform monolayer on a rough surface is difficult. "Smoother" surfaces, however, may require the inclusion of sufficient numbers of EFS to generate the electroconduits, as the uniform surfaces allow a more uniform monolayer to form. Again, without being bound by theory, the inclusion of species that disturb the uniformity of the monolayer, for example by including a rigid molecule in a background of more flexible ones, causes electroconduits. Thus "smooth" surfaces comprise monolayers comprising three components: an insulator species, a EFS, and a species comprising the capture ligand, although in some circumstances, for example when the capture ligand species is included at high density, the capture ligand species can serve as the EFS. "Smoothness" in this context is not measured physically but rather as a function of an increase in the measured signal when EFS are included. That is, the signal from a detection electrode coated with monolayer forming species is compared to a signal from a detection electrode coated with monolayer forming species including a EFS. An increase indicates that the surface is relatively smooth, since the inclusion of a EFS served to facilitate the access of the ETM to the electrode. It should also be noted that while the discussion herein is mainly directed to gold electrodes and thiol-containing monolayer forming species, other types of electrodes and monolayer-forming species can be used.

It should be noted that the "electroconduits" of mechanism-2 systems do not result in direct contact of sample components with the electrode surface; that is, the electroconduits are not large pores or holes that allow physical access to the electrode. Rather, without being bound by theory, it appears that the electroconduits allow certain types of ETMs, particularly hydrophobic ETMs, to penetrate sufficiently into the monolayer to allow detection. However, other types of redox active species, including some hydrophilic species, do not penentrate into the monolayer, even with electroconduits present. Thus, in general, redox active species that may be present in the sample do not give substantial signals as a result of the electroconduits. While the exact system will vary with the composition of the SAM and the choice of the ETM, in general, the test for a suitable SAM to reduce non-specific binding that also has sufficient electroconduits for ETM detection is to add either ferrocene or ferrocyanide to the SAM; the former should give a signal and the latter should not.

Accordingly, in mechanism-1 systems, the monolayer comprises a first species comprising a conductive oligomer comprising the capture binding ligand, as is more fully outlined below, and a second species comprising a monolayer forming species, including either or both insulators or conductive oligomers.

In a preferred embodiment, the monolayer comprises electroconduit-forming species. By "electroconduit-forming species" or "EFS" herein is meant a molecule that is capable of generating sufficient electroconduits in a monolayer, generally of insulators such as alkyl groups, to allow detection of ETMs at the surface. In general, EFS have one or more of the following qualities: they may be relatively rigid molecules, for example as compared to an alkyl chain; they may attach to the electrode surface with a geometry different from the other monolayer forming species (for example, alkyl chains attached to gold surfaces with thiol groups are thought to attach at roughly 45° angles, and phenyl-acetylene chains attached to gold via thiols are thought to go down at 90° angles); they may have a structure that sterically interferes or interrupts the formation of a tightly packed monolayer, for example through the inclusion of branching groups such as alkyl groups, or the inclusion of highly flexible species, such as polyethylene glycol units; or they may be capable of being activated to form electroconduits; for example, photoactivatible species that can be selectively removed from the surface upon photoactivation, leaving electroconduits.

Preferred EFS include conductive oligomers, as defined below, and phenyl-acetylene-polyethylene glycol species, as well as asymmetrical SAM-forming disulfide species such as depicted in the figures of U.S. Ser. No. 60/145,912 filed Jul. 27, 1999, hereby expressly incorporated by reference. However, in some embodiments, the EFS is not a conductive oligomer.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping n-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^{4}$ $\Omega^{-1}$cm$^{-1}$, with from about $10^{-5}$ to about $10^{3}$ $\Omega^{-1}$cm$^{-1}$ being preferred, with these S values being calculated for molecules ranging from about 20 Å to about 200 Å. As described below, insulators have a conductivity S of about $10^{-7}$ $\Omega^{-1}$cm$^{-1}$ or lower, with less than about $10^{-8}$ $\Omega^{-1}$cm$^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during nucleic acid synthesis (such that nucleosides containing the conductive oligomers may be added to a nucleic acid synthesizer during the synthesis of the compositions of the invention), ii) during the attachment of the conductive oligomer to an electrode, or iii) during hybridization assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

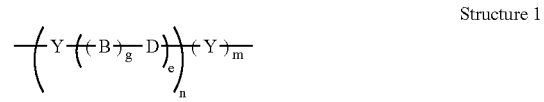

Structure 1

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a nucleic acid, the right "Y", if present, is attached to the nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a bond able to conjugate with neighboring bonds (herein referred to as a "conjugated bond"), preferably selected from acetylene, B-D is a conjugated bond, preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —$(O—CH_2—CH_2)_n$— group, although each carbon atom of the ethylene group may also be singly or doubly substituted, i.e. —$(O—CR_2—CR_2)_n$—, with R as described above. Ethylene glycol derivatives with other heteroatoms in place of oxygen (i.e. —$(N—CH_2—CH_2)_n$— or —$(S—CH_2—CH_2)_n$—, or with substitution groups) are also preferred.

Preferred substitution groups include, but are not limited to, methyl, ethyl, propyl, alkoxy groups such as —O—$(CH_2)_2$ $CH_3$ and —O—$(CH_2)_4$-$CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—) and other conjugated bonds such as (—CH=N—, —CR=N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®like oligomers, such as —(CF$_2$)$_n$—, —(CHF)$_r$— and —(CFR)$_n$—. See for example, Schumm et al., Angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

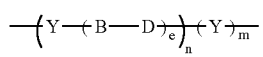

Structure 2

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

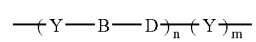

Structure 3

Preferred embodiments of Structure 3 are: Y is phenyl or substituted phenyl and B-D is azo; Y is phenyl or substituted phenyl and B-D is acetylene; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

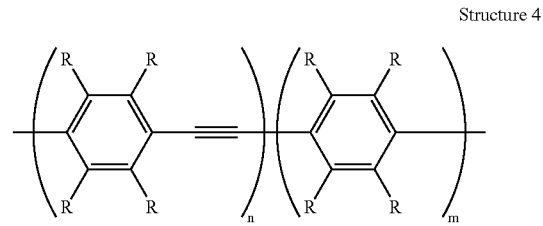

Structure 4

Particularly preferred embodiments of Structure 4 include: n is two, m is one, and R is hydrogen; n is three, m is zero, and R is hydrogen; and the use of R groups to increase solubility.

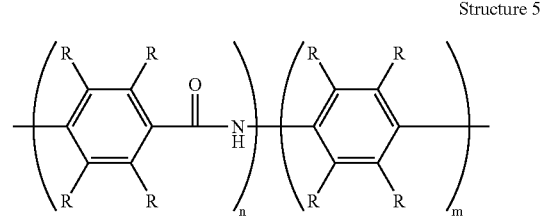

Structure 5

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

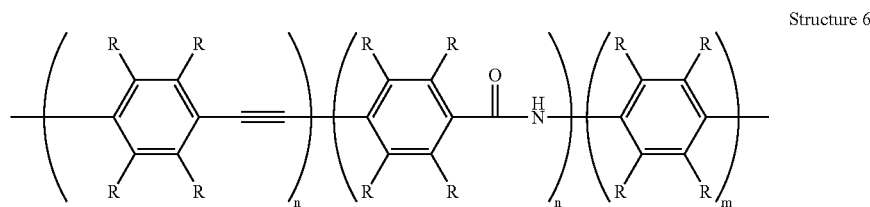

Structure 6

Preferred embodiments of Structure 6 include the first n is two, second n is one, m is zero, and all R groups are hydrogen, or the use of R groups to increase solubility.

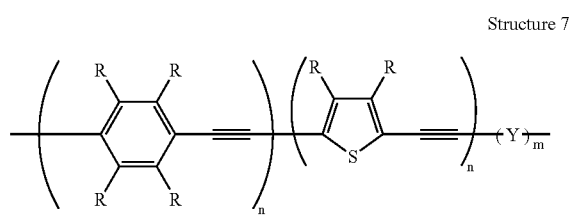

Structure 7

Preferred embodiments of Structure 7 include: the first n is three, the second n is from 1-3, with m being either 0 or 1, and the use of R groups to increase solubility.

In a preferred embodiment, the conductive oligomer has the structure depicted in Structure 8:

Structure 8

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not a n alkane bond.

In a preferred embodiment, the m of Structure 8 is zero. In a particularly preferred embodiment, m is zero and G is an alkene bond, as is depicted in Structure 9:

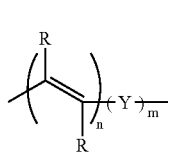

Structure 9

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

In addition, in some embodiments, the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in Structures 1 to 9; for example, a B-D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when nucleic acids are covalently attached to the electrode using conductive oligomers, it is possible to have one type of conductive oligomer used to attach the nucleic acid, and another type functioning to detect the ETM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer forming species are "interrupted" conductive oligomers, containing an alkyl portion in the middle of the conductive oligomer.

In a preferred embodiment, the monolayer comprises photoactivatable species as EFS. This general scheme is depicted in FIG. 11 of 09/626,096, incorporated by reference. Photoactivatable species are known in the art, and include 4,5-dimethoxy-2-nitrobenzyl ester, which can be photolyzed at 365 nm for 2 hours.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferrably slower than the rate through the conductive oligomers described herein.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, $-(CH_2)_n-$, $-(CRH)_n-$, and $-(CR_2)_n-$, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

In a preferred embodiment, the insulator species included in the SAM utilizes novel methods and compositions comprising asymmetric disulfides. As outlined herein, the signals generated from label probes can be dependent on the behavior or properties of the SAM. SAMs comprising "nanoconduits" or "electroconduits", as outlined in U.S. Ser. No. 60/145,912 hereby expressly incorporated herein by reference in its entirety, give good signals. Thus, the present invention provides asymmetric insulators based on disulfides, wherein one of the arms being a longer alkyl chain (or other SAM forming species) and the other arm comprising a bulky group, such as a branched alkyl group, that can be polar or nonpolar) for creating the nanoconduits. Two exemplary species are shown in FIGS. 31A and 31B of U.S. Ser. No. 60/145,912, with data shown in FIG. 31C. A variety of synthetic schemes are shown in FIG. 32. See also Mukaiyama Tetrahedron Lett. 1968, 5907; Boustany Tetrahedron Lett. 1970 3547; Harpp Tetrahedron Lett. 1970 3551; and Oae, J. Chem. Soc. Chem. Commun, 1977, 407, all of which are expressly incorporated herein by reference.

The length of the species making up the monolayer will vary as needed. As outlined above, it appears that hybridization is more efficient at a distance from the surface. The species to which nucleic acids are attached (as outlined below, these can be either insulators or conductive oligomers) may be basically the same length as the monolayer forming species or longer than them, resulting in the nucleic acids being more accessible to the solvent for hybridization. In some embodiments, the conductive oligomers to which the nucleic acids are attached may be shorter than the monolayer.

As will be appreciated by those in the art, the actual combinations and ratios of the different species making up the monolayer can vary widely, and will depend on whether mechanism-1 or -2 is used. Generally, either two or three component systems are preferred for mechanism-2 systems. Three component systems utilize a first species comprising a capture probe containing species, attached to the electrode via either an insulator or a conductive oligomer. The second species are conductive oligomers, and the third species are insulators. In this embodiment, the first species can comprise from about 90% to about 1%, with from about 20% to about 40% being preferred. For nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. To achieve these approximate proportions, preferred ratios of first:second:third species in SAM formation solvents are 2:2:1 for short targets, 1:3:1 for longer targets, with total thiol concentration (when used to attach these species, as is more fully outlined below) in the 500 µM to 1 mM range, and 833 µM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 or mechanism-2 systems, the two components are the first and the third species. In this embodiment, the first species can comprise from about 1% to about 90%, with from about 1% to about 40% being preferred, and from about 100% to about 40% being especially preferred. The second species can comprise from about 1% to about 90%, with from about 10% to about 60% being preferred, and from about 20% to about 40% being especially preferred.

In a preferred embodiment, the deposition of the SAM is done using aqueous solvents. As is generally described in Steel et al., Anal. Chem. 70:4670 (1998), Herne et al., J. Am. Chem. Soc. 119:8916 (1997), and Finklea, Electrochemistry of Organized Monolayers of Thiols and Related Molecules on Electrodes, from A. J. Bard, *Electroanalytical Chemistry: A Series of Advances*, Vol. 20, Dekker N.Y. 1966—, all of which are expressly incorporated by reference, the deposition of the SAM-forming species can be done out of aqueous solutions, frequently comprising salt.

The covalent attachment of the conductive oligomers and insulators may be accomplished in a variety of ways, depending on the electrode and the composition of the insulators and conductive oligomers used. In a preferred embodiment, the attachment linkers with covalently attached nucleosides or nucleic acids as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 11-13. Generally, some type of linker is used, as depicted below as "A" in Structure 10, where "X" is the conductive oligomer, "I" is an insulator and the hatched surface is the electrode:

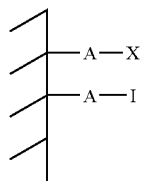

Structure 10

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

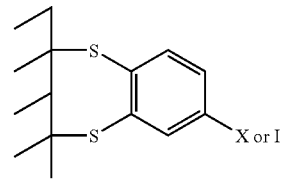

Structure 11

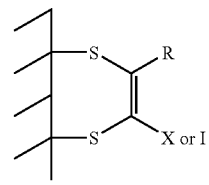

Struture 12

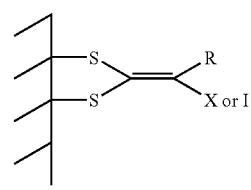

Structure 13

It should also be noted that similar to Structure 13, it may be possible to have a conductive oligomer terminating in a single carbon atom with three sulfur moities attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups). In addition, Structure 14 shows the sulfur atom attached to the Y aromatic group, but as will be appreciated by those in the art, it may be attached to the B-D group (i.e. an acetylene) as well.

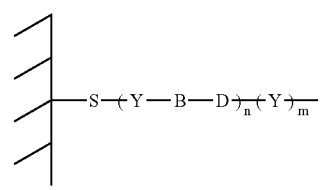

Structure 14

In a preferred embodiment, the electrode is a carbon electrode, i.e. a glassy carbon electrode, and attachment is via a nitrogen of an amine group. Are representative structure is depicted in Structure 15. Again, additional atoms may be present, i.e. Z type linkers and/or terminal groups.

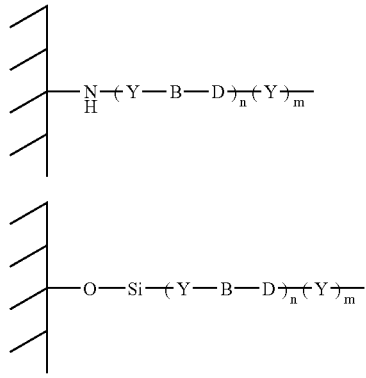

Structure 15

Structure 16

In Structure 16, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one preferred embodiment, indium-tin-oxide (ITO) is used as the electrode.

In a preferred embodiment, a gold surface is first cleaned. A variety of cleaning procedures may be employed, including, but not limited to, chemical cleaning or etchants (including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. A preferred embodiment utilizes a deposition solution comprising a mixture of various SAM species in solution, generally thiol-containing species. Mixed monolayers that contain nucleic acids are usually prepared using a two step procedure. The thiolated nucleic acid is deposited during the first deposition step (generally in the presence of at least one other monolayer-forming species) and the mixed monolayer formation is completed during the second step in which a second thiol solution minus nucleic acid is added. Optionally, a second step utilizing mild heating to promote monolayer reorganization.

In a preferred embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 μM to 10 mM, with from about 400 uM to about 1.0 mM being especially preferred. In a preferred embodiment, the deposition solution contains thiol modified DNA (i.e. nucleic acid attached to an attachment linker) and thiol diluent molecules (either conductive oligomers or insulators, with the latter being preferred). The ratio of nucleic acid to diluent (if present) is usually between 1000:1 to 1:1000, with from about 10:1 to about 1:10 being preferred and 1:1 being especially preferred. The preferred solvents are tetrahydrofuran (THF), acetonitrile, dimethylforamide (DMF), ethanol, or mixtures thereof; generally any solvent of sufficient polarity to dissolve the capture ligand can be used, as long as the solvent is devoid of functional groups that will react with the surface. Sufficient nucleic acid deposition solution is added to the vial so as to completely cover the electrode surface. The gold substrate is allowed to incubate at ambient temperature or slightly above ambient temperature for a period of time ranging from seconds to hours, with 5-30 minutes being preferred. After the initial incubation, the deposition solution is removed and a solution of diluent molecule only (from about 1 μM to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In a preferred embodiment, an aqueous deposition solution is used. As above, a clean gold surface is placed into a clean vial. A nucleic acid deposition solution in water is prepared in which the total thiol concentration is between about 1 uM and 10 mM, with from about 1 μM to about 200 uM being preferred. The aqueous solution frequently has salt present (up to saturation, with approximately 1 M being preferred), however pure water can be used. The deposition solution contains thiol modified nucleic acid and often a thiol diluent molecule. The ratio of nucleic acid to diluent is usually between between 1000:1 to 1:1000, with from about 10:1 to about 1:10 being preferred and 1:1 being especially preferred. The nucleic acid deposition solution is added to the vial in such a volume so as to completely cover the electrode surface. The gold substrate is allowed to incubate at ambient temperature or slightly above ambient temperature for 1-30 minutes with 5 minutes usually being sufficient. After the initial incubation, the deposition solution is removed and a solution of diluent molecule only (10 uM-1.0 mM) in either water or organic solvent is added. The gold substrate is allowed to incubate at room temperature or above room temperature until a complete monolayer is formed (10 minutes-24 hours). The gold sample is removed from the solution, rinsed in clean solvent and used.

In a preferred embodiment, the deposition solution comprises a zwitterionic compound, preferably betaine. Preferred embodiments utilize betaine and Tris-HCl buffers.

In a preferred embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 µM size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then optionally treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen. Preferrably, only the water rinse is employed.

In a preferred embodiment, the detection electrode comprising the SAM (or the sites on the array, for non-electrode embodiments) further comprises capture binding ligands, preferably covalently attached. By "binding ligand" or "binding species" herein is meant a compound that is used to probe for the presence of the target analyte, that will bind to the target analyte. In general, for most of the embodiments described herein, there are at least two binding ligands used per target analyte molecule; a "capture" or "anchor" binding ligand (also referred to herein as a "capture probe", particularly in reference to a nucleic acid binding ligand) that is attached to the detection electrode as described herein, and a soluble binding ligand (frequently referred to herein as a "signaling probe" or a "label probe"), that binds independently to the target analyte, and either directly or indirectly comprises at least one ETM. However, it should be noted that for fluorescence-based nucleic acid detection systems, the target sequence is generally amplified, and during amplification, a fluorescent label is added; thus these systems generally comprise only two elements, the capture probe and the labeled target. Again, the discussion below is directed to the use of electrodes and electrochemical detection, but as will be appreciated by those in the art, fluorescent based systems can be used as well.

Generally, the capture binding ligand allows the attachment of a target analyte to the detection electrode, for the purposes of detection. As is more fully outlined below, attachment of the target analyte to the capture binding ligand may be direct (i.e. the target analyte binds to the capture binding ligand) or indirect (one or more capture extender ligands may be used).

In a preferred embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding that is not highly specific; for example, the systems may use different binding ligands, for example an array of different ligands, and detection of any particular analyte is via its "signature" of binding to a panel of binding ligands, similar to the manner in which "electronic noses" work. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-6}$ $M^{-1}$, with at least about $10^{-5}$ to $10^{-9}$ being preferred and at least about $10^7$ to $10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include peptides. For example, when the analyte is an enzyme, suitable binding ligands include substrates, inhibitors, and other proteins that bind the enzyme, i.e. components of a multienzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors. Similarly, there is a wide body of literature relating to the development of binding partners based on combinatorial chemistry methods.

In this embodiment, when the binding ligand is a nucleic acid, preferred compositions and techniques are outlined in U.S. Pat. Nos. 5,591,578; 5,824,473; 5,705,348; 5,780,234 and 5,770,369; U.S. Ser. Nos. 08/873,598 08/911,589; WO 98/20162; WO98/12430; WO98/57158; WO 00/16089) WO99/57317; WO99/67425; WO00/24941; PCT US00/10903; WO00/38836; WO99/37819; WO99/57319 and PCTUS00/20476; and related materials, all of which are expressly incorporated by reference in their entirety.

The method of attachment of the capture binding ligands to the attachment linker (either an insulator or conductive oligomer) will generally be done as is known in the art, and will depend on both the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or indirectly through the use of a linker, sometimes depicted herein as "Z". Linkers are well known in the art; for example, homo-or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages.

In this way, capture binding ligands comprising proteins, lectins, nucleic acids, small organic molecules, carbohydrates, etc. can be added.

A preferred embodiment utilizes proteinaceous capture binding ligands. As is known in the art, any number of techniques may be used to attach a proteinaceous capture binding ligand to an attachment linker. A wide variety of techniques are known to add moieties to proteins.

A preferred embodiment utilizes nucleic acids as the capture binding ligand. While most of the following discussion focuses on nucleic acids, as will be appreciated by those in the art, many of the techniques outlined below apply in a similar manner to non-nucleic acid systems as well, and to systems that rely on attachment to surfaces other than metal electrodes.

The capture probe nucleic acid is covalently attached to the electrode, via an "attachment linker", that can be either a conductive oligomer (required for mechanism-1 systems) or an insulator. By "covalently attached" herein is meant that two moieties are attached by at least one bond, including sigma bonds, pi bonds and coordination bonds.

Thus, one end of the attachment linker is attached to a nucleic acid (or other binding ligand), and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 17:

attachment linker may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs, and in some cases with other binding ligands. Similarly, most of the structures herein depict conductive oligomers as the attachment linkers, but insulators such as alkyl chains are preferred in many embodiments.

In a preferred embodiment, the attachment linker is attached to the base of a nucleoside of the nucleic acid. This may be done in several ways, depending on the linker, as is described below. In one embodiment, the linker is attached to a terminal nucleoside, i.e. either the 3' or 5' nucleoside of the nucleic acid. Alternatively, the linker is attached to an internal nucleoside.

The point of attachment to the base will vary with the base. Generally, attachment at any position is possible. In some embodiments, for example when the probe containing the ETMs may be used for hybridization (i.e. mechanism-1 systems), it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the attachment linker and the base. In this embodiment, for example, attachment linkers comprising conductive oligomers with terminal acetylene bonds are attached directly to the base. Structure 18 is an example of this linkage, using a Structure 3 conductive oligomer and uridine as the base, although other bases and attachment linkers can be used as will be appreciated by those in the art:

Structure 17

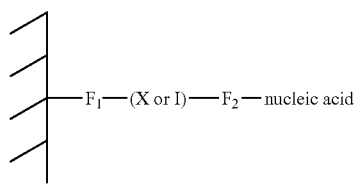

Structure 18

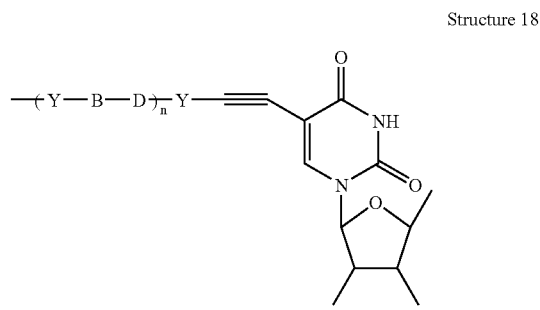

In Structure 17, the hatched marks on the left represent an electrode. X is a conductive oligomer and is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogeneous to both, for example, as defined herein for "Z".

In a preferred embodiment, the capture probe nucleic acid is covalently attached to the electrode via an attachment linker. The covalent attachment of the nucleic acid and the It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected.

In an alternative embodiment, the attachment is any number of different Z linkers, including amide and amine linkages, as is generally depicted in Structure 19 using uridine as the base and a Structure 3 oligomer as the attachment linker:

Structure 19:

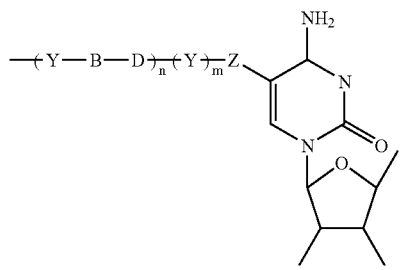

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo-or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the attachment linker is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the attachment linker is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6): 1329 (1995), all of which are incorporated by reference). These modified nucleosides are then used to add the attachment linkers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1-3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer as the attachment linker):

Structure 20

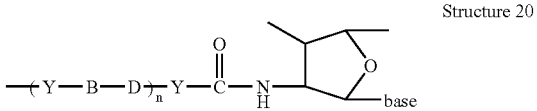

As will be appreciated by those in the art, Structure 20 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, as the attachment linkers, using the nitrogen as the heteroatom, although other heteroatoms can be used:

Structure 21

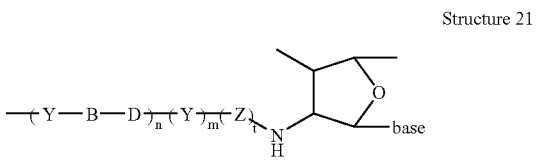

In Structure 21, preferably both m and t are not zero. A preferred Z here is a methylene group, or other aliphatic alkyl linkers. One, two or three carbons in this position are particularly useful for synthetic reasons.

Structure 22

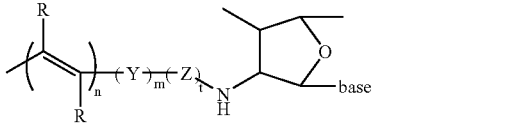

In Structure 22, Z is as defined above. Suitable linkers include methylene and ethylene.

In an alternative embodiment, the attachment linker is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible as well as any number of other attachment linkers). Structures 23 and 24 depict the conductive oligomer in the 3' position, although the 5' position is also possible. Furthermore, both Structures 23 and 24 depict naturally occurring phosphodiester bonds, although as those in the art will appreciate, non-standard analogs of phosphodiester bonds may also be used.

Structure 23

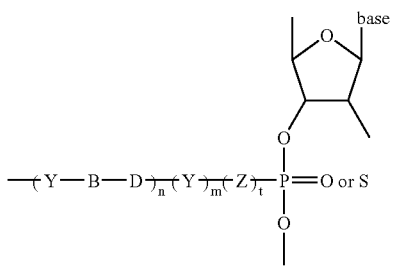

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B-D bond is an amide bond, the terminal Y is not present, and Z is a linker, as defined herein.

Structure 24

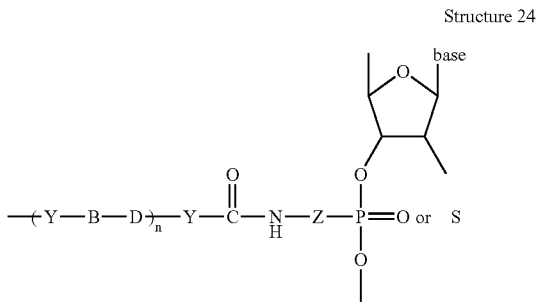

In a preferred embodiment, the attachment linker is covalently attached to the nucleic acid via a transition metal ligand. In this embodiment, the attachment linker is covalently attached to a ligand which provides one or more of the coordination atoms for a transition metal. In one embodiment, the ligand to which the attachment linker is attached also has the nucleic acid attached, as is generally depicted below in Structure 25. Alternatively, the attachment linker is attached to one ligand, and the nucleic acid is attached to another ligand, as is generally depicted below in Structure 26. Thus, in the presence of the transition metal, the attachment linker is covalently attached to the nucleic acid. Both of these structures depict Structure 3 conductive oligomers, although other attachment linkers may be utilized. Structures 25 and 26 depict two representative structures:

Structure 25

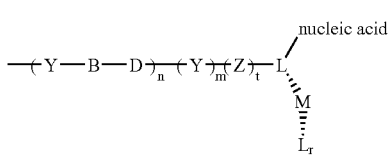

Structure 26

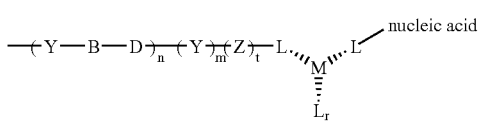

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2', 3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyaide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substitutents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjuction with other n-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the attachment linker is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

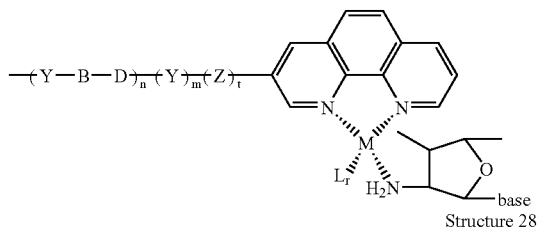

Structure 28

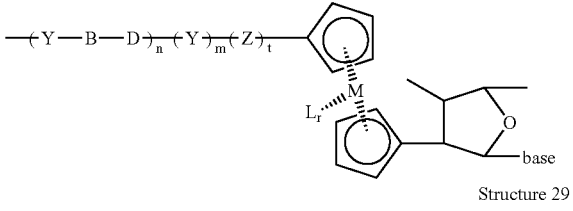

Structure 29

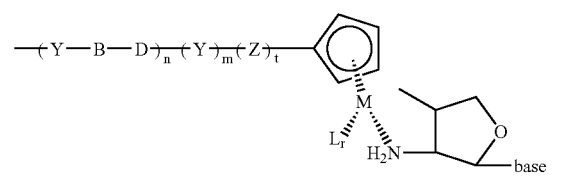

Again, other attachment linkers such as alkyl groups may also be utilized.

In a preferred embodiment, the ligands used in the invention show altered fluoroscent properties depending on the redox state of the chelated metal ion. As described below, this thus serves as an additional mode of detection of electron transfer between the ETM and the electrode.

In addition, similar methods can be used to attach proteins to the detection electrode; see for example U.S. Pat. No. 5,620,850, hereby incorporated by reference.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

In a preferred embodiment, the capture probe nucleic acids (or other binding ligands) are covalently attached to the electrode via an insulator (e.g. the attachment linker is an insulator). The attachment of nucleic acids (and other binding ligands) to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface. In some embodiments, there may be one type of capture probe, or one type of capture probe extender, as is more fully described below. Alternatively, different capture probes, or one capture probes with a multiplicity of different capture extender probes can be used. Similarly, it may be desirable (particular in the case of nucleic acid analytes and binding ligands in mechanism-2 systems) to use auxiliary capture probes that comprise relatively short probe sequences, that can be used to "tack down" components of the system, for example the recruitment linkers, to increase the concentration of ETMs at the surface.

In a preferred embodiment, a number of capture probes are designed and used for each target sequence. That is, a single electrode pad of the array may have 1 probe to the target analyte, or a plurality of probes to the same target sequence, preferably (but not required to be) non-overlapping. This is particularly preferred for long target sequences. In this embodiment, at least two different capture probes are used, with at least 3, 4, 5, 6, 7, 8, 9 or 10 being preferred, and 8 being particularly preferred.

Thus the present invention provides substrates comprising at least one detection electrode comprising monolayers and capture binding ligands, useful in target analyte detection systems.

In a preferred embodiment, the compositions further comprise a solution or soluble binding ligand, although as is more fully described below, for mechanism-1 systems, the ETMs may be added in the form of non-covalently attached hybridization indicators. Solution binding ligands are similar to capture binding ligands, in that they bind, preferably specifically, to target analytes. The solution binding ligand (generally referred to herein as label probes when the target analytes are nucleic acids) may be the same or different from the capture binding ligand. Generally, the solution binding ligands are not directly attached to the surface. The solution binding ligand either directly comprises a recruitment linker that comprises at least one ETM (FIG. 4A from 60/190,259), or the recruitment linker binds, either directly (FIG. 4A) or indirectly (FIG. 4E), to the solution binding ligand.

Thus, "solution binding ligands" or "soluble binding ligands" or "signal carriers" or "label probes" or "label binding ligands" with recruitment linkers comprising covalently attached ETMs are provided.

That is, one portion of the label probe or solution binding ligand directly or indirectly binds to the target analyte, and one portion comprises a recruitment linker comprising covalently attached ETMs. In some systems, for example in mechanism-1 nucleic acid systems, these may be the same. Similarly, for mechanism-1 systems, the recruitment linker comprises nucleic acid that will hybridize to detection probes. The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention.

Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention are listed above.

The transition metals are complexed with a variety of ligands, L, defined above, to form suitable transition metal complexes, as is well known in the art.

Preferred ETMs comprise metallocenes, particularly ferrocene.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7diazapyrenium dichloride ($DAP^{2+}$), methylviologen, ethidium bromide, quinones such as N,N'-dimethylanthra(2,1,9-def:6,5,10-d'e'f') diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. Preferred ETMs are metallocenes, with ferrocene being particularly preferred.

Accordingly, the present invention provides methods and compositions useful in the detection of nucleic acids and other target analytes. As will be appreciated by those in the art, the compositions of the invention can take on a wide variety of configurations. As is more fully outlined below, preferred systems of the invention work as follows. A target nucleic acid sequence is attached (via hybridization) to an electrode comprising a monolayer, generally including conductive oligomers. This attachment can be either directly to a capture probe on the surface, or indirectly, using capture extender probes. In some embodiments, the target sequence itself comprises the ETMs. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex. As a result of the hybridization of the first portion of the label probe, the second portion of the label probe, the "recruitment linker", containing the ETMs is brought into spatial proximity to SAM surface on the electrode, and the presence of the ETM can then be detected electronically.

Thus, in a preferred embodiment, the present invention provides electrodes comprising monolayers comprising SAM forming species and capture probes, useful in nucleic acid (or other target analyte) detection systems. In a preferred embodiment, the compositions further comprise a label probe. The label probe is nucleic acid, generally single stranded, although as more fully outlined below, it may contain double-stranded portions. In mechanism-2 systems, the label probe comprises a first portion that is capable of hybridizing to a component of the assay complex, defined below, and a second portion that does not hybridize to a component of an assay complex and comprises at least one covalently attached ETM.

Without being bound by theory, it appears that in "mechanism-2" systems, electron transfer is facilitated when the ETM is able to penetrate ("snuggle") into the monolayer to some degree. That is, in general, it appears that hydrophobic ETMs used with hydrophobic SAMs give rise to better (greater) signals than ETMs that are charged or more hydrophilic. Thus, for example, ferrocene in solution can penetrate the monolayers of the examples and give a signal when electroconduits are present, while ferrocyanide in solution gives little or no signal. Thus, in general, hydrophobic ETMs are preferred in mechanism-2 systems; however, transition metal complexes, although charged, with one or more hydrophobic ligands, such as Ru and Os complexes, also give rise to good signals. Similarly, electron transfer between the ETM and the electrode is facilitated by the use of linkers or spacers that allow the ETM some flexibility to penetrate into the monolayer; thus the N6 compositions of the invention have a four carbon linker attaching the ETM to the nucleic acid.

In a preferred embodiment, a plurality of ETMs are used. The use of multiple ETMs provides signal amplification and thus allows more sensitive detection limits. As discussed below, while the use of multiple ETMs on nucleic acids that hybridize to complementary strands can cause decreases in $T_m$s of the hybridization complexes depending on the number, site of attachment and spacing between the multiple ETMs, this is not a factor when the ETMs are on the recruitment linker, since this does not hybridize to a complementary sequence. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (100 to 1000) can be used.

As will be appreciated by those in the art, the portion of the label probe (or target, in some embodiments) that comprises the ETMs (termed herein a "recruitment linker" or "signal carrier") can be nucleic acid, or it can be a non-nucleic acid linker that links the first hybridizable portion of the label probe to the ETMs. That is, since this portion of the label probe is not required for hybridization, it need not be nucleic acid, although this may be done for ease of synthesis. In some embodiments, as is more fully outlined below, the recruitment linker may comprise double-stranded portions. Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups. These options are generally depicted in the Figures.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIG. 16H of U.S. Ser. No. 60/190,259 this is similar to the use of an amplifier probe, except that both the primary and the secondary label probes comprise ETMs.

In a preferred embodiment, the ETM is attached to the base of a nucleoside as is generally outlined above for attachment of the attachment linkers. Attachment can be to an internal nucleoside or a terminal nucleoside.

The covalent attachment to the base will depend in part on the ETM chosen, but in general is similar to the attachment of conductive oligomers to bases, as outlined above. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between $sp^2$ and sp Carbon Centers, Sonogashira, pp 521-549, and pp 950-953, hereby incorporated by reference). Structure 30 depicts a representative structure in the presence of the metal ion and any other necessary ligands; Structure 30 depicts uridine, although as for all the structures herein, any other base may also be used.

Structure 30

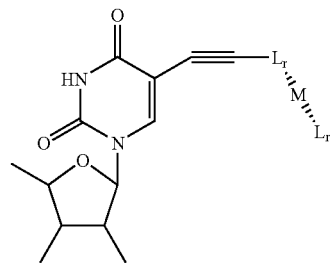

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the attachment linkers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 31, which again uses uridine as the base, although as above, the other bases may also be used:

Structure 31

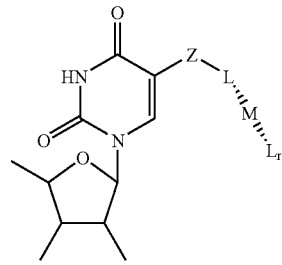

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and $L_r$ of Structure 31 are both metallocene ligands, $L_m$, as described above. Structure 32 depicts a preferred embodiment wherein the metallocene is ferrocene, and the base is uridine, although other bases may be used:

Structure 32

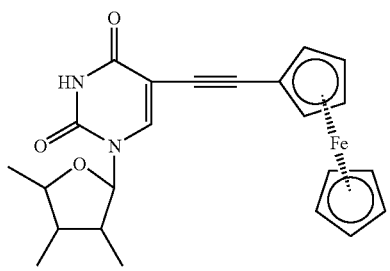

Preliminary data suggest that Structure 32 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 may be replaced by ETMs; alternatively, the ETMs may be added to the free terminus of the conductive oligomer.

In a preferred embodiment, a metallocene serves as the ETM, and is attached via an amide bond as depicted below in Structure 33. The examples outline the synthesis of a preferred compound when the metallocene is ferrocene.

Structure 33

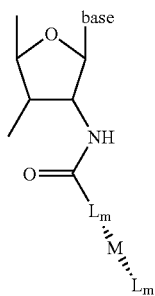

In a preferred embodiment, amine linkages are used, as is generally depicted in Structure 34.

Structure 34

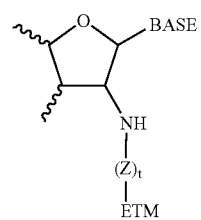

Z is a linker, as defined herein, with 1-16 atoms being preferred, and 2-4 atoms being particularly preferred, and t is either one or zero.

In a preferred embodiment, oxo linkages are used, as is generally depicted in Structure 35.

Structure 35

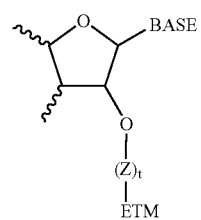

In Structure 35, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in Structures 23 and 24 may be replaced by ETMs. In a preferred embodiment, the composition has the structure shown in Structure 36.

Structure 36

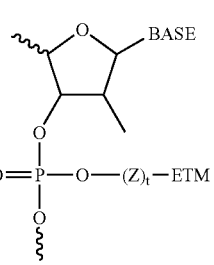

In Structure 36, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

When the ETM is attached to the base or the backbone of the nucleoside, it is possible to attach the ETMs via "dendrimer" structures, as is more fully outlined below. As is generally depicted in the Figures, alkyl-based linkers can be used to create multiple branching structures comprising one or more ETMs at the terminus of each branch (although internal ETMs can be used as well). Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions. The branch point can be an internal one or a terminal one, and can be a chemical branch point or a nucleoside branch point.

In a preferred embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 37 (nucleic acid with a ribose-phosphate backbone) and Structure 38 (peptide nucleic acid backbone). Structures 37 and 38 depict ferrocene, although as will be appreciated by those in the art, other metallocenes may be used as well. In general, air stable metallocenes are preferred, including metallocenes utilizing ruthenium and cobalt as the metal.

Structure 37

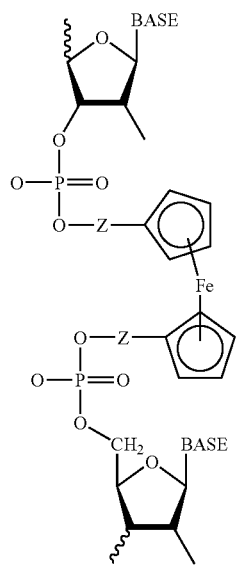

Structure 38

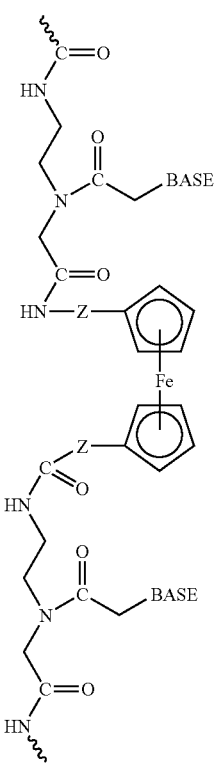

In Structure 37, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 37 depicts a ribose-phosphate backbone, although as will be appreciated by those in the art, nucleic acid analogs may also be used, including ribose analogs and phosphate bond analogs.

In Structure 38, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as A nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substitutent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substitutent groups include, but are not limited to, amide groups, amine groups, carboxylic acids, and alcohols, including substituted alcohols. In addition, these substitutent groups can be attached via linkers as well, although in general this is not preferred.

In addition, substitutent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 39:

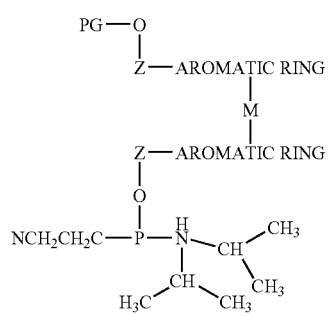

Structure 39

In Structure 39, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein. Structure 40 depicts the ferrocene derivative:

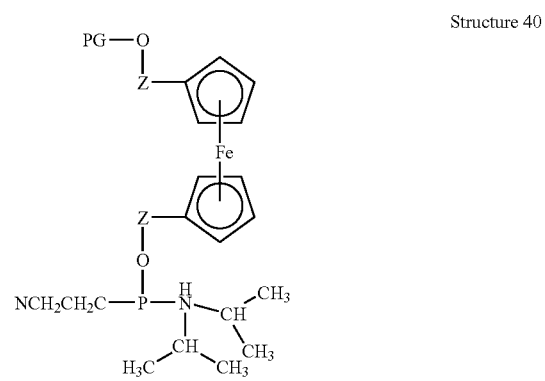

Structure 40

These phosphoramidite analogs can be added to standard oligonucleotide syntheses as is known in the art.

Structure 41 depicts the ferrocene peptide nucleic acid (PNA) monomer, that can be added to PNA synthesis as is known in the art:

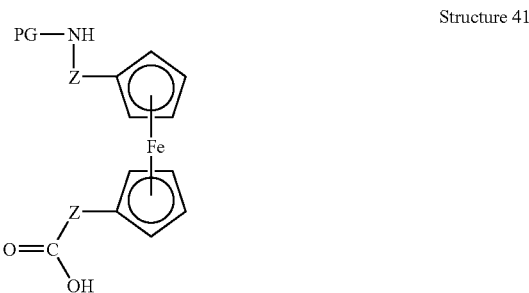

Structure 41

In Structure 41, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, the ETMs are attached as polymers, for example as metallocene polymers, in a "branched" configuration similar to the "branched DNA" embodiments herein and as outlined in U.S. Pat. No. 5,124, 246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 39 and 40, ETMs, such as metallocene ETMs, are added. Additional phosphoramidite ETMs such as metallocenes can be added, to form "ETM polymers", including "metallocene polymers" as depicted herein, particularly for ferrocene. In addition, in some embodiments, it is desirable to increase the solubility of the polymers by adding a "capping" group to the terminal ETM in the polymer, for example a final phosphate group to the metallocene as is generally depicted in FIG. 12. Other suitable solubility enhancing "capping" groups will be appreciated by those in the art. It should be noted that these solubility enhancing groups can be added to the polymers in other places, including to the ligand rings, for example on the metallocenes as discussed herein In a preferred embodiment, (as depicted in the figures of U.S. Ser. No. 09/626,096) the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 41, peptide nucleic acid structures containing metallocene polymers could be generated.

Thus, the present invention provides recruitment linkers of nucleic acids comprising "branches" of metallocene polymers as is generally depicted in FIGS. 12 and 13. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo-or hetero-bifunctional linkers as are well known (see 1994 Pierce Chemical Company catalog, technical section on cross-linkers, pages 155-200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

The attachment of the recruitment linkers to the first portion of the label probe will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, it is the target sequence itself that carries the ETMs, rather than the recruitment linker of a label probe. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs, as is generally depicted in FIGS. 16A, 16B and 16D of U.S. Ser. No. 60/190,259.

Alternatively, as outlined more fully below, it is possible to enzymatically add nucleotides comprising ETMs to the terminus of a nucleic acid, for example a target nucleic acid. In this embodiment, an effective "recruitment linker" is added to the terminus of the target sequence, that can then be used for detection. Thus the invention provides compositions utilizing electrodes comprising monolayers of conductive oligomers and capture probes, and target sequences that comprises a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, i.e. sequences designed to hybridize to complementary sequences. Thus, ETMs may be added to non-recruitment linkers as well. For example, there may be ETMs added to sections of label probes that do hybridize to components of the assay complex, for example the first portion, or to the target sequence as outlined above. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIG. 16A of U.S. Ser. No. 60/190,259, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In one embodiment, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317-2323 (1993); Millan et al., Anal. Chem. 662943-2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers. Hybridization indicators include intercalators and minor and/or major groove binding moieties. In a preferred embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., Bioconj. Chem. 8:906 (1997), hereby expressly incorporated by reference. In this embodiment, changes in the redox state of certain molecules as a result of the presence of DNA (i.e. guanine oxidation by ruthenium complexes) can be detected using the SAMs comprising conductive oligomers as well.

Thus, the present invention provides electrodes comprising monolayers comprising conductive oligomers, generally including capture probes, and either target sequences or label probes comprising recruitment linkers containing ETMs. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

Generally, the nucleic acid compositions of the invention are useful as oligonucleotide probes. As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200-300 nucleotides in length. Thus, in the structures depicted herein, nucleosides may be replaced with nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al., hereby incorporated by reference. The hybridization conditions may also vary when a non-ionic backbone, i.e. PNA is used, as is known in the art. In addition, cross-linking agents may be added after target binding to cross-link, i.e. covalently attach, the two strands of the hybridization complex.

As will be appreciated by those in the art, the systems of the invention may take on a large number of different configurations, as is generally depicted in the Figures of U.S. Ser. No. 09/626,096 (the Figures in the next paragraphs refer to the figures of U.S. Ser. No. 09/626,096). In general, there are three types of systems that can be used: (1) systems in which the target sequence itself is labeled with ETMs (see FIGS. 16A, 16B and 16D); (2) systems in which label probes directly hybridize to the target sequences (see FIGS. 16C and 16H); and (3) systems in which label probes are indirectly hybridized to the target sequences, for example through the use of amplifier probes (see FIGS. 16E, 16F and 16G).

In general, for all the systems outlined herein, both for nucleic acids and other target analytes, the invention provides assay complexes that minimally comprise a target analyte and a capture binding ligand. For nucleic acid target sequences, by "assay complex" herein is meant the collection of hybridization complexes comprising nucleic acids, including probes and targets, that contains at least one label (preferably an ETM in the electronic methods of the present invention) and thus allows detection. The composition of the assay complex depends on the use of the different probe component outlined herein. The assay complexes may also include label probes, capture extender probes, label extender probes, and amplifier probes, as outlined herein and in U.S. Ser. No. 09/626,096, depending on the configuration used.

The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Accordingly, the present invention provides biochips, with covalently attached capture binding ligands (e.g. capture probes). The biochips are incorporated into the cartridges of the invention and then fitted into the stations of the multiplexing devices of the invention for running assays.

In a preferred embodiment, the biochips are attached to the rest of the cartridge in a wide variety of ways. In one embodiment, the biochip is made directly on a portion of the cartridge and is thus incorporated into the system. Alternatively, as outlined herein, when the biochip is formulated on a different substrate than the remainder of the cartridge, there are a variety of attachment mechanisms that can be used, depending on the composition and configuration of the two substrates. For example, when the biochip is formulated on printed circuit board material, there can be "pins" or "rods" that are inserted into holes, with subsequent fusion (for example, using solvents or heat). Similarly, surface-to-surface heat or solvent fusion may be done. Alternatively, adhesives can be used to glue the two together. Similarly, these techniques can be used with additional sealing components such as gaskets. Alternatively, the biochip may "snap" into the cartridge, using components such as molded plastic snapping devices.

The present invention further provides for holders for the cartridges for loading with samples, prior to loading the cartridges into the stations of the device. In general, as will be appreciated by those in the art, the holders may be configured in a wide variety of ways, depending on the configuration of the cartridges and caps, if present. For example, holders that align cartridges such that standard reagent handling tools can be used are preferred. As shown in the Figures, holders that allow the use of multichannel pipettemen or robotic systems based on 96 well formats are preferred. The holders may also include the caps, positioned for easy use, or reagents and/or buffer components. In general, the holders are fabricated out of materials resistant to the chemicals and reagents used in the assays.

The cartridges of the invention are designed to be inserted into stations in a multiplexing device. As will be appreciated by those in the art and described below, the devices of the invention can take on a wide variety of conformations, depending on the desired components, the end use, the ultimate desired size of the instrument, etc.

Each multiplexing device has a number of different stations into which the cartridges are inserted. The cartridge/station pair can be configured in a variety of ways to include the use of "snap-in" locks, asymmetry such that the cartridge only fits into the device in a particular orientation, different size stations for different size cartridges (for example, some rare amount of tests may require special handling and the machines may be designed with special stations for these tests). This embodiment may also utilize electronic sensors that detect the presence or absence of a cartridge, or whether the cartridge is correctly positioned.

In general, the number of stations per device will vary with the desired use. Preferred embodiments utilize at least two or three stations, with at least 5-100 being preferred, and from about 25-50 being particularly preferred, with 48 being especially preferred. In general, the devices are laid out as a matrix, with columns and rows of stations.

As outlined herein, each station can have a number of different functional components, including, but not limited to, interconnects to electronic components, thermocontrollers, signaling systems, sensors for leak detection, alphanumeric displays, and detectors.

In a preferred embodiment, when the cartridge comprises a biochip that relies on electrodes for detection, the stations comprise matching interconnects for the biochip, to allow electronic communication between the chip and the device.

In a preferred embodiment, each station comprises an individual thermal controller. "Thermal controller" or "thermocontroller" in this context includes elements that can both heat and cool the cartridges and thus the samples in the cartridges as well. In general, given the size and function of the systems, it is desirable to utilize small, fast thermocontrollers. There are a wide variety of known suitable thermocontrollers, including Peltier systems.

In general, the thermocontroller should be able to heat/cool samples ranging from 0 to about 100° C. and at a rate ranging from 0.01° C./sec to 10° C./sec.

It should be noted that a thermocontroller can be used after an assay to destroy the biological material in the cartridge. That is, it is frequently desirable to minimize the exposure of health care workers and lab workers to potentially dangerous samples, and to facilitate the disposal of these materials. The thermocontroller can be used to heat the spent sample at extreme temperatures for some period of time in order to kill or destroy the sample. In addition, heating in conjunction with the addition of other generally harsh reagents (strong acid, strong base, etc.) can also be used. Furthermore, in some embodiments, an RF antennae is used to generate plasma that is pumped into the chamber after fluid evacuation to destroy all biological material.

In one embodiment, rather than each station comprising an individual thermal controller, sets (for example, rows or columns) of the stations share a thermal controller. In an alternative embodiment, the multiplexing device comprises a single thermal controller.

In a preferred embodiment, the devices of the invention include a "Stat Slot", where a cartridge can be put in and read right away at one station, rather than run as a sequence. In general, the temperature at this station may be preset.

In a preferred embodiment, the stations of the device include signaling systems. For example, a system of lights, particularly colored lights, at each station can be used to indicate the status of the cartridge or the assay: cartridge present or absent, assay in progress, error, assay completed, etc. In addition, the configuration of the lights may be the code (particularly for color blind people); two lights for cartridge in, flashing lights for assay finished, etc. Again, these signaling systems may be at each station or at sets of stations.

In a preferred embodiment, the devices of the invention including an alphanumeric display to allow the display of data or other information. For example, this display may be used in conjunction with a barcode reader, described below, to show the operator which cartridge was inserted (e.g. the HIV panel, the HCV panel, the infectious disease panel, the breast cancer SNP panel, etc.), or other data about the cartridge (lot or batch number, etc.). In addition, the display can be used to give the operator the test results, etc. As for the signaling systems, a display can be at each station, or there may be displays for sets of stations or for the whole device.

In a preferred embodiment, each station of the device may be configured to allow electrophoresis or dielectrophoresis on the biochip. That is, as is generally described in WO99/67425 and U.S. Ser. No. 09/171,981, hereby incorporated by reference, there may be additional electrodes or electronic components to allow the concentration and/or movement of analytes to the surface of the array.

Similarly, as is described in WO99/67425 and U.S. Ser. No. 09/171,981, the electrophoresis or dielectrophoresis electrodes may be contained on the biochip.

In a preferred embodiment, the device (or alternatively, each station) comprises a barcode reader to read a corresponding barcode on the cartridge. These barcodes may be used for a wide variety of purposes, including, but not limited to, identifying the sample (e.g. patient number or code), the test being done, the batch number of the chip, calibration information, assay protocols including cycle time, signal processing requirements, etc.

In addition, the barcode can be used to control the instrument. For example, instrument control may be through the use of a keyboard, a mouse or a barcode reader. Thus, for example, there may be barcodes on the cartridges to indicate the identity of the chip, but also on a card to scan for starting the assay, stopping the assay, downloading the data, etc. In a preferred embodiment, the card of barcode commands are found in the drawer of the device, outlined herein.

In a preferred embodiment, each station comprises a memory chip reader. Again, in this embodiment, each cartridge comprises a memory chip, that can have sample information (e.g. patient number or code), the test being done, the batch number of the chip, calibration information, assay protocols, etc.), or what the user interface looks like (for example, not a number but "HIV positive"), etc.

In a preferred embodiment, each station comprises a memory chip writer to add information to the cartridge, such as what test was done, the date, the results, etc.

In a preferred embodiment, each station has encryption components in conjunction with the cartridge, to encrypt patient information. That is, there is a growing concern regarding the confidentiality of patient information, particularly with regard to employment and insurance issues. Thus for example, in some embodiments, the devices of the invention will not allow the operator to know the results of the test. Rather, the output will be a confirmation that the test was performed correctly and a viable answer received, but nothing as to the actual test being done or the results. The test results themselves, in addition to the patient information, can be encrypted and sent to a remote location as outlined below for processing, decryption or storage.

In a preferred embodiment, the device may include drawers or storage compartments to allow the storage of reagents, cartridges, caps, holders, pipettemen, etc.

In a preferred embodiment, for example, when fluorescence dyes are used in the assays, fluorescent readers are used. In one embodiment, the device comprises a reader at each station. Alternatively, in a preferred embodiment, the device comprises a single reader that is moved, either by moving the reader or by moving the stations to a single reader within the device. Thus, in some embodiments, there are motors, pulleys, cords, etc. to allow the movement of stations, cartridges or readers.

In a preferred embodiment, the devices of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.; this is in addition to or in place of the station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, for example when electronic detection is not done, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluoroescence resonance energy transfer (FRET), luminescence, quenching, two-photon excitation, and intensity redistribution; CCD cameras to capture and transform data and images into quantifiable formats; and a computer workstation.

These instruments can fit in a sterile laminar flow or fume hood, or are enclosed, self-contained systems, for cell culture growth and transformation in multi-well plates or tubes and for hazardous operations. The living cells will be grown under controlled growth conditions, with controls for temperature, humidity, and gas for time series of the live cell assays. Automated transformation of cells and automated colony pickers will facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

In a preferred embodiment, the devices of the invention include sensors for leak detection. These are generally of two types; either electronic measurements of resistance or the spiking of the assay with optical or detectable tags. This may be particularly important in some embodiments where biohazardous materials or caustic chemicals are being tested.

In a preferred embodiment, the devices of the invention comprise a device board that can be used to do a variety of analyses, including signal processing, digital lock-in, comprising logic circuits, etc., as outlined herein.

In a preferred embodiment, the systems of the invention comprise a processor (CPU). This can be physically contained within the apparatus itself, can be connected via a cable, or can be connected using wireless technology. There can be one or more per device.

In a preferred embodiment, the devices of the invention include a localization device, such as a Global Positioning System (GPS) as are known in the art. This may find particular use in agriculture and biowarfare uses, as well as remote diagnosis of problems.

In a preferred embodiment, the devices of the invention include components for the communication of data, assay results, patient information, etc. to an off-device location. Thus, for example, one or more modems (including both telephone and cable modems), internet cards, infrared ports, etc. may be included in the devices to allow the transmission of data and other relevant information (barcode information, assay conditions and protocols, operator identification, time stamps, etc.) to a remote location such as a general information repository, hospitals, doctor's offices, epidemiology centers, pharmacies, government centers, insurance providers, etc.

In a preferred embodiment, the devices of the invention include components for wireless communication systems, to allow this transmission of data in the absence of physical electronic or communications connections. In addition, wireless receivers can be included.

Accordingly, the present invention provides methods and compositions for the multiplex analysis of samples and target analytes. Samples (either raw samples or treated samples (e.g. amplified, purified, etc.)) are loaded into the cartridges of the invention, optional caps are put on, and the cartridges loaded into a station of the device. Additional reagents are added as necessary, and assay complexes formed.

Once the assay complexes of the invention are made, that minimally comprise a target sequence and a label probe, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the other system components, the composition and integrity of the monolayer, and what type of reference electrode is used. As described herein, ferrocene is a preferred ETM.

In some embodiments, co-reductants or co-oxidants are used as is generally described in WO00/16089, hereby expressly incorporated by reference.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence.

These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7-biphenyl_2-phenanthroline)_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include $Ru(4,7-biphenyl_2-phenanthroline)_3^{2+}$, $Ru(4,4'-diphenyl-2,2'-bipyridine)_3^{2+}$ and platinum complexes (see Cummings et al., J. Am. Chem. Soc. 118:1949-1960 (1996), incorporated by reference). Alternatively, a reduction in fluorescence associated with hybridization can be measured using these systems.

In a further embodiment, electrochemiluminescence is used as the basis of the electron transfer detection. With some ETMs such as $Ru^{2+}(bpy)_3$, direct luminescence accompanies excited state decay. Changes in this property are associated with nucleic acid hybridization and can be monitored with a simple photomultiplier tube arrangement (see Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capicitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors.

There are a variety of techniques that can be used to increase the signal, decrease the noise, or make the signal more obvious or detectable in a background of noise. That is, any technique that can serve to better identify a signal in the background noise may find use in the present invention. These techniques are generally classified in three ways: (1) variations in the type or methods of applying the initiation signals (i.e. varying the "input" to maximize or identify the sample signal); (2) data processing, i.e. techniques used on the "output" signals to maximize or identify the sample signal; and (3) variations in the assay itself, i.e. to the electrode surface or to the components of the system, that allow for better identification of the sample signal. Thus, for example, suitable "input" AC methods include, but are not limited to, using multiple frequencies; increasing the AC amplitude; the use of square wave ACV; the use of special or complicated waveforms; etc. Similarly, suitable "output" AC techniques include, but are not limited to, monitoring higher harmonic frequencies; phase analysis or filters; background subtraction techniques (including but not limited to impedance analysis and the use of signal recognition or peak recognition techniques); digital filtering techniques; bandwidth narrowing techniques (including lock-in detection schemes particularly digital lock in), Fast Fourier Transform (FFT) methods; correlation and/or convolution techniques; signal averaging; spectral analysis; etc. Additionally, varying components of the assay can be done to result in the sample signal and the noise signal being altered in a non-parallel fashion; that is, the two signals respond non-linearly with respect to each other. These techniques are described in WO00/16089 and O'Connor et al., J. Electroanal. Chem. 466(2):197-202 (1999), hereby expressly incorporated by reference.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the working and counter electrodes is swept through the electrochemical potential of the ETM (for example, when ferrocene is used, the sweep is generally from 0 to 500 mV) (or alternatively, the working electrode is grounded and the counter electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

Thus, the devices of the invention preferably provide voltage sources capable of delivering both AC and DC currents.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In a preferred embodiment, multiple frequencies with a small AC voltage is applied and the fundamental of each is evaluated. Alternatively, a preferred embodiment utilizes several frequences with a large ACV, and the harmonics of each are evaluated. Similarly, preferred embodiments utilize several frequencies with a large ACV where the effect of the different frequencies on the system can result in an output that is different from the sum of the outputs at individual frequencies.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input frequency, and any changes in frequency response is an indication that the ETM is present, and thus that the target sequence is present.

In a preferred embodiment, the input signals and data processing steps are done to increase the non-linearity of the system. That is, for example, the ferrocene response reacts non-linearly, producing a harmonic response in the signal above that in the background; this harmonic signal from AC voltammetry is most likely the result of a harmonic distortion due to the nonlinear response of the electrochemical cell; see Yap, J. of Electroanalytical Chem. 454:33 (1998); hereby incorporated by reference. Thus, any techniques that increase this non-linearity are desirable. In a preferred embodiment, techniques are used to increase the higher harmonic signals; thus, frequency and phase-sensitive lock-in detection is performed at both the fundamental frequency of the applied waveform and also at multiples of the fundamental frequency (i.e. the higher harmonics). Since the background capacitance responds relatively linearly to AC signals (a sine wave input AC voltage results in a relatively nondistorted sine wave output), very little upper harmonic current is produced in the background. This gives a dramatic increase in the signal to noise ratio. Thus, detection at the higher harmonic frequencies, particularly the third, fourth and fifth harmonics (although the harmonics from second to tenth or greater can also be used) is shown to result in dramatic suppression of the background currents associated with non-Faradaic processes (like double layer charging) that can overwhelm the signal from the target molecules. In this way, the evaluation of the system at higher harmonic frequencies and phases can lead to significant improvements in the detection limits and clarity of signal. However, in some embodiments, the analysis of higher harmonics is not desired.

Thus, in a preferred embodiment, one method of increasing the non-linear harmonic response is to increase or vary the amplitude of the AC perturbation, although this may also be used in monitoring the fundamental frequency as well. Without being bound by theory, it appears that increasing the amplitude increases the driving force nonlinearly. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, harmonic square wave ACV is used; see Baranski et al., J. Electroanal. Chem. 373:157 (1994), incorporated herein by reference, although in some embodiments this is not preferred. This gives several potential advantages. For example, square waves are easier to create digitally and the pulse shape of the square wave can allow for better discrimination against charging capacitance. In sinusoidal harmonic AC voltammetry, harmonic signals provide better signal to background since faradaic response can be more nonlinear than charging capacitance. The same concept applies to SW harmonic ACV. The key difference between the two techniques is the frequency spectrum of the AC waveform. A singular frequency sinusoidal waveform contains just the fundamental frequency where as a singular square Wave contains the fundamental frequency as well as all odd harmonics. The techniques looks at the even harmonics where the ratio of faradaic current to capacitance current is enhanced. All the odd harmonics have single ACV peaks while all the even harmonics have double ACV peaks. This is opposite to the case of sinusoidal harmonic ACV of a system that has a non-reversible redox couple.

In a preferred embodiment, multiple frequency ACV is used. The idea is to create a waveform consisting of multiple frequencies with the same amplitude or different amplitudes to excite an electrochemical cell in an ACV fashion. The method benefits from fast Fourier transform or joint time-frequency transform to analyze the cell response. A JTFT spectrogram of a multiple frequencies ACV provides information on the driven (or fundamental) frequencies as well as their harmonic components. Some possible data analyses are: 1) comparison of response of fundamental frequencies, 2) comparison of all harmonic frequencies, 3) comparison of the response of one particular harmonic frequency of all excited frequencies, and 4) all analyses possible by standard single frequency ACV.

Accordingly, in a preferred embodiment, a fast Fourier transform is done, as is generally outlined in the examples. Fourier transform analysis is a preferred method for improving signal to noise and isolating desired signals when sinusoidal electrochemistry is done. Typical AC techniques rely on measurements of the primary frequency only. With sinusoidal voltammetry (and other inputs) observation at higher harmonics allows discrimination of signals primarily based on kinetics. For example, both fast and slow redox events would give similar peaks (provided the AC frequency was not too high) at the primary frequency. However, at higher harmonics, some redox molecules would generate signals while others would not. Using FFT analysis, all the various frequency components of a response to a sinusoidal input can be observed at once.

Similarly, in a preferred embodiment, a joint time-frequency transform (JTFT) is done.

In a preferred embodiment, digital lock-in techniques are used. In the past, digitized raw data from the electrochemical cell have been analyzed by either fast Fourier transform or some complex form of joint time-frequency transform analysis. The major draw back of these methods is the enormous computational time associated with frequency transformation techniques. Digital lock-in, on the other hand, is simple and fast. In principle, digital lock-in is identical to analog lock-in. In the former case, the bandwidth narrowing process is done mathematically by multiplying the cell response by a sinusoidal with the same frequency as the input voltage, but with 90° phase shift. The technique has the same limitation as its analog counterpart since only one frequency can be analyzed at a time. However, unlike analog lock-in, other frequencies can also be analyzed sequentially (or in parallel with a more powerful processor) since the raw data is archived. For an input voltage of $$V_{in} = E_{dc} + rt + E_{ac} \sin(\omega t) \quad (1)$$

the cell's response is essentially $$I(t) = \sum_n I_n(v)\sin(n\omega t - \phi_n) = \sum_n I'_n(v)\sin(n\omega t) - I''_n(v)\cos(n\omega t) \quad (2)$$

To find the voltage dependent coefficients $I_n$ for the frequency ($n_0$ w) we multiply the response by 2 $\sin(wn_0 t)$ and $-2\cos(wn_0 t)$ and apply a low pass filter to get the real and imaginary components. The low pass filtering used in this example is a simple moving average. Mathematically, the process is expressed as $$\frac{1}{t1-t0}\int_0^{t1}\left(\sum_n I'_n(v)\sin(n\omega t) - I''_n(v)\cos(n\omega t)\right)2\sin(\omega n_0 t)dt = \quad (3)$$

$$\frac{I'_n(v)}{t1-t0}\left(t - \frac{\sin(2n_0\omega t)}{2}\right)\bigg|_{t1,t0} = I'_n(v), \text{ for } t_1-t_0 \gg T$$

In a preferred embodiment, background subtraction of the current vector and phase optimization is done.

In a preferred embodiment, correlation and/or convolution techniques are used. In this embodiment, many scans of the same electrode. Rather than looking for a peak in a single scan, many scans are viewed and a common correlation between the scans. For instance, it is possible that a bump in the noise appears near 180 mV for a negative, even if no ferrocene is present. However, it is unlikely that the same bump will appear in the same place if the frequencies are scanned. Thus, preferred embodiments take scans at many frequencies and only count a positive if a peak occurs in all of them. This is a very simple correlation; more complex correlations may be done as well.

In a preferred embodiment, signal recovery is done using signal recognition and background subtraction. In this embodiment, the idea is to fit the cell response to two summed functions, one that describes the signal and the other that models the background capacitive current. Once the functions 1, are constructed, the signal is easily recovered from the response by subtracting the fitted background capacitive current. This signal recognition scheme is applicable to any system where the signal has a behavior and shape that is relatively well known. The following example illustrates how such a scheme can be applied to the systems of the invention.

The response from an electrochemical cell can be processed with a lock-in amplifier or equivalent bandwidth-narrowing technique. This is one of many methods of increasing signal to background using some form of bandwidth-narrowing technique.

In a preferred embodiment, spectral analysis of the signal is done. In this embodiment, filtering techniques in the frequency domain make use of means, variances, densities, autocorrelation functions, and power spectral densities of the signal and apply it to the present systems to enhance the signal to noise ration (see Schwartz et al., Signal Processing: Discrete Spectral Analysis, Detection, and Estimation, N.Y. McGraw Hill, 1975, hereby incorporated by reference).

In a preferred embodiment, digital filtering techniques are used. These include, but are not limited to, match filter, Weiner filtering, Kalman, Finite Impulse Response, infinite impulse response, narrow band filtering, etc.

In a preferred embodiment, a match filter is used; see Ziemer et al., "Principles of Communication Systems, Modulation and Noise", 4th Ed. John Wiley & Sons Inc., New York, 465-471, 1988; and Helstrom, C. W., "Statistical Theory of Signal Detection", Pergamon Press, Oxford, 112-115, 1968, both of which are incorporated by reference. In its simplest form, a match filter is a signal processing technique that "weights" the measured response (signal plus noise) samples by some corresponding known signal amplitude and convolutes the two signals to enhance signal to noise.

In a preferred embodiment, a Weiner filter is used (see Press, supra; and Elliot et al., Fast Transforms: Algorithm, Analysis, Applications N.Y. Academic Press (1982), both of which are incorporated by reference). Weiner filtering involves finding an optimal filter that removes noise or background from the "corrupted" signal. This signal processing method works in conjunction with Fourier transform techniques. The idea is as follows. Due to poor signal to noise or a large background, the output from the instrument is a "corrupted" signal $$c(t) = s(t) + n(t)$$

where s(t) is the signal and n(t) is the noise. Note that s(t) is not the signal we're after, it is composed of the true uncorrupted signal u(t) convolved with some known response function r(t) (In the case of the CMS system with a redox couple, u(t) is the Nernstian). In other words, $$s(t) = \int_{-\infty}^{\infty} r(t-\tau)u(\tau)d\tau.$$

In frequency space, the relation is $$S(\omega) = R(\omega)U(\omega),$$

where S, R, and U are the Fourier transform of s, r, and u, respectively. The uncorrupted signal can be recovered by finding the optimal filter $\phi(t)$ or its Fourier counterpart $\phi(\omega)$ which when applied to the measured signal c(t) or C($\omega$), and then deconvolved by r(t) or R($\omega$), produces a signal that approximate the uncorrupted signal u(t) or U($\omega$) with $$U(\omega) = \frac{C(\omega)\Phi(\omega)}{R(\omega)}.$$

In general the optimal filter is defined as $$\Phi(\omega) = \frac{|S(\omega)|^2}{|S(\omega)|^2 + |N(\omega)|^2}.$$

In a preferred embodiment, a kalman filter is used, which is a recursive-estimation filtering technique that tracks the current value of a changing signal in the presence of noise. See Kalman et al., A New Approach to Linear Filtering and Prediction Problems, Trans. ASME J. Basic Engineering, Seires D, 82, Mar. 35, 1960; Elliot Ed. Handbook of Digital Signal Processing: Engineering Applications", Academic Press, San Diego, p 908, 1987; Chui et al., Kalman Filtering: with Real Time Applications", Springer-Verlag, New York, 1987; all of which are expressly incorporated by reference.

In a preferred embodiment, the non-linear harmonic response is increased by inducing an asymmetrical response. In a preferred embodiment, this is done by using a system that has a non-reversible redox couple. For example, ferrocene is a redox couple that is very reversible. Thus, the ferrocenes subtended by the ac voltage at a given point, get oxidized on the upswing of the ac voltage and reduced on the down swing. However, If a semi-reversible or non-reversible redox couple is used, for example, the molecule will get oxidized on the up swing and not reduced (or a portion) on the downswing; or vice versa. This will produce even greater non-linearities at certain frequencies.

Three examples of ways to perform this are: use an ETM molecule that gets degraded in the oxidized form, like luminol, use co-reduction or redox mediation, and use enzyme coupled mediation, as generally described in WO00/16089.

In a preferred embodiment, electron transfer is initiated using alternating current (AC) methods. In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the ETM. In a preferred embodiment, the frequency response is determined at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femptoamp to about 1 milliamp, with currents from about 50 femptoamps to about 100 micrbamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is significantly different depending on whether the label probes containing the ETMs are specifically or non-specifically bound to the electrode.

Accordingly, the present invention further provides electronic devices or apparatus for the detection of analytes using the compositions of the invention. The apparatus includes a test chamber for receiving a sample solution which has at least a first measuring or sample electrode, and a second measuring or counter electrode. Three electrode systems are also useful. The first and second measuring electrodes are in contact with a test sample receiving region, such that in the presence of a liquid test sample, the two electrophoresis electrodes may be in electrical contact.

In a preferred embodiment, the apparatus also includes detection electrodes comprising a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Once made, the multiplexing devices and cartridges of the invention find use in a wide variety of applications. In particular, the compositions of the invention find use in hybridization assays. As will be appreciated by those in the art, electrodes can be made that have a single species of nucleic acid, i.e. a single nucleic acid sequence, or multiple nucleic acid species.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261(1993). Multiplex PCR amplification of SNP loci with subsequent hybridization to oligonucleotide arrays has been shown to be an accurate and reliable method of simultaneously genotyping at least hundreds of SNPs The present invention is directed to methods of determining the sequence of a target nucleic acid at a particular position, using electrochemical detection on an electrode. The invention preferably includes the detection (and optionally quantification) of differences or variations of sequences (e.g. SNPs) using electrode arrays for detection of the variation.

As is known in the art, there are a number of techniques that can be used to detect or determine the identity of a base at a particular location in a target nucleic acid, including, but not limited to, the use of temperature, competitive hybridization of perfect and imperfect probes to the target sequence, sequencing by synthesis, for example using single base extension techniques (sometimes referred to as "minisequencing"), the oligonucleotide ligase amplification (OLA) reaction, rolling circle amplification (RCA), allelic PCR, competitive hybridization and Invader™ technologies. In addition, the present invention is directed to a novel invention that capitalizes on novel properties of surface-bound arrays, and uses "competimers" to reduce non-specific binding.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected, for example using ribosomal RNA (rRNA) as the target sequences.

In a preferred embodiment, the nucleic acids of the invention find use as probes for toxic bacteria in the screening of water and food samples. For example, samples may be treated to lyse the bacteria to release its nucleic acid (particularly rRNA), and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 7 of PCT US97/20014. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

All references cited herein are incorporated by reference in their entirety.

EXAMPLES

Example 1

Signal Analysis

The present invention utilizes electrochemical techniques to detect various biological and chemical targets. Generally these techniques yield signals with an informative or a characteristic shape, size, and location. By creating a computer program that recognizes a signal's characteristic features, we can distinguish signals from background phenomena and extract any relevant information necessary for accurate detection.

Fitting to a Model

It's generally possible to design a family of equations and a set of boundary conditions that describe the signals that can arise from a given measurement technique. This mathematical description is called a "model." Sometimes the model is based on underlying scientific theory, but in many cases it may simply be an approximation that matches the observed signal behavior. In most cases the model is "nonlinear," comprising equations that are more complicated than basic polynomials.

There are several ways to fit data to a non-linear model, but they commonly involve the following steps: 1) the rapid detection of any common behaviors not described by the model, 2) an initial guess, 3) iterative improvement and evaluation, repeated as necessary, 4) the detection and correction of common erroneous fits, if any, and 5) a final evaluation to judge the quality of the fit. Once a fit is chosen, the values of important parameters can be extracted for use in further data analysis.

Vector Notation for Describing AC Signals

As an example illustrating the signal recognition methods described in this report, I will use what is currently our most common electrochemical technique: Alternating Current (AC) Voltammetry monitored at the fourth harmonic. This technique yields an AC signal (a sine wave) that varies its amplitude (height, R) and phase (position, q) as a function of the input DC voltage. As long as we monitor at a known frequency, it only takes two values to define such a wave. FIG. 16 depicts a sine wave and its corresponding vector notation.

The two values can be R and $\theta$, but as shown above they can also be an (X,Y) pair separated by one quarter of an oscillation, i.e. by 90°. One way to simplify the visualization of such a system is by using what is called vector notation, demonstrated in four configurations in FIG. 17. It's important to observe that the values (R,$\theta$) and (X,Y) are different but interchangeable ways of describing the same vector. The vector itself is what represents the sine wave and, therefore, the data. Furthermore, the difference between the primed and unprimed values (those on the right side of the diagram versus those on the left) is only a rotated frame of reference (as indicated, for example, by the relative positions of the dotted lines in the polar coordinate diagrams). This rotation also does not alter the data, but can be useful as described in later sections.

One important attribute of vector notation is that the vectors add exactly like the corresponding waves. For example, if two vectors point in roughly opposite directions, when they add they tend to cancel one another, leaving only a small residual vector. This exactly models how it is possible to add two waves together in such a way as to have "destructive interference," where the resulting amplitude is less than each of the inputs. As long as all waves have the same frequency, vectors will model their interference with one another.

In AC Voltammetry, we monitor the oscillations at a given frequency as a function of an input voltage. Since vector notation exactly models sinusoidal behavior at any single, known frequency, in my description of our fitting I will only describe the data as a vector.

Choosing to Fit in X and Y

During any experiment acquiring vectoral data, it is common for scientists to only actively monitor the value of R (even if both R and $\theta$ are recorded). This is because, depending on the system and experimental setup, the frame of reference may change from one instrument to another or from one day to the next. R, however, does not change with the frame of reference. (Remember that, in polar coordinates, a frame of reference rotation only changes $\theta$.)

However, in order for signal recognition to work we need a model, a mathematical description of the shapes we expect to observe. The simpler and less varied the shape, the easier the description and recognition. FIGS. 18 and 19 are examples of R and $\theta$ traces for fourth harmonic AC voltammetry (ACV-4).

The four-lobed shape in R-space is characteristic of medium to large signals, but as the signal shrinks relative to the size of the background, the R-space signal distorts. Furthermore, q traces of scans with larger signals are quite different from those with smaller ones. FIGS. 20 and 21 depict examples of a smaller signal.

This complex (R,$\theta$) behavior is a characteristic of vectoral traces that comprise both signal and background. If we have signal $\vec{S}$ (described by $R_S$ and $\theta_S$) with a background $\vec{B}$ (described by $R_B$ and $\theta_B$), then the data is $\vec{D} = \vec{S} + \vec{B}$. $\vec{D}$ is described by is described by $R_D$ and $\theta_D$, which have dependence on the signal and background values:

$$R_D = \sqrt{(R_S\sin\theta_S + R_B\sin\theta_B)^2 + (R_S\cos\theta_S + R_B\cos\theta_B)^2}$$

$$\theta_D = \arctan\left(\frac{R_S\sin\theta_S + R_B\sin\theta_B}{R_S\cos\theta_S + R_B\cos\theta_B}\right)$$

The complexity of R and q traces comes from the fact that $R_D$ depends on all four parameters ($R_S$, $\theta_S$, $R_B$, and $\theta_B$), as does $\theta_D$. However, if we use Cartesian coordinates to describe the data instead of polar ones, then $\vec{D}$ is described by $X_D$ and $Y_D$, which are:

$$X_D = X_S + X_B$$

and $$Y_D = Y_S + Y_B$$

Using Cartesian coordinates simplifies the dependence of $\vec{D}$'s parameters on those of $\vec{S}$ and $\vec{B}$. This simplicity is exhibited when graphing the same examples shown previously, but now as (X,Y), as depicted in FIGS. 22 and 23 (medium sized signal), and FIGS. 24 and 25 (smaller signal).

The smaller signal is now qualitatively similar to the medium signal, and is therefore more likely to be described by the same mathematical model. Because of this, we chose to fit in X and Y (for simplicity in conceiving a model and in computation during fitting, we chose to fit independently in X and Y instead of fitting both dimensions simultaneously.

The Model Assumed for ACV-4

We have compared the characteristic shape exhibited by ACV-4 signals to several different mathematical expressions. The four-lobed profile immediately suggested we use an equation related to the third derivative of a peak shape, and after making many comparisons, we concluded that the third derivative of a Gaussian (G''') was a very good approximation to an ACV-4 signal. The order of polynomial (and therefore the number of parameters needed to describe its shape) will depend on the length of the scan. Longer scans will require higher order polynomials to account for the same scan features. As for the background, a polynomial (P) should be sufficient to account for the majority of the different shapes that we observe. This translates to the following equations, where $\vec{I}(V)$ is the data, $\vec{I}_S(V)$ is the signal, and $\vec{I}_B(V)$ is the background:

$$\vec{I}(V) = \vec{I}_S(V) + \vec{I}_B(V) = \lfloor\vec{G_X'''}(V) + \vec{G_Y'''}(V)\rfloor + \lfloor\vec{P_X}(V) + \vec{P_Y}(V)\rfloor$$

$$= \lfloor\vec{G_X'''}(V) + \vec{P_X}(V)\rfloor + \lfloor\vec{G_Y'''}(V) + \vec{P_Y}(V)\rfloor$$

This leads to the final equations we used for our ACV-4 model:

$$X(V) = G_X'''(V) + P_X(V)$$

and $$Y(V) = G_Y'''(V) + P_Y(V)$$

We have also created fitting procedures for systems with more than one label (differentiated by their position in voltage space). They use a model analogous to that described above, but with the underlying assumption of more than one signal that is:

$$\vec{I}(V) = \vec{I_B}(V) + \sum_n \vec{I_{S,n}}(V)$$

As for boundary conditions, note that the Gaussian derivatives $G_X'''$ and $G_Y'''$ each have three parameters each: one for height, one for width, and one for location (in voltage). The height has no restrictions, corresponding only to the number of electrochemical labels that are signaling. However, in order to represent a true electrochemical signal, a fit's width must fall within a reasonable range. Furthermore, signals in the independent X and Y fits must be close to one another (in voltage space) to assure that they both correspond to the same electrochemical label. Later I will discuss how these boundary conditions may be "enforced" to assure a meaningful fit.

Optimal Phase

As mentioned previously, the choice of reference frame is arbitrary. As far as the data is concerned, one (X,Y) pair is just as good as another, rotated (X',Y') pair. However, since the model is often an approximation to reality instead of an exact theoretical description, the model may impose a preferred frame of reference. This is true of the ACV-4 system described above.

As an example, lets consider one ACV-4 trace that has a large signal relative to the background. If, in a two-dimensional graph, we plot the tip of the data vector as a function of voltage, it results in FIG. 26. Note that these correspond to a system with only one electrochemical label.

If we choose a frame of reference such that the X and Y axes straddle the signal, as shown above, then the signal contributes strongly to both X and Y as shown in FIGS. 27 and 28.

However, if we choose an axis pair that is roughly parallel and perpendicular to the signal (rotated 45° with respect to the axes drawn in the graph at the top of the page), very little of the signal contributes to the perpendicular vector as shown in FIGS. 29 and 30.

Furthermore, we can see that the four-lobed shape we chose for the ACV-4 model does not describe the six lobes of the perpendicular trace. If we were to try to use the model to fit the data using the parallel and perpendicular (X,Y) pair, we would only be able to extract the signal out of the parallel component, thus losing one of the dimensions of our data.

Instruments generally assign the X and Y axes based on the phase of the AC input driving force. Because this choice does not take into account the electrochemical system, it's possible that it may lead to the parallel/perpendicular trouble described above. Therefore, for signal recognition based on the above model, it's best to choose a new pair of axes assured to straddle any existing electrochemical signal.

In order to choose such axes, we need a way to measure the signal's direction. We could fit a line to the signal in polar coordinates, but we can't use basic linear fitting since the X and Y signals are independent of one another.[1] A non-linear fit would work,[2] but would be an iterative procedure and so would take more processing time than we'd care to use. Instead, we'd rather use a faster way involving simpler mathematical operations. One such way is using a vectoral sum. Consider the grouping of three points as shown in FIG. 31.

[1]Imagine a signal aligned along the Y axis. If we attempt a linear, least squares fit (the most common type of fitting), the resulting line is not along the signal, but rather along the X axis, with equal numbers of points above and below the fitting line. This is because the data, when considered only as the values in the Y direction, has no X dependence.
[2]Javier Gonzalez implemented this: Amor/c/my documents/labview documents/phase optimize/linearfit.vi.

If we consider these points as vectors, we can add them by summing their coordinates. The vectoral sum will have coordinates $$X = \sum_i x_i$$

and $$Y = \sum_i y_i$$

This summation of the vectors provides a reasonable angle for the best line through the data that passes through (0,0).

$$\theta_{opt} = \arctan\left(\frac{Y}{X}\right) = \arctan\left(\frac{\sum_i y_i}{\sum_i x_i}\right)$$

We call this angle the "optimal phase." For our example, the summation is drawn in FIG. 32. FIG. 33 shows that we see how the three sample data points cluster around the line. For them, the optimal phase is 64°.

An advantage to this method is that the results are weighted by the length of the vectors of the original data points. That is, if a data point has a small amplitude (as it will if it represents a segment of a scan where no signal exists), it has a smaller impact on the value of the optimal phase. For example, if we add a small data point to the sample grouping, the results are shown in FIGS. 34 and 35.

The new point changes the optimal phase by less than three degrees. If desired, it is possible to give the small values even less weights. A more generic expression for the optimal phase has its summations weighted by the lengths ($r_i$) of the individual data points' vectors. Increasing the value of n places less and less emphasis on the small data points. However, in all of our current fitting programs, we use the equation as written above, equivalent to the case where n remains zero.

$$\theta_{opt} = \arctan\left(\frac{\sum_i y_i r_i^n}{\sum_i x_i r_i^n}\right) = \arctan\left(\frac{\sum_i y_i (x_i^2 + y_i^2)^{\frac{n}{2}}}{\sum_i x_i y_i (x_i^2 + y_i^2)^{\frac{n}{2}}}\right)$$

We can use this method to calculate the optimal phase for fitting a signal, but there are complications that must be considered. For many techniques (including ACV-4), the electrochemical signal is shaped such that portions of it may cancel each other out when completing the calculation described above. To avoid this, we first rotate one half of the data 180'. Taking the data shown in FIG. 26, we calculate the optimal phase using the data as shown in FIG. 36. The resulting line is overlaid on the original data, at FIG. 37.

The angle of the line drawn in above (101°) is what was used to choose the X and Y axes (at ±45°) for this file. Unfortunately, however, there can be a further complication. If the signal is oriented differently relative to the dividing line between rotated and unrotated segments, the stated manipulation may not yield the proper angle. For example, if I take the above signal and rotate it 101 degrees clockwise, its optimal phase should be 0. However, the calculated value actually ends up as −48' as shown in FIG. 38.

To prevent this, we need to choose a rotation boundary that is more perpendicular to the signal than it is parallel. We can do so by first determining whether the signal lies mostly along 0 degrees or mostly along 90. If we take the vectoral sum of the absolute value of the coordinates of a signal that's closer to 90, the resulting angle $$\arctan\left(\frac{\sum_i |y_i|}{\sum_i |x_i|}\right)$$

will be greater than 45'. On the other hand, for the above case we find an angle of 10 degrees (see FIG. 39), less than 45, and conclude that the signal is more along 0 degrees. Therefore, we rotate the half of the signal from the far side of the 90 degree axis (see FIG. 40).

Calculating the vectoral sum now yields a reasonable value for the optimal phase: 1', similar to the expected 0°.

The final complication is the fact that we don't want to find the optimal phase for an entire scan, but rather for any electrochemical signal present in a scan. We want to ignore any background. Unfortunately, if the signal is small, the optimal phase calculations outlined above would be dominated by the phase of the background. To avoid this, we perform an approximate background subtraction before calculating the vectoral sum.

For example, if we examine the scan called "Smaller Signal" on page six, we see a large contribution by the background. If we examine the scan in two dimensions, we can see that the phase of the entire scan is mostly along 120' (FIG. 41).

However, if we perform the rapid calculations necessary to fit polynomials to the entire scan (one each along the 0 and 90' axes), we can approximate the background as shown in FIGS. 42 and 43. In this instance, we are using the symmetry of the ACV-4 to our advantage. If a signal has equal contributions above and below the background (as is true of any even harmonic ACV), then a polynomial fit will tend to follow the centerline of that signal. This makes the polynomial fit to the scan an excellent estimation of the background. To calculate the polynomial, we currently use a "general polynomial singular value decomposition fit".

This approximation to the background can then be subtracted, converting the scan into something that is much more purely signal, as shown in FIG. 44 and 45. FIG. 46 depicts this as a two dimensional plot.

From the above, we can see that now, using the techniques outlined earlier in this section, we could calculate an optimal phase of approximately 70°.

In summary, the basic procedure for choosing the X and Y axes is as follows:

1. Fit an approximate background along each of the 0 and 90° directions. Subtract them from the scan, leaving a residual trace dominated by signal.

2. Take the absolute value of all coordinates (along 0 and 90°). Calculate a vectoral sum. Determine if its angle ($\theta_{abs}$) is closer to 0° or 90°.

3. If $\theta_{abs}$ is closer to 0°, select all data points to the left of the 90° axis. If closer to 90°, take all data points below the 0° axis. Rotate these 180°.

4. Calculate a vectoral sum. Its angle is the "optimal phase" ($\theta_{opt}$).

5. Choose the X and Y axes at ±45° from $\theta_{opt}$.

Checking for Behaviors Not Modeled

To reduce total processing time, it's best to notice early if a scan has any gross deviations from the model that would make fitting it meaningless. One such feature we have encountered in AC voltammetry (fourth harmonic) has been the sharp peak caused by the stripping of a metallic contaminant. FIG. 47 shows an example of one displayed in R-space.

In X and Y (at ±45° from the optimal phase), the sharp spike feature remains clear, as shown in FIGS. 48 and 49.

The symmetry of this feature distinguishes it from our normal signal: although ACV-4 signals have equal portions above and below the background, this spike does not.

One quick but rough method of monitoring this symmetry is to separate out an approximate background (as we had done to determine the optimal phase) and then compare the distribution of points above the baseline with the distribution below. For example, if we subtract a polynomial from the Y trace above, we get the results shown in FIGS. 50 and 51.

If we now examine the distribution of data above and below the approximated background, we find that the presence of the spike causes a larger range of values to exist below the background line than above it, as shown in FIG. 52.

In this example, the standard deviation of the data below the line is about 2½ times larger than the standard deviation above. We can take this as an indication of symmetry different from that expected of an ACV-4 signal, since ACV-4 signals are distributed evenly about the assumed background and therefore have ratios closer to 1. By setting a range of acceptable values,[3] this rough method allows for the rapid detection and rejection of scans with large spikes.

[3] We currently consider a ratio less than 2.25 and greater than ½.25 to be acceptable for further fitting. However, it's important to be aware that this value can depend on unusual parameters, such as scan length.

The Initial Guess

Iterative fitting procedures all require a starting point, an initial guess for the values of the model's equations that would match the data. Iterations (discussed in the following section) then improve upon these guesses in gradual steps. For systems with simple models, there is often only a need for a single, predetermined initial guess. In that case, the guess is an adequate starting point for all possible data. However, for models that comprise complex shapes (such as the model we use for ACV-4), an accurate initial guess based on each individual scan can lead to more rapid fitting and can reduce or eliminate any tendency to create erroneous fits.

Again, we can use symmetry to our advantage. First, for a signal with symmetry such that it's distributed equally above and below the baseline, we can use a fast polynomial fit[4] to calculate an initial guess for the background. As was true in the optimal phase calculation outlined in a previous section, this polynomial will tend to fit to the centerline of any signal, thus making a good background estimation.

[4] The "general polynomial singular value decomposition fit" mentioned previously.

When we subtract out the estimation of the background, what remains ("the residual") should be mostly signal (if any). To estimate that signal, we can begin with the fact that a given measurement technique and chemical system generally yields signals with characteristic behaviors. For CMS sensors probed with ACV-4, all signals have similar widths. An initial guess based on the most common width is therefore appropriate.

To guess the remaining parameters of signal position and signal height, we can again use the known ACV-4 symmetry, this time combined with knowledge of the characteristic width. Since we know the average separation between the two larger center lobes, we can duplicate the signal and shift the two copies in opposite directions for half of that separation. If we then subtract one from the other, the center lobes interfere constructively. The absolute value of this resulting wave provides a good estimation of the height and position of the signal. This process is shown in FIGS. 53, 54 and 55 for a signal 11.9 tall at a position of 0.20 with a center lobe separation of 0.072.

The trace in the final graph of this example has its largest value, 23.25, at a position of 0.20. The position matches well with the true data value. (Both are 0.20.) The constructive interference height should be about twice the center-to-peak signal height, which means the interference plot gives an initial guess of ½×23.25=11.6. This is only 3% different from the input value. (This difference occurs because the shift used in the above process was 0.062, different from the actual 0.072 separation of the sample signal.)

One important advantage of the above method (rather than if we were to simply search for maxima and minima in the raw data) is that it amplifies only those features with the expected width and symmetry of the signal. Consider the same signal as above, but this time with an unusual peak off to one side that's slightly taller than the signal itself. (See below.) In a simple maxima/minima search, this would be likely to interfere with the initial guess. However, using the procedure outlined above, the initial guess will remain 11.6 tall at a position of 0.20, as shown in FIGS. 56 and 57.

We therefore have a method of calculating an initial guess for all parameters (the signal height, position, and width, plus the background) that involves only 1) calculating a polynomial using a rapid (linear) fitting method, 2) searching for the largest number in a set, and 3) simple arithmetic. As an example of the power of this technique, FIG. 58 is the overlay of a real data trace and the corresponding initial guess.

Optimization and Dynamic Range

Once an initial guess has been made, we can use any of a number of standard non-linear regression algorithms to optimize the fit. (We currently use a version based on the Levenberg-Marquardt 2 method.) While they differ in the details, the basic procedures are all the same. The initial guess is compared with the actual data, and the fit is altered based on this comparison in an attempt to minimize the "error". We iterate (repeat this process continuously) until the successive reductions in the error are smaller than the "precision" (a pre-set constant). In this case, the fit is said to have "converged". However, if the data doesn't match the entire shape described by the model, it's possible that the alterations to the fit won't reduce the error. (This will happen, for example, if the scan contains neither a signal nor noise that looks like a signal.) If the error doesn't become smaller than the precision within the "maximum number of iterations" (also a pre-set constant), the fit is said to have "diverged".

[5] This is discussed in Chapter 15 of *Numerical Recipes in C. The Art of Scientific Computing*, second edition, by W. H. Press, S. A. Teukolsky, W. T. Vetterling, and B. P. Flannery, Cambridge University Press, New York (1992). It was originally presented by D. W. Marquardt as the "maximum neighborhood" method in *Journal of the Society for Industrial and Applied Mathematics*, 11 (1963) 431-441.

The error and precision are often defined such that their values have units. For example, if the data is a current measured in picoamps, then the error and precision are in picoamps squared. This is most useful when all expected signals are of similar size, because it considers everything in absolute terms and will not attempt to optimize fits to small features. However, quantitative analytical techniques generally require a wide dynamic range. For example, one may need to examine signals that are two picoamps tall with the same ease as one examines two billion picoamp signals. To achieve such a dynamic range, we normalize data to the initial guess for the signal height. This allows the small signals to be fit just as well as the large, with only the shape and the background noise affecting the fit.

Boundary Conditions and Weighting

The question of boundary conditions arose earlier when discussing the choice of a model. For some systems, certain parameters may be reasonable only within a certain range. For example, for ACV-4 the width of the center two lobes of one of a CMS sensor signal always falls between 110 and 265 mV, and is most commonly between 150 and 200 mV. There are several ways to enforce these boundaries, two of which are discussed here.

If the initial guess for a scan is fairly accurate and the scan's signal is sizeable relative to the background, the fitting procedure will generally lock into the signal properly. There will be no need to enforce the boundary conditions. However, if there's no signal or the signal is obscured, it's possible for parameters to drift outside of their acceptable ranges. Now, for a well-behaved system, the only fits that exhibit this drift have no true signals. We can therefore discard fits with unacceptable values and consider the corresponding scans to be comprised only of background. (See "Quantitation of Negatives" below.) This is the procedure most widely used in our current software.

However, for systems that are less well-behaved, we may prefer to enforce the boundary conditions during the fitting itself rather than after the fact. We can do this by adding an additional term to the equation that describes the error for each constrained parameter, penalizing the fit as its parameters deviate from the desired range.[6] For example, if E is the error as defined by the non-linear regression technique, and if the parameter a is to be constrained to fall close to some expected value $\bar{a}$, then we can replace E with E', where k is some constant and n is an integer:

[6] Since Javier Gonzalez first conceived this idea, he has found similar methods described elsewhere. For example, Christopher Bishop describes a "regularization term" in *Neural Networks for Pattern Recognition*, Clarendon Press, Oxford (1995) 14-15.

$$E' = E + k(a-\bar{a})^{2n}$$

Remember that, during the iterative optimization, the goal is to minimize the error. If we use the equation above, then the farther a is from $\bar{a}$ the larger the error becomes and therefore the less favorable the fit. We can use the value of k to determine how important it is to constrain the parameter relative to the standard error E (and also relative to any other parameters' constraints). The value of n affects how unfavorable a certain range of values is. For example, in the graph in FIG. 59 we compare the shape when the added term has 2n=16 with when 2n=2.

In the case where 2n=16, a values within ±7 of the expected are all equally acceptable, with little added penalty. However, with 2n=2, there's an increasingly harsh penalty the further a moves from the expected value.

It's important to note that there's nothing critical about the form of the added term, so long as it's always positive.

For example, if we wanted a sharper constraint on a near its true value but not so much dependence when far off, we could use an expression like:

$$E' = E + k_1 \left[\arctan\left(\frac{a-\bar{a}}{c}\right)\right]^2$$

This equation leads to shapes like the ones depicted in FIG. 60.

Even more complicated shapes may be used. For example, for the case of our ACV-4 center lobe pairs (described previously), we may wish to use the shapes shown in FIG. 61.

This shape may be defined by:

$$\sum_{i=1}^{n} b_i \{1 + \tanh[c_i(a-s_i)]\} + \sum_{j=1}^{m} b_{j+n} \{1 - \tanh[c_{j+n}(a-s_{j+n})]\}$$

where there are n steps up, m steps down, the s's are the locations of the steps, the b's are their heights, and the c's control their steepness.

There is another way to use the error to control where various segments of a fit lock into a scan. The mathematical definition of the error E (often called the mean square error, or MSE) is below:

$$E = \frac{1}{N} \sum_{i=1}^{N} \frac{(F_i - D_i)^2}{\sigma_i^2}$$

In this equation, N is the number of data points, $F_i$, is the value of the fit for data point number i, $D_i$ is the corresponding data value, and $s_i$ is the standard deviation in this data value. This standard deviation is a measure of the uncertainty in $D_i$, and is generally known only if several different measurements were averaged to create $D_i$. (For data that has not been averaged, or whose averaging information has been lost, a value of $s_i=1$ is assumed, saying that all values are known with equal certainty.) By dividing by $s_i^2$, we're saying that a larger fitting error is acceptable for a given point if that data value was uncertain in the first place.

Irrespective of any uncertainty in data values, we can use the same kind of manipulation to force the fit to match the data more closely in certain data ranges than in others by introducing a weighting $w_i$ for each point. Data points with larger $w_i$'s (a heavier weighting) will be fit more closely than those with smaller $w_i$'s:

$$E_{weighted} = \frac{1}{N} \sum_{i=1}^{N} w_i^2 \frac{(F_i - D_i)^2}{\sigma_i^2}$$

(Note that this is exactly the same as introducing an alternate standard deviation equal to $\sigma_i/w_i$.) Now, this does not directly force the signal portion of the fit to exist in a region with large weighting. It only forces the fit as a whole to be tighter in this region relative to the other segments of the scan. However, the equations that describe signal are more localized than those that describe background, and they generally can exhibit much more curvature. Because of this, putting larger weightings $w_i$ around the expected signal position tends to force the signal to lock in near that value.

Since the initial guess is such an important factor when calculating a good fit, we need to use the weighting in that step as well. To accomplish this, we can multiply the |Shift and Subtract| value described in the "Initial Guess" section by some function, either based on the weightings $w_i$ or on the term added to create E', depending on the method.

Detecting and Correcting Flawed Fits

After completing the optimization and converging to a fit, it's still possible for that fit to have locked in improperly. For example, there can be edge effects. That is, since the computer has no data outside the scan range, it is completely free to assume any shape for the data outside that range. Because of this, the fitting procedure may conclude that an unusual background oscillation at the scan's edge is actually a signal. This kind of fit needs to be discarded, or perhaps avoided by using the weightings described above.

Other possible errors may be corrected. For example, in ACV-4 we fit in X and Y independently. Because of this, for small signals or for scans with wavy backgrounds, it's possible for the program to lock into incorrect lobes of the signal in either X or Y. That is, the fit may name a satellite and a central peak as the two central peaks. This will manifest itself as a fit to signal positions that are substantially different in X and Y. In these cases, we can take the scan (X or Y) that locked in too far from the expected position and refit. We base a new initial guess on the incorrect fit (keeping the background and the signal width, but correcting the signal position) and restart the iterative optimization. If this does not remedy the problem (or if the original difference in position is very large), then generally it means that we've locked into noise rather than a signal, so we discard this fit.

Judgment of Fit Suitability

Once a fit has converged and those fits with common flaws have been discarded or corrected, we need to judge if the fit has too much error. That is, we need to make sure that we've locked into a real signal. For example, examine the graph shown in FIG. 62.

Although the fit may closely follow the average path of the data, in the above case the fit isn't reliable because the difference between the fit and the data is too large. There is too much noise in the scan. We can judge this quantitatively by setting a threshold value for an acceptable error E.[7] In the case of ACV-4, since we fit in X and Y independently, we set a threshold value for maximum noise allowable in R-space:

[7] Again, this is actually the weighted mean square error, wMSE.

$$E_R = \sqrt{E_X^2 + E_Y^2}$$

$E_R$ must be less than some empirically-determined value in order for the fit to be considered as having locked into a true signal.

Quantitation of Negatives

Once all of the above procedures have been completed, many scans have had fits diverge or be discarded. These are classified as having no observable signal, and so are refit using only background as the model. For example, FIG. 63 is the R composite, $\sqrt{X^2+Y^2}$. In FIG. 64 is the R composite with the background polynomials subtracted, $$\sqrt{(X-X_{background})^2 + (Y-Y_{background})^2}$$

After the background has been fit, it's often desirable to extract a quantitative estimation of the size of the largest signal that may be hidden within the residual noise. Because the software recognizes shape, all we need to consider are oscillations in the noise that are similar to the shape of the modeled signals. (In ACV-4, signals have a characteristic period in voltage space: the center lobes commonly complete one cycle in about 0.16 volts.) By subtracting out the background fit and examining only the residual, we remove the low frequency background. To remove the high frequency noise, (thus considering only the signal-like oscillations), we push the residual through a low pass filter.[8] Any scan passed through this filter now holds only those oscillations that might represent an obscured signal. FIG. 65 shows the filtered, signal-like noise is drawn on top of the residual (Raw) from the previous example.

[8] To determine the appropriate filter parameters for ACV-4, we averaged the power spectra of the X and Y traces of several thousand files with signals. This yielded an average frequency ($V^{-1}$) profile which we used to choose the appropriate parameters to pass all signals. We commonly use an IFIR low pass filter. (The Interpolated FIR filter is described by Y. N. Neuvo et al. in *IEEE Trans. Acoust., Speech, Signal Processing*, vol. ASSP-32, pp. 563-570, June 1984.)

For ACV-4, since the vectoral signal is being fit independently in X and Y, the filtered residual can be quantified as follows:

$$\text{filtered}R_{center-to-peak} = \sqrt{2}(\text{filtered}R_{RMS}) = \sqrt{2(\text{filtered}X_{RMS}^2 + \text{filtered}Y_{RMS}^2)}$$

The RMS measurement was multiplied by sqrt[2] to convert it to a center-to-peak measure. We named this residual current value $i_r$.

$i_r$ gives an estimate of how much signal-like noise exists across the scan, but does not account for 1) any attenuation due to the filter, 2) for the fact that our signals are localized in a single region of the scan rather than spread across its entire length, or 3) for any possible limitations of the non-linear optimization when extracting a signal from noise. Because of this, $i_r$ alone would underestimate the largest possible hidden signal. Therefore we include a multiplicative factor "C" such that $C^* i_r$ is equal to the largest peak height ($i_p$) that might be obscured. In the above example, the largest possible missed signal is $C^* i_r = 7.57 \times 10^{-12}$.

Background Subtraction and Information Extraction

For scans with signals, once we have a fit, we're armed with all the information necessary for data analysis. Using the model as a guide, we can use the fit parameters to calculate the equation for the background alone and subtract this from the data. For example, in ACV-4 we can subtract the polynomial in X and in Y. FIG. 66 is the original data, FIG. 67 is the data with the background subtracted.

We can also calculate values of interest. For example, for ACV-4 we can calculate the peak height $i_p$ and the peak position $E_0$ based on the values fit in X and Y:

$$i_p = \sqrt{i_{pX}^2 + i_{pY}^2}$$

$$i_p = \sqrt{i_{pX}^2 + i_{pY}^2}$$

$$E_0 \equiv \frac{E_{0X} i_{pX}^2 + E_{0Y} i_{pY}^2}{i_{pX}^2 + i_{pY}^2}$$

$$\frac{E_{0X} i_{pX}^2 + E_{0Y} i_{pY}^2}{i_p^2}$$

In such a fashion, we are able to reduce an entire scan to a simple subset of experimentally meaningful numbers.

CONCLUSION

We have devised an automated method of fitting that reduces a data scan to a small number of parameters from which all experimentally meaningful information is extracted. Although we have focused on two-dimensional, vectoral data, simplified versions of the methods described here apply to 1-D scans. The important steps in the outlined procedure include: 1) assuming a model, 2) using vectoral sums to calculate an optimal phase, 3) checking for behaviors that do not conform to the model, 4) making an initial guess, using the inherent properties of the signal to minimize the effects of aberrant noise, 5) iterating to optimize the fit, perhaps while implementing a weighting scheme, 6) enforcing boundary conditions, 7) detecting and correcting flawed fits, 8) judging fit suitability, and 9) extracting meaningful quantitative information. By programming a computer to follow this process, we have derived an automated method that extracts meaningful data from one scan in less time than it takes the instrumentation to measure the next one.

Example 2

Rapid Extraction of Phase and Amplitude from a Noisy, Digitized Sine Wave of Known Frequency In extremely clean systems that create pure sine waves, one can determine a wave's phase by finding its zero-crossings and can measure its amplitude by finding local maxima and minima. If finding these extrema is too difficult, one can instead calculate the RMS of the wave, in which case the amplitude will be (the square root of 2) times the extracted RMS value. However, pure sine waves are rare in real world systems such as the systems described herein. Noise in the signal, particularly where the samples comprise biological materials, makes finding maxima, minima, and zero-crossings more difficult as methods to extract values. Furthermore, the RMS method measures power irrespective of frequency, so as the target signal decreases in amplitude, high frequency noise begins to dominate and swamp out the true signal.

Non-linear regression techniques can reliably extract values from noisy data, but they are iterative processes, and as such can take large amounts of computational time. This example is directed to the use of systems that involve only sums (and differences), and then renormalization and a basic coordinate transformation. As such, it is extremely rapid. Also, the sums which comprise all of the data reduction (from some large number of points per cycle to just two points per cycle) can easily be programmed into an embedded device, thus allowing more rapid data transfer from the acquisition device (e.g. the instrument of the invention) to the data manipulation and storage device (e.g. computer).

The following equations are used to extract phase and amplitude from a sinusoidal signal of known frequency that has been digitized such that it has 4n points per cycle. The summations that create X and Y are a means of averaging away any random noise, and are simple enough to be programmed into the firmware.

$$\left(ft + \frac{1}{4}\right)$$

then we create a circle of amplitude R centered at the origin. If we plot only one quarter of a circle, then we are using the values from half of ne cycle (the first quarter for y and the second for x). For this subset, we can calculate average values of y and x, called $\bar{y}_{1/2cycle}$ and $\bar{x}_{1/2cycle}$:

$$\bar{y}_{1/2cycle} = \frac{1}{1/4 - 0} \int_0^{1/4} R\sin(2\pi z + \phi) dz =$$

$$\frac{2R}{\pi}(\sin\phi + \cos\phi) = \frac{R \cdot 2\sqrt{2}}{\pi} \sin\left(\phi + \frac{\pi}{2}\right) \text{ and}$$

$$\bar{x}_{1/2cycle} =$$

$$\frac{1}{1/2 - 1/4} \int_{1/4}^{1/2} R\sin(2\pi z + \phi) dz = \frac{2R}{\pi}(\sin\phi - \cos\phi) = \frac{R \cdot 2\sqrt{2}}{\pi} \cos\left(\phi + \frac{\pi}{4}\right)$$

These values describe a point slightly within the arc of the quarter circle whose angle baisects the arc's sweep, and from them we can recover the original phase and amplitude:

$$\phi = \arctan\left(\frac{\bar{y}}{\bar{x}}\right)\frac{\pi}{4} \text{ and } R = \frac{\sqrt{\frac{-2-2}{x+y}}}{2\sqrt{2/\pi}}.$$

Note that, to include information from the entire cycle when calculating these average values, we can simply use the fact that $\sin(x) = -\sin(x+\pi/2)$ to find the same results:

$$\bar{y} = \frac{1}{2}\left[\frac{1}{1/4 - 0}\int_0^{1/4} R\sin(2\pi z + \phi)dz - \frac{1}{3/4 - 1/2}\int_{1/2}^{3/4} R\sin(2\pi z + \phi)dz\right] =$$

$$\frac{R \cdot 2\sqrt{2}}{\pi} \sin\left(\phi + \frac{\pi}{4}\right)$$

$$\bar{x} = \frac{1}{2}\left[\frac{1}{1/4 - 1/4}\int_{1/4}^{1/2} R\sin(2\pi z + \phi)dz - \frac{1}{1 - 3/4}\int_{3/4}^{1} R\sin(2\pi z + \phi)dz\right] =$$

$$\frac{R \cdot 2\sqrt{2}}{\pi} \cos\left(\phi + \frac{\pi}{4}\right)$$

We can exploit this behavior as follows: First, acquire an AC signal and lock into a desired frequency component. Choose the acquisition rate such that the number of points per cycle is evenly divisible by four—it can be written as 4n where n is an integer. The first n points correspond to the first quarter cycle, the second n points the second quarter, etc.

If we add all n data points in the first quarter of the cycle and subtract from them all n points in the third quarter, then we will have an unnormalized value, call it, analogous to the described above. Similarly, adding together the points in the second quarter and subtracting those in the fourth will yield. To extract the phase and amplitude from the data, we replace and by and in the equations for j and R above, but with a few alterations necessitated by the digitization:

$$\phi = \arctan\left(\frac{\tilde{Y}}{\tilde{X}}\right) - \frac{\pi}{4}\left(1 + \frac{1}{n}\right) \text{ and } R = \frac{\sqrt{\tilde{X}^2 + \tilde{Y}^2}}{2n \cdot C_n},$$

where $$C_n = \frac{1}{n}\sqrt{\left[\sum_{i=1}^{n}\cos\left(\frac{\pi}{2} \cdot \frac{i}{n}\right)\right]^2 + \left[\sum_{i=1}^{n}\sin\left(\frac{\pi}{2} \cdot \frac{i}{n}\right)\right]^2}.$$

In the above equation for R, $C_n$ has the following values:

| n | $C_n$ |
|---|---|
| 1 | 1.000000 |
| 2 | 0.923880 |
| 3 | 0.910684 |
| 4 | 0.906127 |
| 5 | 0.904029 |
| 6 | 0.902893 |
| 7 | 0.902208 |
| 8 | 0.901764 |
| 9 | 0.901460 |
| 10 | 0.901243 |
| 11 | 0.901082 |
| 12 | 0.900959 |
| 13 | 0.900864 |
| 14 | 0.900789 |
| 15 | 0.900728 |
| 20 | 0.900548 |
| 25 | 0.900464 |
| 30 | 0.900419 |
| 50 | 0.900353 |
| 70 | 0.900335 |
| 90 | 0.900328 |
| inf | 0.900316 |

(As n becomes very large, these equations approach those described above for the continuous case. 1/n goes to zero, and the value of 0.900316 listed for $C_{inf}$ is actually two times the square root of two over pi.)

The equations in the box on the previous page describe a procedure by which we can extract phase and amplitude from a sinusoidal signal of known frequency that has been digitized such that it has 4n points per cycle. The summations that create x and y are a means of averaging away any random noise, and are simple enough that they can be programmed into the firmware.

We claim:

1. A method of analyzing a plurality of biochips comprising
    a) inserting a first biochip into a first station of an analysis device;
    b) inserting a second biochip into a second station of the analysis device, wherein each of said first and second biochips comprise a substrate comprising:
        an array of detection electrodes, each comprising:
            i) a different capture binding ligand;
            ii) a different target analyte; and
            iii) a label; and;
        a plurality of electrical contacts;
    c) detecting current as an indication of the presence of said labels on said first biochip; and
    d) detecting current as an indication of the presence of said labels on said second biochip.

2. A method according to claim 1, wherein said capture binding ligands are nucleic acid capture probes, said target analytes are target nucleic acid sequences, and said nucleic acid capture probes hybridize to said target nucleic acid sequences to form hybridization complexes.

3. A method according to claim 2, wherein said hybridization complexes comprise said capture probes hybridized to said target sequences, respectively.

4. A method according to claim 2, wherein said labels are covalently attached to said target sequences.

5. A method according to claim 1 or 2, wherein said labels are hybridization indicators.

6. A method according to claim 5, wherein said hybridization indicators are intercalators.

7. A method according to claim 2, wherein said target sequences each comprise a first domain and a second domain, said hybridization complexes each comprise:
    a) said capture probes hybridized to said first domains of said target sequences; and
    b) label probes hybridized to said second domains of said target sequences.

8. A method according to claim 7 wherein said label probes each comprise three or more covalently attached labels.

9. A method according to claim 1, 2 or 8 wherein said labels are electron transfer moieties (ETMs).

10. A method according to claim 9 wherein said ETMs are transition metal complexes.

11. A method according to claim 10 wherein said transition metal complexes are metallocenes.

12. A method according to claim 1, further comprising:
    a) receiving detection information from said first biochip at a processor; and
    b) receiving detection information from said second biochip at said processor.

13. A method according to claim 12, further comprising analyzing said received detection information.

14. A method according to claim 13, wherein said analyzing step comprises analyzing higher harmonic frequencies.

* * * * *